US 9,975,882 B2
May 22, 2018

(12) United States Patent
Bosanac et al.

(10) Patent No.: US 9,975,882 B2
(45) Date of Patent: May 22, 2018

(54) HETEROAROMATIC COMPOUNDS AS BTK INHIBITORS

(71) Applicant: Boehringer Ingelheim International GmbH, Ingelheim am Rhein (DE)

(72) Inventors: Todd Bosanac, New Milford, CT (US); Joerg Bentzien, White Plains, NY (US); Michael Jason Burke, Newtown, CT (US); Ryan Michael Fryer, Brewster, NY (US); Eric Thomas Larson, Bethel, CT (US); Wang Mao, Milford, CT (US); Bryan Patrick McKibben, New Milford, CT (US); Yue Shen, Berlin, CT (US); Fariba Soleymanzadeh, Danbury, CT (US); Matt Aaron Tschantz, Newtown, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days. days.

(21) Appl. No.: 15/379,745

(22) Filed: Dec. 15, 2016

(65) Prior Publication Data

US 2017/0174663 A1    Jun. 22, 2017

Related U.S. Application Data

(60) Provisional application No. 62/431,008, filed on Dec. 7, 2016, provisional application No. 62/268,278, filed on Dec. 16, 2015.

(51) Int. Cl.
   *C07D 401/14* (2006.01)
   *C07D 403/14* (2006.01)

(52) U.S. Cl.
   CPC ......... *C07D 403/14* (2013.01); *C07D 401/14* (2013.01)

(58) Field of Classification Search
   CPC .................. C07D 401/14; C07D 403/14
   See application file for complete search history.

(56) References Cited

U.S. PATENT DOCUMENTS

| | | | |
|---|---|---|---|
| 7,560,571 | B2 | 7/2009 | Ronan et al. |
| 8,377,946 | B1 | 2/2013 | Chen et al. |
| 8,557,803 | B2 | 10/2013 | Yamamoto et al. |
| 2004/0198986 | A1 | 10/2004 | Adams et al. |
| 2008/0045542 | A1 | 2/2008 | Ronan et al. |
| 2008/0076921 | A1 | 3/2008 | Honigberg et al. |
| 2009/0012309 | A1 | 1/2009 | Adams et al. |
| 2011/0003806 | A1 | 1/2011 | Hirose et al. |
| 2014/0045813 | A1 | 2/2014 | Bentzien et al. |
| 2016/0340339 | A1 | 11/2016 | Bentzien et al. |

FOREIGN PATENT DOCUMENTS

| | | |
|---|---|---|
| CA | 2784647 A1 | 7/2011 |
| EP | 2543375 A1 | 1/2013 |
| WO | 9740019 A1 | 10/1997 |
| WO | 03015776 A1 | 2/2003 |
| WO | 2007117692 A2 | 10/2007 |
| WO | 2008039218 | 4/2008 |
| WO | 2008039218 A2 | 4/2008 |
| WO | 2008121742 A2 | 10/2008 |
| WO | 2010012690 | 2/2010 |
| WO | 2010012690 A1 | 2/2010 |
| WO | 2010055304 A2 | 5/2010 |
| WO | 2010090716 A1 | 8/2010 |
| WO | 2011082732 A1 | 7/2011 |
| WO | 2011152351 A1 | 12/2011 |
| WO | 2012021615 A1 | 2/2012 |
| WO | 2013113097 | 8/2013 |
| WO | 2013113097 A1 | 8/2013 |
| WO | 2014025976 A1 | 2/2014 |
| WO | 2014068527 A1 | 5/2014 |
| WO | 2014082598 A1 | 6/2014 |

OTHER PUBLICATIONS

Abstract in English for WO 2011/082732, publication date Jul. 14, 2011.
Akinleye, A. et al., "Ibrutinib and novel BTK inhibitors in clinical develoopment." Journal of Hematology & Oncology, 2013, 6:59, pp. 1-9.
International Search Report and Written Opinion for PCT/US2013/054096 dated Sep. 30, 2013.
International Search Report and Written Opinion for PCT/US2014/026113, dated Jun. 2, 2014.
International Search Report and Written Opinion for PCT/U52014/026966, dated Jul. 22, 2014.
International Search Report and Written Opinion for PCT/U52015/012590 dated Mar. 25, 2015.

(Continued)

*Primary Examiner* — Laura L. Stockton
(74) *Attorney, Agent, or Firm* — Marc A. Began; Atabak R. Royaee

(57) ABSTRACT

The present invention encompasses compounds of the formula (I)

(I)

$$H_2N-\overset{O}{\underset{}{\|}}-\underset{\underset{R_1}{|}}{\underset{HN}{\diagdown}}\overset{}{\underset{}{\diagup}}\overset{Cy,}{\underset{N}{\diagdown}}\underset{Y}{\diagup}N$$

wherein the groups $R_1$, Cy and Y are defined herein, which are suitable for the treatment of diseases related to BTK, and processes for making these compounds, pharmaceutical preparations containing these compounds, and their methods of use.

40 Claims, 1 Drawing Sheet

(56) References Cited

OTHER PUBLICATIONS

International Search Report for PCT/US2015/012590 dated Mar. 25, 2015.
International Search Report PCT/U52016/066799 dated Jul. 12, 2017. 4 pgs.
Summary of Pfizer Oral Presentation, "Targeted covalent reversible inhibitors for Bruton's Tyrosine Kinase." Presented by Suvit Thaisrivongs on Apr. 16, 2013.
Whang, J. et al., "Bruton's tyrosine kinase inhibitors for the treatment of rheumatoid arthritis." Drug Discovery Today, 2014, pp. 1-5.
Chakravarty, S. et al., "Kinase inhibitors: A new tool for the treatment of rheumatoid arthritis." Clinical Immunology, 2013, vol. 148, pp. 66-78.

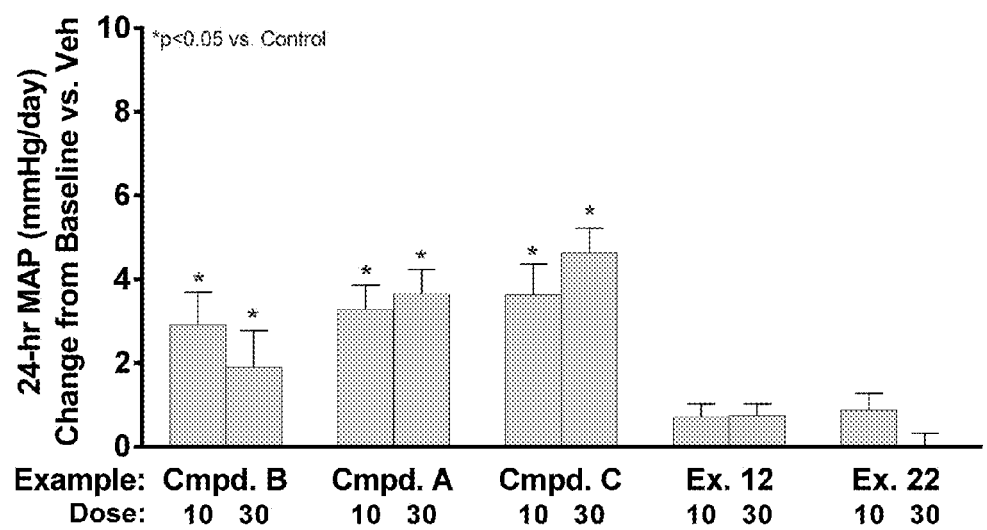

HETEROAROMATIC COMPOUNDS AS BTK INHIBITORS

RELATED APPLICATIONS

This application claims priority to U.S. Provisional Application Nos. 62/268,278 filed Dec. 16, 2015, and 62/431,008 filed Dec. 7, 2016, the entire contents of which are hereby incorporated herein by reference.

TECHNICAL FIELD

The present invention relates to novel compounds which inhibit BTK and their use as medicaments.

BACKGROUND INFORMATION

Members of the protein kinase family of human enzymes play important regulatory roles in a multitude of distinct signal transduction processes due to their post-translational modification of specific proteins via the addition of a phosphate group (Hunter, *Cell* 1987, 50, 823-829). Bruton's tyrosine kinase (BTK) is a member of the Tec family of tyrosine kinases and plays a critical role in B cell development, activation and antibody production.

The contribution of BTK to B cell biology is exemplified in the X-linked agammaglobulinemia (XLA) immunodeficiency in humans (reviewed in Lindvall, *Immunol. Rev.* 2005, 203, 200-215) that display attenuated calcium signaling upon B cell receptor (BCR) engagement, lack mature B cells in the periphery due to block between pro- and pre-B cell stage and have lower levels of circulating antibodies than normal healthy subjects. The outcome of recent clinical trials with B cell depleting anti-CD20 molecules in diseases such as rheumatoid arthritis (RA) and multiple sclerosis (MS) support the hypothesis that B cells offer an important intervention node for controlling autoimmune disorders (Townsend, *Immunol. Rev.* 2010, 237, 264-283). As such, attenuation of B cell activation and proliferation via inhibition of BTK may offer similar therapeutic benefit and is consistent with the demonstrated resistance of BTK-deficient mice to collagen induced arthritis (Jansson, *Clin. Exp. Immunol.* 1993, 94, 459-465) and experimental autoimmune encephalitis (Svensson, *Eur. J. Immunol.* 2002, 32, 1939-1946 and Mangla, *Blood* 2004, 104, 1191-1197). Similarly, the clinical efficacy observed with a neutralizing antibody to the B cell stimulating factor BlyS supports a role for B cells in the pathophysiology of systemic lupus erythematosus (SLE) (La Cava, *Expert Opin. Biol. Ther.* 2010, 10, 1555-1561). Given the necessity for BTK for the production of autoantibodies, including anti-DNA antibodies, in murine models of SLE (Steinberg, *J. Clin. Invest.* 1982, 70, 587-597; Golding, *J. Immunol.* 1983, 130, 1043-1046; Scribner, *J. Immunol.* 1987, 138, 3611-3617; Seldin, *J. Exp. Med.* 1987, 166, 1585-1590; Takeshita, *Int. Immunol.* 1998, 10, 435-4444; Whyburn, *J. Immunol.* 2003, 171, 1850-1858), BTK inhibitors may offer therapeutic benefit to SLE patients.

Within myeloid cells, BTK signal transduction is necessary for the stimulated release of inflammatory cytokines such as TNFα from stimulated monocytes (Horwood, *J. Exp. Med.* 2003, 197, 1603-1611) and for optimal actin cytoskeletal organization and lacunar bone resorption in isolated osteoclasts (Danks, *J. Bone Miner. Res.* 2010, 26, 182-192). Bone marrow derived mast cells lacking BTK exhibit impaired activation-induced degranulation and cytokine release. Given the role of BTK in signal transduction processes across multiple cell types implicated in the pathogenesis of autoimmune and allergic disorders, inhibition of BTK activity may provide clinical benefit in diseases such as RA, MS, SLE, lupus nephritis, Sjogren's disease, vasculitis, asthma and allergic disorders.

SUMMARY OF THE INVENTION

Currently, compounds such as A and C (discussed below), and those depicted in, for example, PCT publication number WO2014025976 are known as BTK inhibitors. However, as provided herein below, these compounds cross-react with and inhibit other kinases. Hence, these representatives are not selective for BTK over other targets. The lack of selective BTK inhibition increases the likelihood of adverse effects in a clinical setting.

Beside efficacy and selectivity, a therapeutic compound must have a favorable safety profile such as cardiovascular safety. One parameter for assessing the cardiovascular (CV) safety of a compound is the mean arterial pressure (MAP). A statistically significant change in MAP in a pre-clinical rat CV safety study is indicative of adverse cardiovascular events in human. As provided herein below, comparative compounds A, B, and C show statistically significant increases in MAP in a rat CV study. The data suggests that these compounds may not have a favorable cardiovascular safety profile in human.

In view of the above-mentioned safety concerns with the other known BTK inhibitors, there still remains a need for additional compounds that are highly selective for BTK inhibition and do not have an adverse impact on relevant cardiovascular parameters such as MAP.

The compounds of the present invention maintain the requisite potent inhibitory activity against BTK to treat the aforementioned BTK-related diseases, and solve the selectivity and cardiovascular safety problems associated with other known BTK inhibitors such as those represented by comparative compounds A, B, and C (discussed below). The BTK selectivity and the favorable cardiovascular safety profile that are demonstrated by the compounds of the instant invention represent unexpected and surprising improvements over other known BTK inhibitors.

In particular, the compounds of the present invention solve the efficacy and safety problems associated with other known BTK inhibitors by maintaining a high level of potency and selectivity in inhibiting the BTK activity without having any statistically significant effects on MAP.

Accordingly, this invention comprises a novel class of heteroaromatic compounds and methods for making and using the same. These compounds are useful for the treatment of autoimmune and allergic disorders in that they exhibit excellent inhibitory effect upon BTK.

In a first generic embodiment, there is provided a compound of the formula (I)

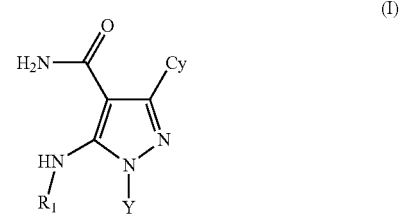

(I)

in which:

Cy is chosen from

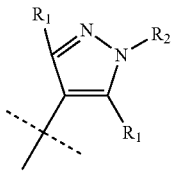 or 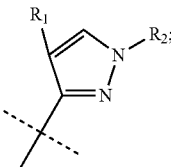

each $R_1$ is independently chosen from hydrogen or methyl;

$R_2$ is L-Ar, wherein Ar is phenyl or pyridinyl and each is optionally substituted by one or more of halogen, halo $C_{1-4}$ alkyl, $C_{1-4}$ alkyl, $C_{1-4}$ alkoxy, —CN, halo $C_{1-4}$ alkoxy, or cycloalkyl;

L is —(CH$_2$)— or —(CHCH$_3$)—;

Y is $C_6$-$C_8$ spirocycle containing 1 ring nitrogen atom, and is substituted by one $R_3$;

$R_3$ is chosen from

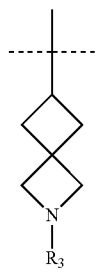 or 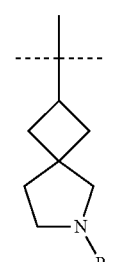

each $R_4$ is independently chosen from hydrogen, $C_{1-4}$ alkyl, or $C_{3-4}$ cycloalkyl; each group defined above for $R_1$-$R_4$ and Y can be where possible partially or fully halogenated;

or a pharmaceutically acceptable salt or hydrate thereof.

In a further embodiment, there is provided a compound of the formula (I) according to the embodiment herein-above and in which:

Y is chosen from

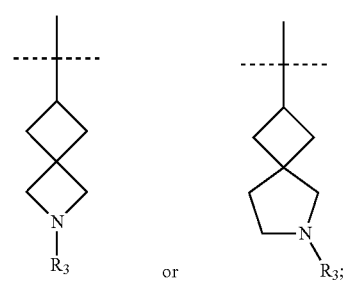

or a pharmaceutically acceptable salt or hydrate thereof.

In a further embodiment, there is provided a compound of the formula (I) according to the embodiments herein-above and in which:

Cy is

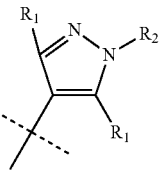

Y is chosen from

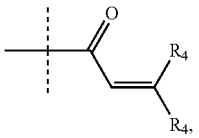 or 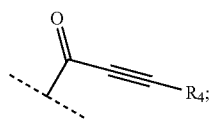

$R_3$ is

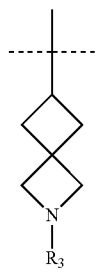 or 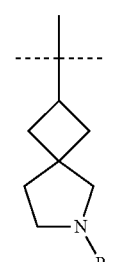

in which each $R_4$ is independently chosen from hydrogen, $C_{1-4}$ alkyl, or $C_{3-4}$ cycloalkyl;

or a pharmaceutically acceptable salt or hydrate thereof.

In a further embodiment, there is provided a compound of the formula (I) according to the embodiment herein-above and in which:

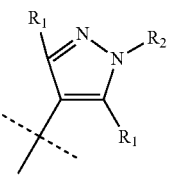

Y is chosen from

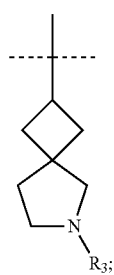

$R_3$ is

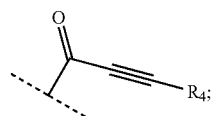

in which $R_4$ is chosen from hydrogen, $C_{1-4}$ alkyl, or $C_{3-4}$ cycloalkyl;
or a pharmaceutically acceptable salt or hydrate thereof.

In a further embodiment, there is provided a compound of the formula (I) according to the embodiment herein-above and in which:
Cy is

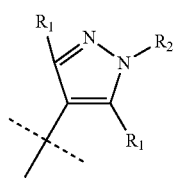

Y is chosen from

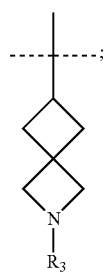

$R_3$ is

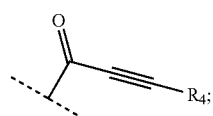

in which $R_4$ is chosen from hydrogen, $C_{1-4}$ alkyl, or $C_{3-4}$ cycloalkyl;
or a pharmaceutically acceptable salt or hydrate thereof.

In a further embodiment, there is provided a compound of the formula (I) according to the embodiment herein-above and in which:
Cy is

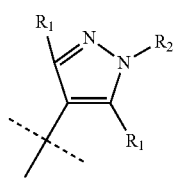

Y is chosen from

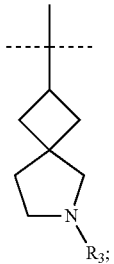

$R_3$ is

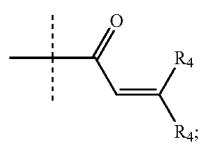

in which each $R_4$ is independently chosen from hydrogen, $C_{1-4}$ alkyl, or $C_{3-4}$ cycloalkyl;
or a pharmaceutically acceptable salt or hydrate thereof.

In a further embodiment, there is provided a compound of the formula (I) according to the embodiment herein-above and in which:
Cy is

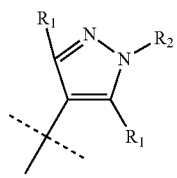

Y is chosen from

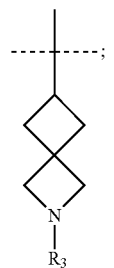

$R_3$ is

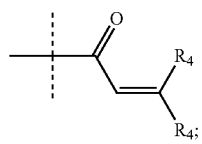

in which each $R_4$ is independently chosen from hydrogen, $C_{1-4}$ alkyl, or $C_{3-4}$ cycloalkyl;
or a pharmaceutically acceptable salt or hydrate thereof.

In a further embodiment, there is provided a compound of the formula (I) according to any of the embodiments hereinabove and in which:

each $R_4$ is independently chosen from hydrogen, methyl, or cyclopropyl;

or a pharmaceutically acceptable salt or hydrate thereof.

In a further embodiment, there is provided a compound of the formula (I) according to any of the embodiments hereinabove and in which:

$R_2$ is L-Ar, wherein Ar is phenyl or pyridinyl and each is optionally substituted by one or more of halogen, haloethyl, methyl, methoxy, —CN, halomethoxy, or cyclopropyl;

L is —(CH$_2$)— or —(CHCH$_3$)— or a pharmaceutically acceptable salt or hydrate thereof.

In another embodiment, the invention provides made compounds in Table I which can be made in view of the general schemes, examples and methods described herein and those known in the art.

TABLE I

| | | | | | |
|---|---|---|---|---|---|
| Biological and physical properties of representatives of the present invention | | | | | |
| Example | Structure | BTK IC$_{50}$ (nM) | HPLC Method | RT (min) | m/z [M + H]$^+$ |
| 1 | 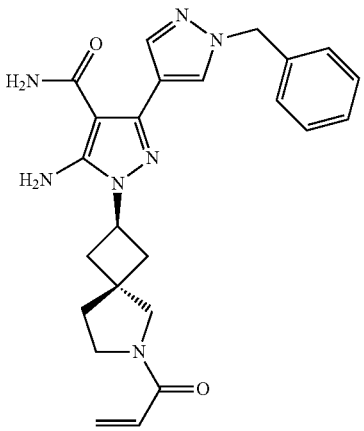 [SMILES: C=CC(=O)N1CC[C@]2(C1)C[C@H](n1nc(-c3cnn(Cc4ccccc4)c3)c(C(N)=O)c1N)C2] | 36 | A | 0.65 | 446.4 |
| 2 | 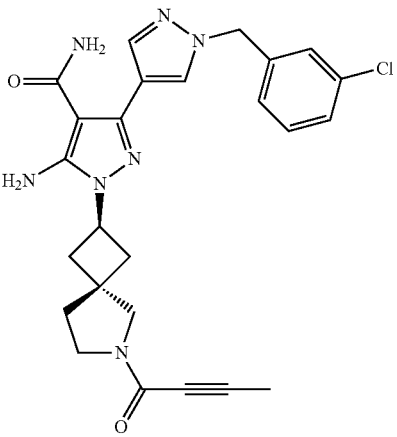 [SMILES: CC#CC(=O)N1CC[C@]2(C1)C[C@H](n1nc(-c3cnn(Cc4cccc(Cl)c4)c3)c(C(N)=O)c1N)C2] | 0.3 | B | 0.596 | 491.1 |

TABLE I-continued
Biological and physical properties of representatives of the present invention
| Example | Structure | BTK IC$_{50}$ (nM) | HPLC Method | RT (min) | m/z [M + H]$^+$ |
|---|---|---|---|---|---|
| 3 | 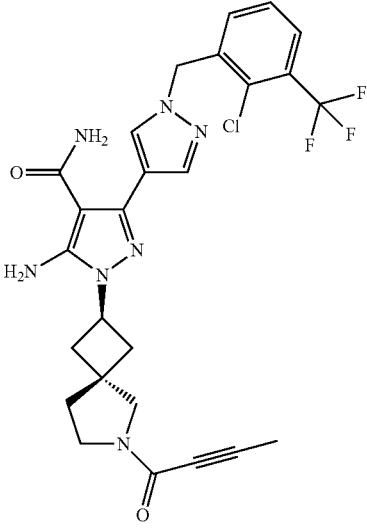 [SMILES: CC#CC(=O)N1CC[C@]2(C1)C[C@H](n1nc(-c3cnn(Cc4cccc(C(F)(F)F)c4Cl)c3)c(C(N)=O)c1N)C2] | 0.4 | B | 0.797 | 559.1 |
| 4 | 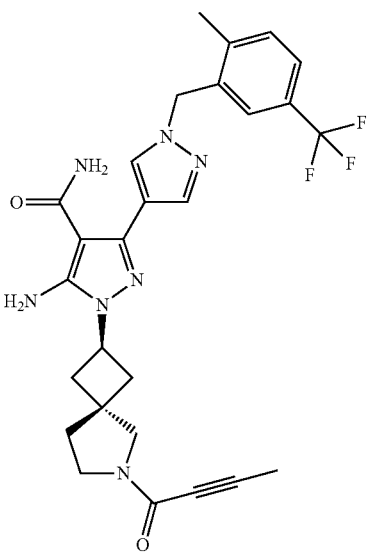 [SMILES: CC#CC(=O)N1CC[C@]2(C1)C[C@H](n1nc(-c3cnn(Cc4cc(C(F)(F)F)ccc4C)c3)c(C(N)=O)c1N)C2] | 1.8 | B | 0.795 | 540.3 |

TABLE I-continued

Biological and physical properties of representatives of the present invention

| Example | Structure | BTK IC$_{50}$ (nM) | HPLC Method | RT (min) | m/z [M + H]$^+$ |
|---|---|---|---|---|---|
| 5 | 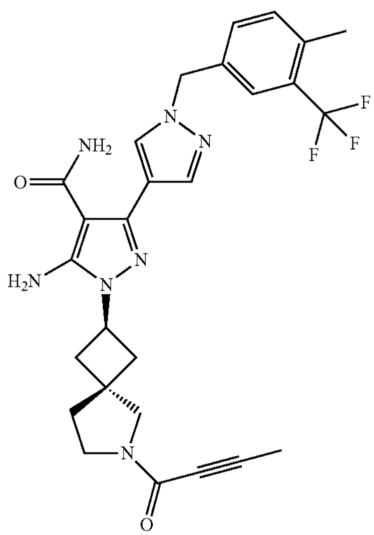 [SMILES: CC#CC(=O)N1CC[C@]2(C1)C[C@H](n1nc(-c3cnn(Cc4ccc(C)c(C(F)(F)F)c4)c3)c(C(N)=O)c1N)C2] | 0.4 | B | 0.808 | 540.3 |
| 6 | 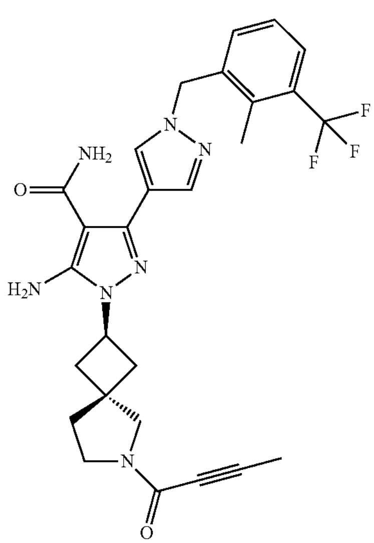 | 0.4 | B | 0.813 | 540.3 |

TABLE I-continued

Biological and physical properties of representatives of the present invention

| Example | Structure | BTK IC$_{50}$ (nM) | HPLC Method | RT (min) | m/z [M + H]$^+$ |
|---|---|---|---|---|---|
| 7 | 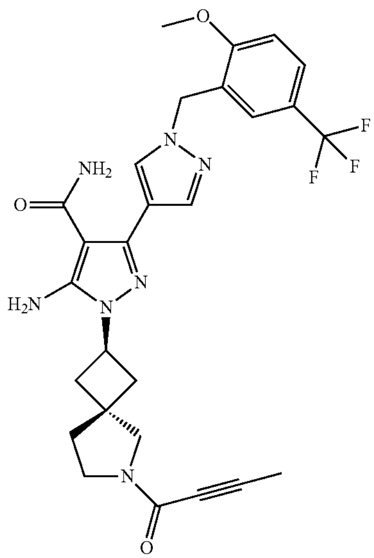 [SMILES: CC#CC(=O)N1CC[C@]2(C1)C[C@H](n1nc(-c3cnn(Cc4cc(C(F)(F)F)ccc4OC)c3)c(C(N)=O)c1N)C2] | 3.3 | B | 0.778 | 555.2 |
| 8 | 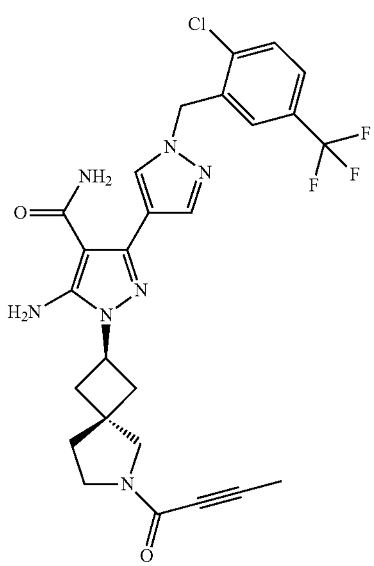 [SMILES: CC#CC(=O)N1CC[C@]2(C1)C[C@H](n1nc(-c3cnn(Cc4cc(C(F)(F)F)ccc4Cl)c3)c(C(N)=O)c1N)C2] | 0.9 | B | 0.80 | 559.1 |

TABLE I-continued
Biological and physical properties of representatives of the present invention
| Example | Structure | BTK IC$_{50}$ (nM) | HPLC Method | RT (min) | m/z [M + H]$^+$ |
|---|---|---|---|---|---|
| 9 | 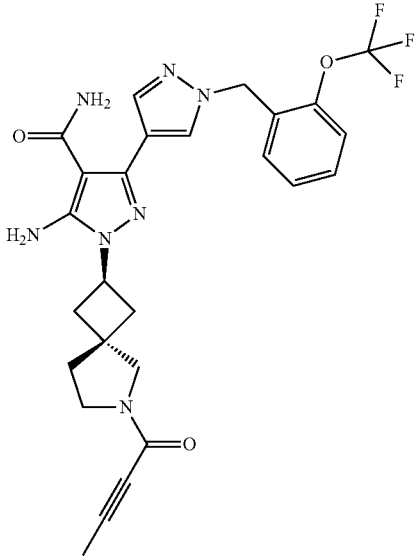 [SMILES: CC#CC(=O)N1CC[C@]2(C1)C[C@H](n1nc(-c3cnn(Cc4ccccc4OC(F)(F)F)c3)c(C(N)=O)c1N)C2] | 0.6 | A | 0.80 | 542.3 |
| 10 | 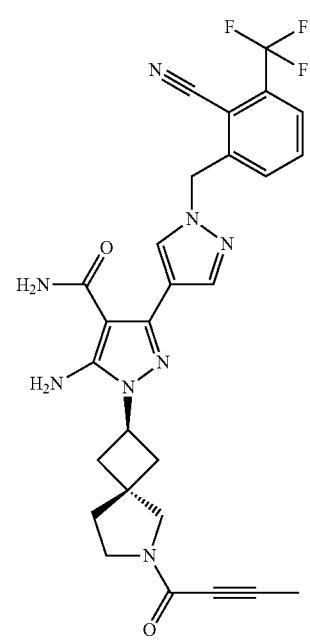 [SMILES: CC#CC(=O)N1CC[C@]2(C1)C[C@H](n1nc(-c3cnn(Cc4cccc(C(F)(F)F)c4C#N)c3)c(C(N)=O)c1N)C2] | 0.5 | B | 0.751 | 551.3 |

TABLE I-continued

Biological and physical properties of representatives of the present invention

| Example | Structure | BTK IC$_{50}$ (nM) | HPLC Method | RT (min) | m/z [M + H]$^+$ |
|---|---|---|---|---|---|
| 11 | 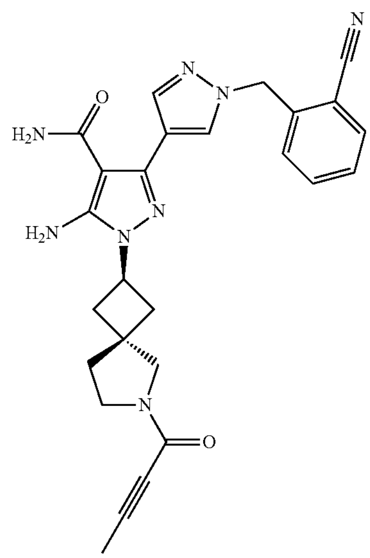 [SMILES: CC#CC(=O)N1CC[C@]2(C1)C[C@H](n1nc(-c3cnn(Cc4ccccc4C#N)c3)c(C(N)=O)c1N)C2] | 0.7 | B | 0.647 | 483.3 |
| 12 | 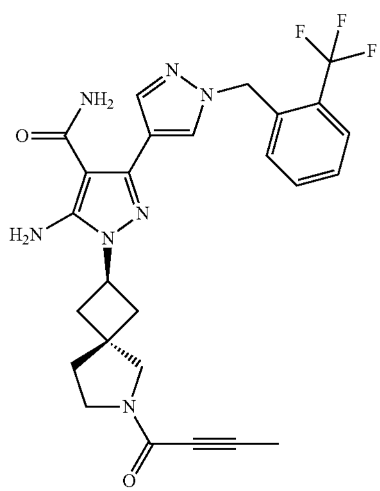 [SMILES: CC#CC(=O)N1CC[C@]2(C1)C[C@H](n1nc(-c3cnn(Cc4ccccc4C(F)(F)F)c3)c(C(N)=O)c1N)C2] | 0.5 | B | 0.770 | 526.4 |
| 13 | 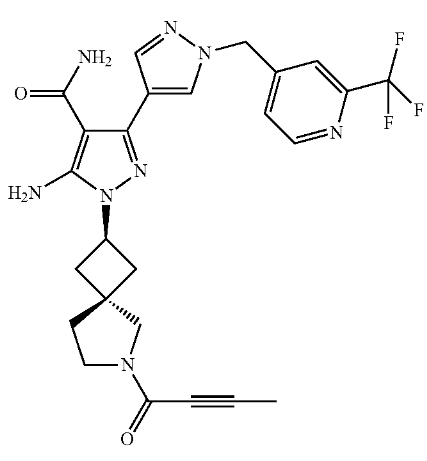 [SMILES: CC#CC(=O)N1CC[C@]2(C1)C[C@H](n1nc(-c3cnn(Cc4ccnc(C(F)(F)F)c4)c3)c(C(N)=O)c1N)C2] | 9.1 | B | 0.665 | 527.2 |

TABLE I-continued
Biological and physical properties of representatives of the present invention
| Example | Structure | BTK IC$_{50}$ (nM) | HPLC Method | RT (min) | m/z [M + H]$^+$ |
|---|---|---|---|---|---|
| 14 | 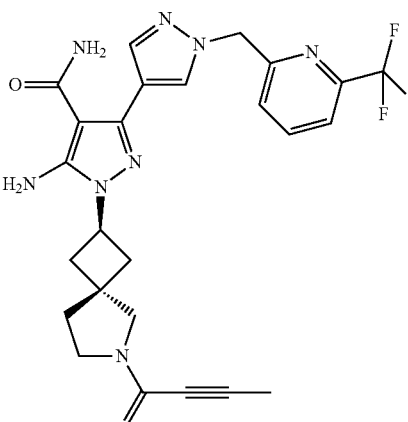 | 0.5 | B | 0.7 | 527.2 |
| 15 | 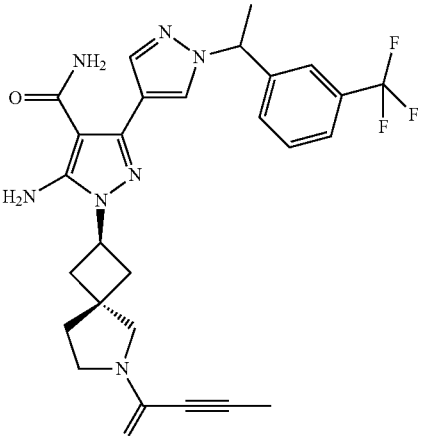 | 1.1 | B | 0.814 | 540.3 |
| 16 | 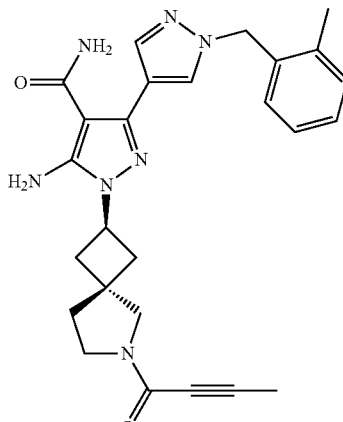 | 1.5 | B | 0.595 | 472.5 |

TABLE I-continued
Biological and physical properties of representatives of the present invention
| Example | Structure | BTK IC$_{50}$ (nM) | HPLC Method | RT (min) | m/z [M + H]$^+$ |
|---|---|---|---|---|---|
| 17 | 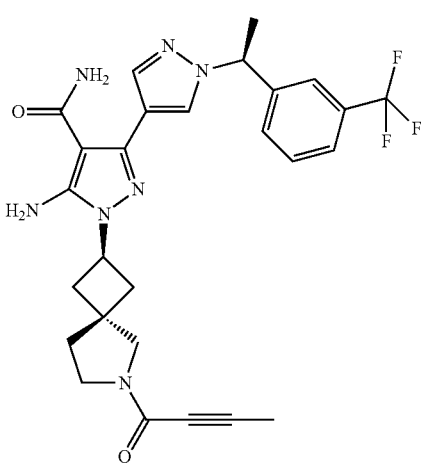 [SMILES: CC#CC(=O)N1CC[C@]2(C1)C[C@H](n1nc(-c3cnn([C@@H](C)c4cccc(C(F)(F)F)c4)c3)c(C(N)=O)c1N)C2] | 1.7 | B | 0.798 | 539.2 |
| 18 | 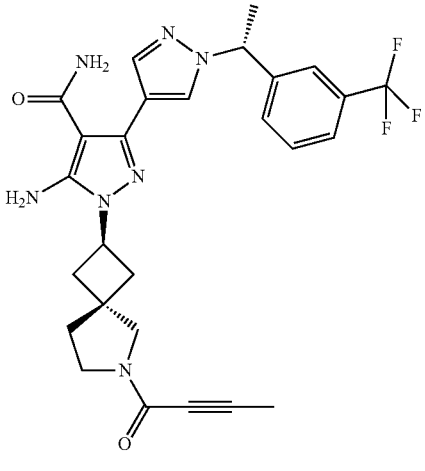 [SMILES: CC#CC(=O)N1CC[C@]2(C1)C[C@H](n1nc(-c3cnn([C@H](C)c4cccc(C(F)(F)F)c4)c3)c(C(N)=O)c1N)C2] | 0.6 | B | 0.798 | 539.2 |
| 19 | 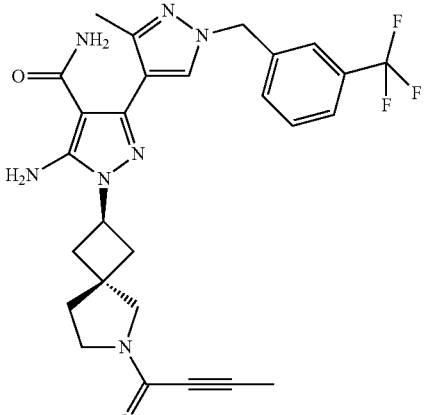 | 0.9 | B | 0.777 | 540.3 |

TABLE I-continued

Biological and physical properties of representatives of the present invention

| Example | Structure | BTK IC$_{50}$ (nM) | HPLC Method | RT (min) | m/z [M + H]$^+$ |
|---------|-----------|--------------------|-------------|----------|------------------|
| 20 | 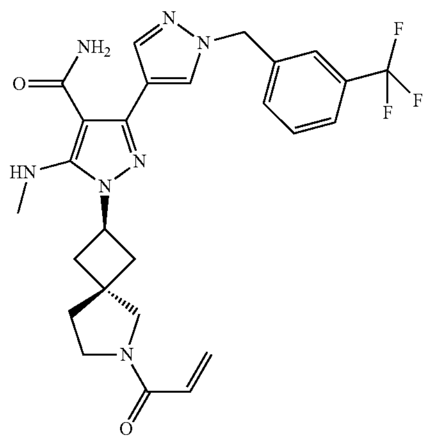 [SMILES: C=CC(=O)N1CC[C@]2(C1)C[C@H](n1nc(-c3cnn(Cc4cccc(C(F)(F)F)c4)c3)c(C(N)=O)c1NC)C2] | 22 | B | 0.741 | 528.7 |
| 21 | 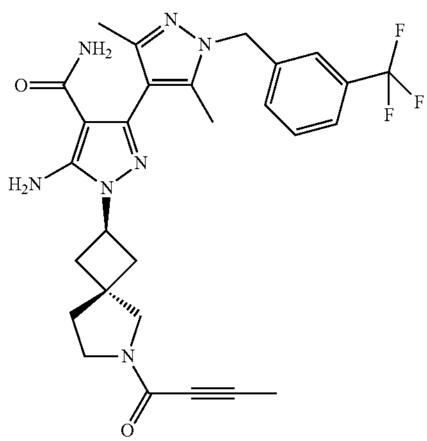 [SMILES: CC#CC(=O)N1CC[C@]2(C1)C[C@H](n1nc(-c3c(C)nn(Cc4cccc(C(F)(F)F)c4)c3C)c(C(N)=O)c1N)C2] | 5.8 | B | 0.786 | 554.3 |
| 22 | 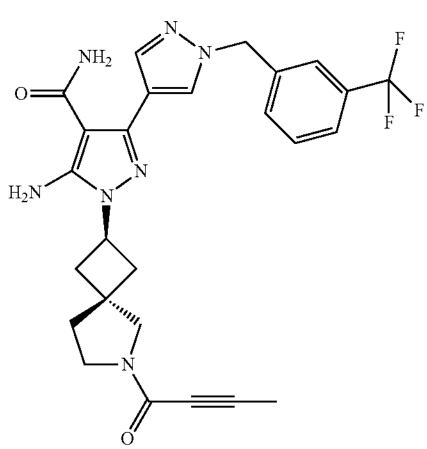 [SMILES: CC#CC(=O)N1CC[C@]2(C1)C[C@H](n1nc(-c3cnn(Cc4cccc(C(F)(F)F)c4)c3)c(C(N)=O)c1N)C2] | 0.3 | B | 0.760 | 526.3 |

TABLE I-continued

Biological and physical properties of representatives of the present invention

| Example | Structure | BTK IC$_{50}$ (nM) | HPLC Method | RT (min) | m/z [M + H]$^+$ |
|---|---|---|---|---|---|
| 23 | 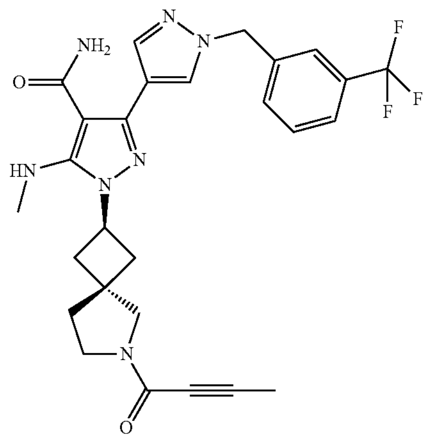 [SMILES: CC#CC(=O)N1CC[C@]2(C1)C[C@H](n1nc(-c3cnn(Cc4cccc(C(F)(F)F)c4)c3)c(C(N)=O)c1NC)C2] | 1.3 | B | 0.796 | 540.3 |
| 24 | 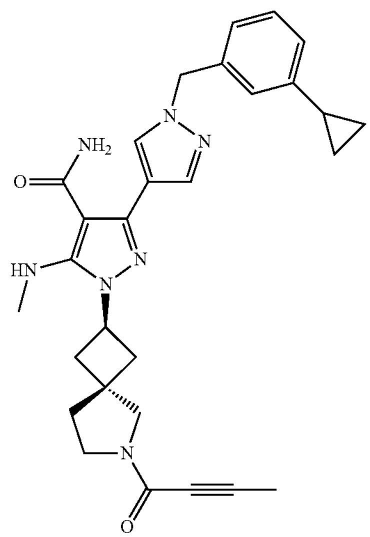 [SMILES: CC#CC(=O)N1CC[C@]2(C1)C[C@H](n1nc(-c3cnn(Cc4cccc(C5CC5)c4)c3)c(C(N)=O)c1NC)C2] | 0.8 | B | 0.801 | 512.4 |
| 25 | 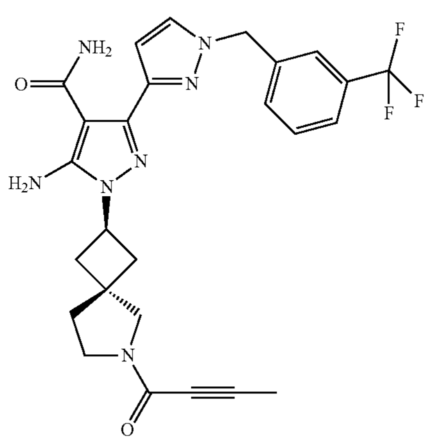 [SMILES: CC#CC(=O)N1CC[C@]2(C1)C[C@H](n1nc(-c3ccn(Cc4cccc(C(F)(F)F)c4)n3)c(C(N)=O)c1N)C2] | 2.6 | B | 0.843 | 526.3 |

TABLE I-continued

Biological and physical properties of representatives of the present invention

| Example | Structure | BTK IC$_{50}$ (nM) | HPLC Method | RT (min) | m/z [M + H]$^+$ |
|---|---|---|---|---|---|
| 26 | 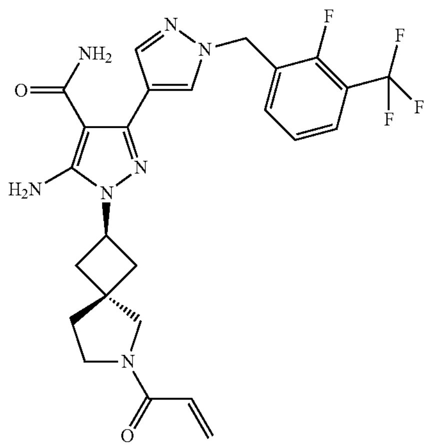 [SMILES: C=CC(=O)N1CC[C@]2(C1)C[C@H](n1nc(-c3cnn(Cc4cccc(C(F)(F)F)c4F)c3)c(C(N)=O)c1N)C2] | 2.6 | C | 1.78 | 532.4 |
| 27 | 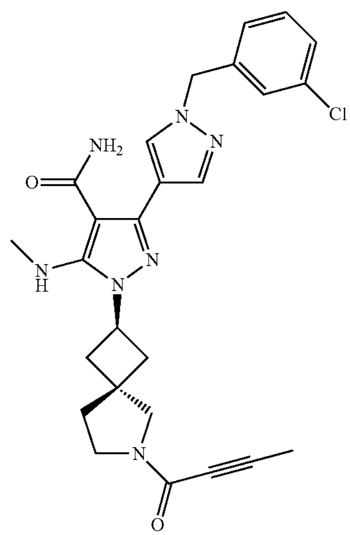 [SMILES: CC#CC(=O)N1CC[C@]2(C1)C[C@H](n1nc(-c3cnn(Cc4cccc(Cl)c4)c3)c(C(N)=O)c1NC)C2] | 1.7 | B | 0.769 | 506.3 |
| 28 | 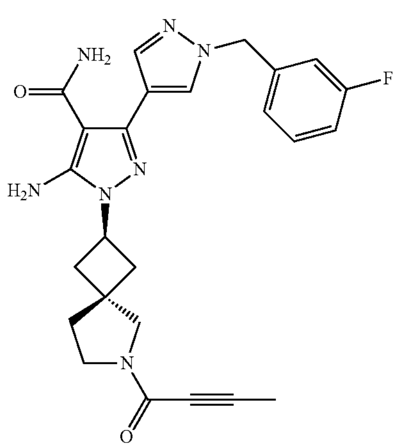 [SMILES: CC#CC(=O)N1CC[C@]2(C1)C[C@H](n1nc(-c3cnn(Cc4cccc(F)c4)c3)c(C(N)=O)c1N)C2] | 0.3 | B | 0.692 | 476.4 |

TABLE I-continued

Biological and physical properties of representatives of the present invention

| Example | Structure | BTK IC$_{50}$ (nM) | HPLC Method | RT (min) | m/z [M + H]$^+$ |
|---------|-----------|--------------------|-------------|----------|-----------------|
| 29 | 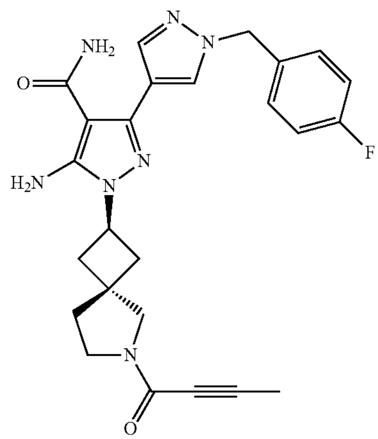 [SMILES: CC#CC(=O)N1CC[C@]2(C1)C[C@H](n1nc(-c3cnn(Cc4ccc(F)cc4)c3)c(C(N)=O)c1N)C2] | 0.8 | B | 0.69 | 476.4 |
| 30 | 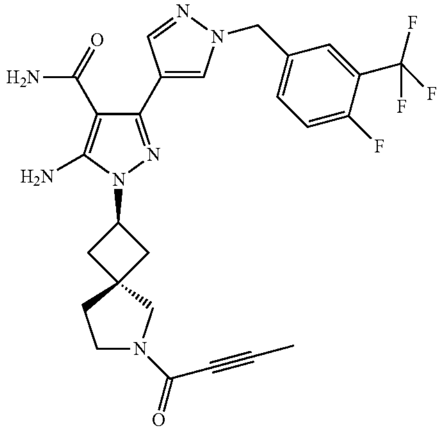 [SMILES: CC#CC(=O)N1CC[C@]2(C1)C[C@H](n1nc(-c3cnn(Cc4ccc(F)c(C(F)(F)F)c4)c3)c(C(N)=O)c1N)C2] | 0.6 | B | 0.786 | 544.4 |
| 31 | 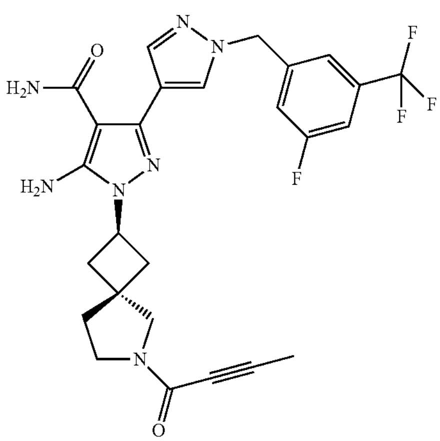 | 0.8 | B | 0.779 | 544.3 |

TABLE I-continued

Biological and physical properties of representatives of the present invention

| Example | Structure | BTK IC$_{50}$ (nM) | HPLC Method | RT (min) | m/z [M + H]$^+$ |
|---|---|---|---|---|---|
| 32 | 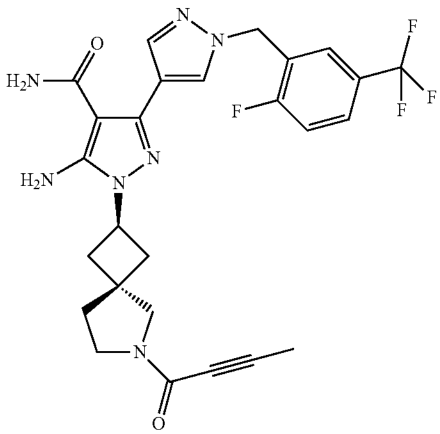 [SMILES: CC#CC(=O)N1CC[C@]2(C1)C[C@H](n1nc(-c3cnn(Cc4cc(C(F)(F)F)ccc4F)c3)c(C(N)=O)c1N)C2] | 0.5 | B | 0.772 | 544.4 |
| 33 | 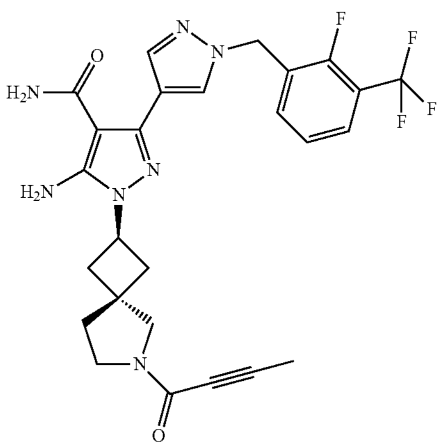 [SMILES: CC#CC(=O)N1CC[C@]2(C1)C[C@H](n1nc(-c3cnn(Cc4cccc(C(F)(F)F)c4F)c3)c(C(N)=O)c1N)C2] | 0.4 | B | 0.78 | 544.2 |
| 34 | 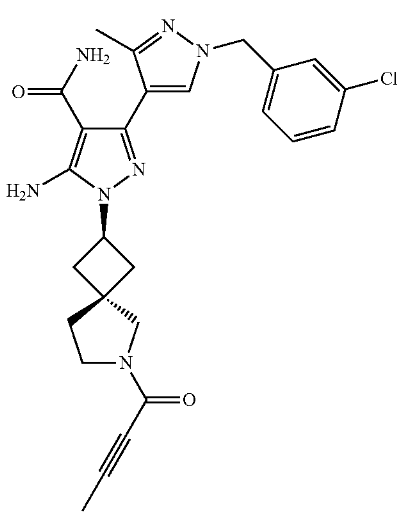 [SMILES: CC#CC(=O)N1CC[C@]2(C1)C[C@H](n1nc(-c3cn(Cc4cccc(Cl)c4)nc3C)c(C(N)=O)c1N)C2] | 0.7 | B | 0.753 | 506.2 |

TABLE I-continued

Biological and physical properties of representatives of the present invention

| Example | Structure | BTK IC$_{50}$ (nM) | HPLC Method | RT (min) | m/z [M + H]$^+$ |
|---------|-----------|---------------------|-------------|----------|------------------|
| 35 | 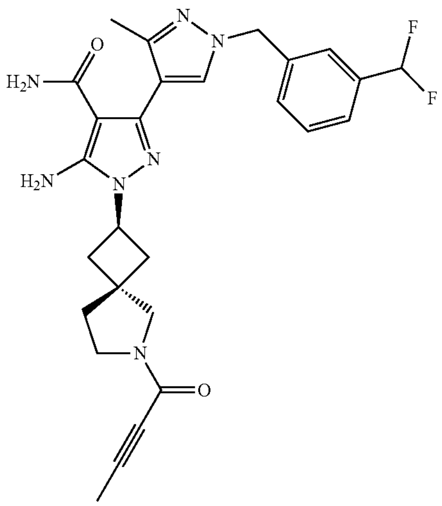 [SMILES: CC#CC(=O)N1CC[C@]2(C1)C[C@H](n1nc(-c3cn(Cc4cccc(C(F)F)c4)nc3C)c(C(N)=O)c1N)C2] | 0.9 | B | 0.724 | 522.3 |
| 36 | 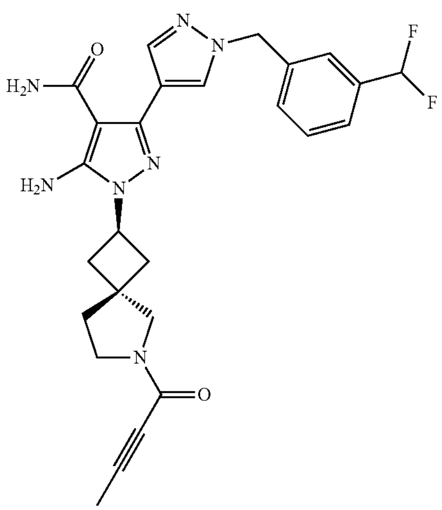 [SMILES: CC#CC(=O)N1CC[C@]2(C1)C[C@H](n1nc(-c3cnn(Cc4cccc(C(F)F)c4)c3)c(C(N)=O)c1N)C2] | 0.2 | B | 0.716 | 508.3 |
| 37 | 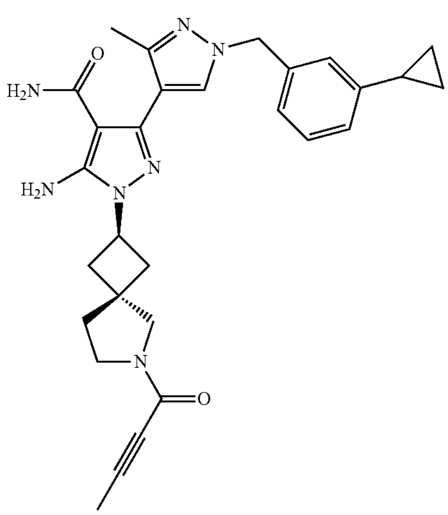 [SMILES: CC#CC(=O)N1CC[C@]2(C1)C[C@H](n1nc(-c3cn(Cc4cccc(C5CC5)c4)nc3C)c(C(N)=O)c1N)C2] | 0.8 | B | 0.788 | 512.3 |

TABLE I-continued

Biological and physical properties of representatives of the present invention

| Example | Structure | BTK IC$_{50}$ (nM) | HPLC Method | RT (min) | m/z [M + H]$^+$ |
|---|---|---|---|---|---|
| 38 | 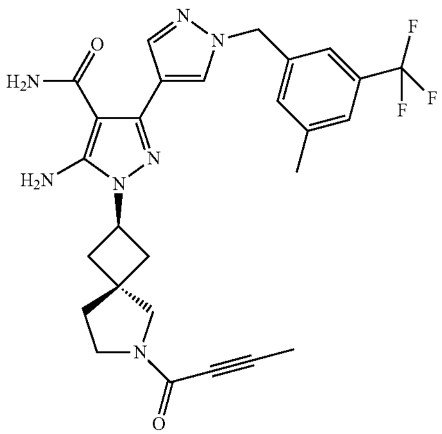 | 3.0 | A | 0.87 | 540.2 |
| 39 | 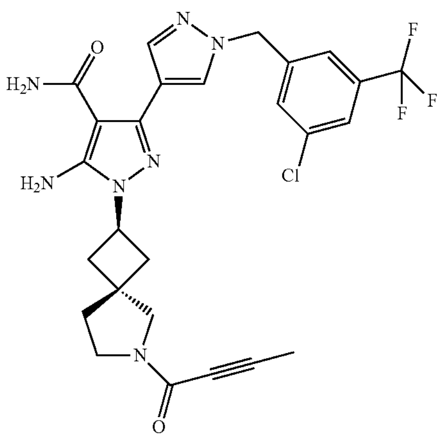 [SMILES: CC#CC(=O)N1CC[C@]2(C1)C[C@H](n1nc(-c3cnn(Cc4cc(Cl)cc(C(F)(F)F)c4)c3)c(C(N)=O)c1N)C2] | 0.9 | B | 0.758 | 560.3 |
| 40 | 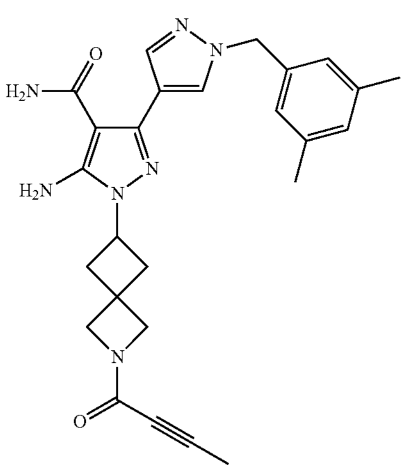 [SMILES: CC#CC(=O)N1CC2(CC(n3nc(-c4cnn(Cc5cc(C)cc(C)c5)c4)c(C(N)=O)c3N)C2)C1] | 4.2 | B | 0.722 | 472.4 |

TABLE I-continued

Biological and physical properties of representatives of the present invention

| Example | Structure | BTK IC$_{50}$ (nM) | HPLC Method | RT (min) | m/z [M + H]$^+$ |
|---|---|---|---|---|---|
| 41 | 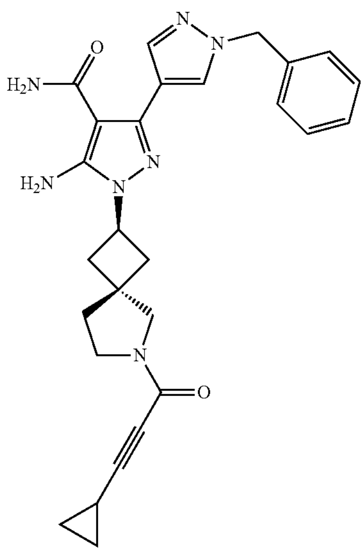 [SMILES: NC(=O)c1c(-c2cnn(Cc3ccccc3)c2)nn([C@H]2C[C@@]3(CCN(C(=O)C#CC4CC4)C3)C2)c1N] | 0.3 | B | 0.734 | 484.3 |
| 42 | 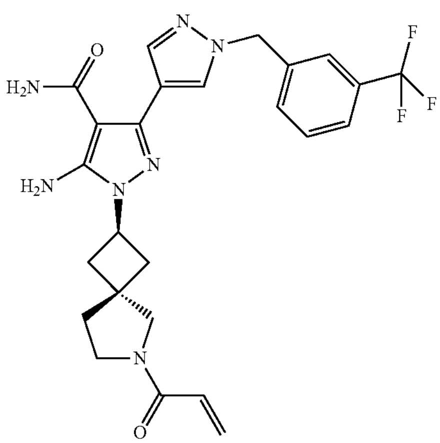 [SMILES: C=CC(=O)N1CC[C@]2(C1)C[C@H](n1nc(-c3cnn(Cc4cccc(C(F)(F)F)c4)c3)c(C(N)=O)c1N)C2] | 78 | B | 0.716 | 514.4 |
| 43 | 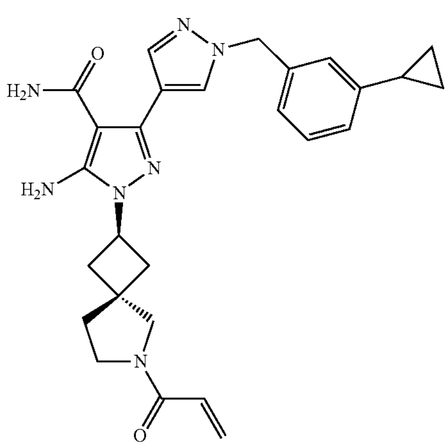 [SMILES: C=CC(=O)N1CC[C@]2(C1)C[C@H](n1nc(-c3cnn(Cc4cccc(C5CC5)c4)c3)c(C(N)=O)c1N)C2] | 3.0 | B | 0.722 | 486.4 |

TABLE I-continued

Biological and physical properties of representatives of the present invention

| Example | Structure | BTK IC$_{50}$ (nM) | HPLC Method | RT (min) | m/z [M + H]$^+$ |
|---|---|---|---|---|---|
| 44 | 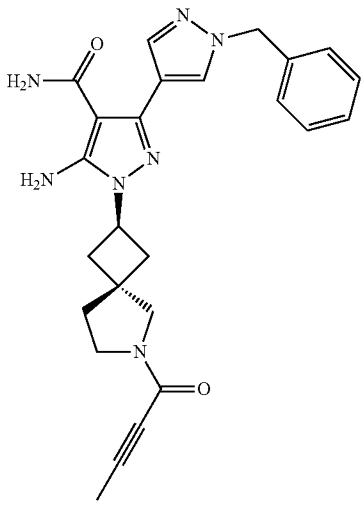 [SMILES: CC#CC(=O)N1CC[C@]2(C1)C[C@H](n1nc(-c3cnn(Cc4ccccc4)c3)c(C(N)=O)c1N)C2] | 0.3 | B | 0.672 | 458.3 |
| 45 | 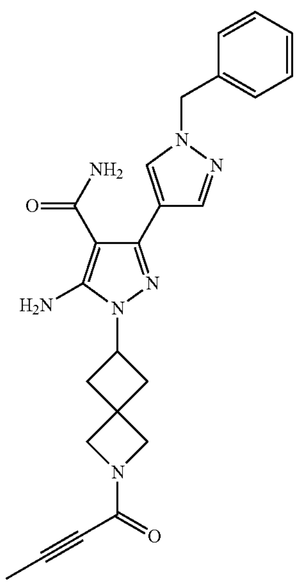 [SMILES: CC#CC(=O)N1CC2(CC(n3nc(-c4cnn(Cc5ccccc5)c4)c(C(N)=O)c3N)C2)C1] | 6.0 | A | 0.64 | 444.3 |
| 46 | 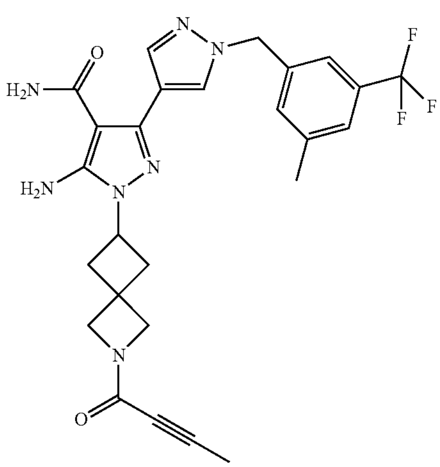 [SMILES: CC#CC(=O)N1CC2(CC(n3nc(-c4cnn(Cc5cc(C)cc(C(F)(F)F)c5)c4)c(C(N)=O)c3N)C2)C1] | 7.9 | B | 0.761 | 526.3 |

TABLE I-continued

Biological and physical properties of representatives of the present invention

| Example | Structure | BTK IC$_{50}$ (nM) | HPLC Method | RT (min) | m/z [M + H]$^+$ |
|---------|-----------|--------------------|-------------|----------|------------------|
| 47 | 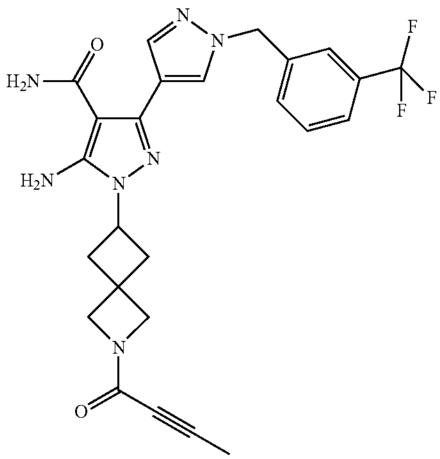 [SMILES: CC#CC(=O)N1CC2(CC(n3nc(-c4cnn(Cc5cccc(C(F)(F)F)c5)c4)c(C(N)=O)c3N)C2)C1] | 0.5 | A | 0.78 | 512.3 |
| 48 | 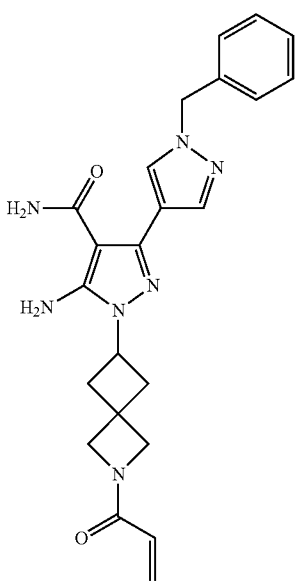 [SMILES: C=CC(=O)N1CC2(CC(n3nc(-c4cnn(Cc5ccccc5)c4)c(C(N)=O)c3N)C2)C1] | 16 | A | 0.59 | 432.3 |
| 49 | 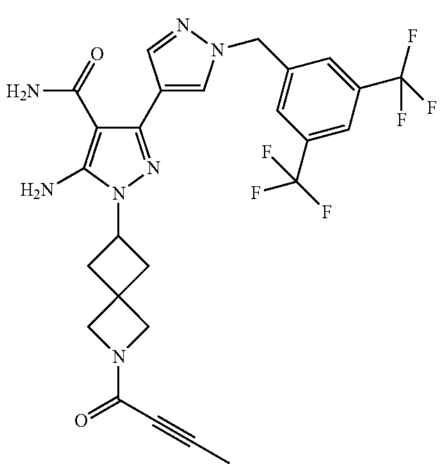 [SMILES: CC#CC(=O)N1CC2(CC(n3nc(-c4cnn(Cc5cc(C(F)(F)F)cc(C(F)(F)F)c5)c4)c(C(N)=O)c3N)C2)C1] | 45 | B | 0.802 | 580.3 |

TABLE I-continued
Biological and physical properties of representatives of the present invention
| Example | Structure | BTK IC$_{50}$ (nM) | HPLC Method | RT (min) | m/z [M + H]$^+$ |
|---|---|---|---|---|---|
| 50 | 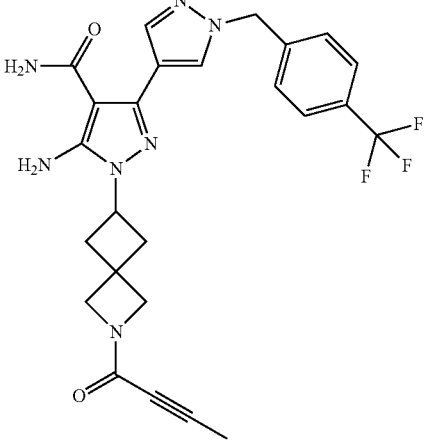 | 63 | B | 0.728 | 511.1 |
| 51 | 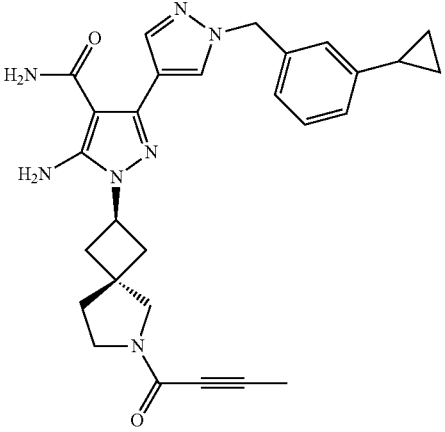 [SMILES: CC#CC(=O)N1CC[C@]2(C1)C[C@H](n1nc(-c3cnn(Cc4cccc(C5CC5)c4)c3)c(C(N)=O)c1N)C2] | 0.3 | B | 0.766 | 498.4 |
| 52 | 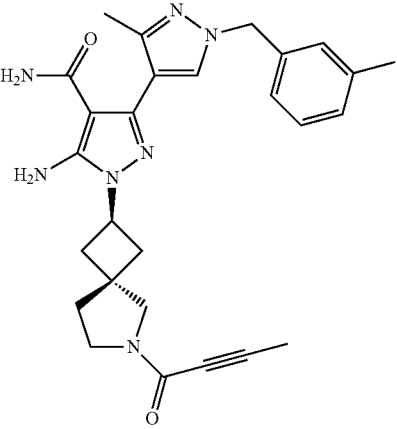 [SMILES: CC#CC(=O)N1CC[C@]2(C1)C[C@H](n1nc(-c3cn(Cc4cccc(C)c4)nc3C)c(C(N)=O)c1N)C2] | 1.2 | B | 0.7345 | 486.4 |

TABLE I-continued
Biological and physical properties of representatives of the present invention
| Example | Structure | BTK IC$_{50}$ (nM) | HPLC Method | RT (min) | m/z [M + H]$^+$ |
|---|---|---|---|---|---|
| 53 | 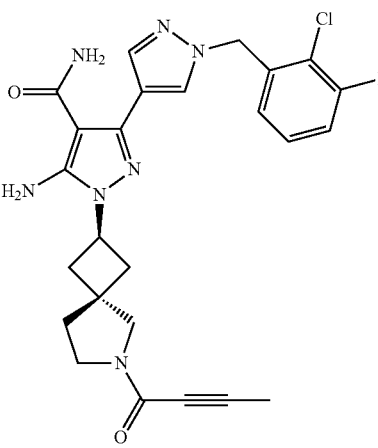 | 0.3 | B | 0.743 | 510.3 |
| 54 | 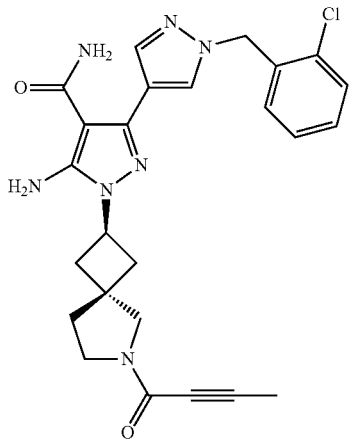 | 0.5 | B | 0.73 | 492.2 |
| 55 | 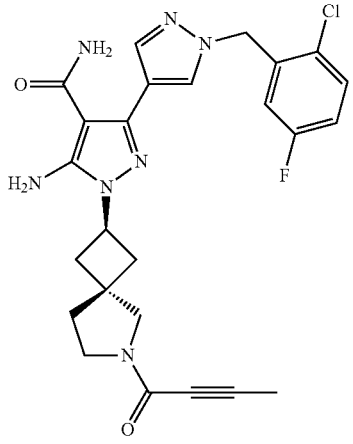 [SMILES: CC#CC(=O)N1CC[C@]2(C1)C[C@H](n1nc(-c3cnn(Cc4cc(F)ccc4Cl)c3)c(C(N)=O)c1N)C2] | 0.7 | B | 0.84 | 510.3 |

TABLE I-continued

Biological and physical properties of representatives of the present invention

| Example | Structure | BTK IC$_{50}$ (nM) | HPLC Method | RT (min) | m/z [M + H]$^+$ |
|---------|-----------|--------------------|-----------| ---------|-----------------|
| 56 | 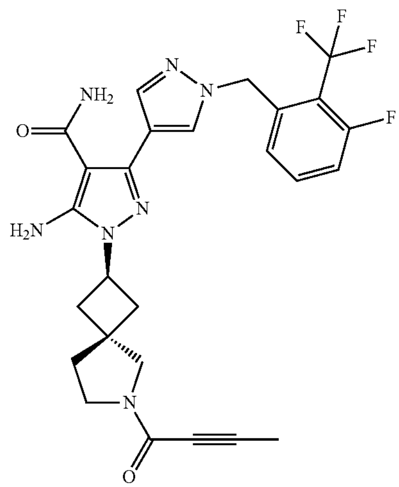 [SMILES: CC#CC(=O)N1CC[C@]2(C1)C[C@H](n1nc(-c3cnn(Cc4cccc(F)c4C(F)(F)F)c3)c(C(N)=O)c1N)C2] | 0.6 | B | 0.775 | 544.3 |
| 57 | 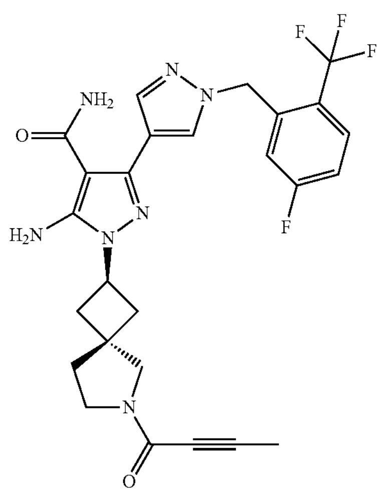 [SMILES: CC#CC(=O)N1CC[C@]2(C1)C[C@H](n1nc(-c3cnn(Cc4cc(F)ccc4C(F)(F)F)c3)c(C(N)=O)c1N)C2] | 0.9 | B | 0.778 | 544.3 |
| 58 | 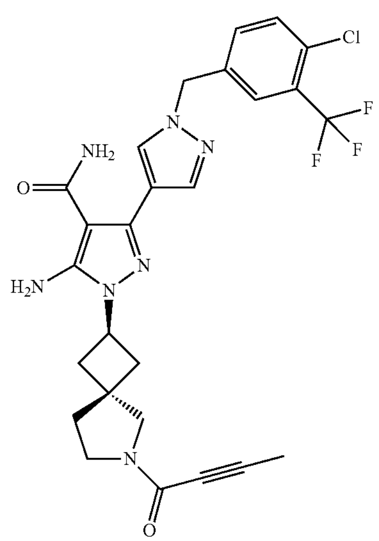 | 0.4 | B | 0.809 | 559.1 |

TABLE I-continued

Biological and physical properties of representatives of the present invention

| Example | Structure | BTK IC$_{50}$ (nM) | HPLC Method | RT (min) | m/z [M + H]$^+$ |
|---|---|---|---|---|---|
| 59 | 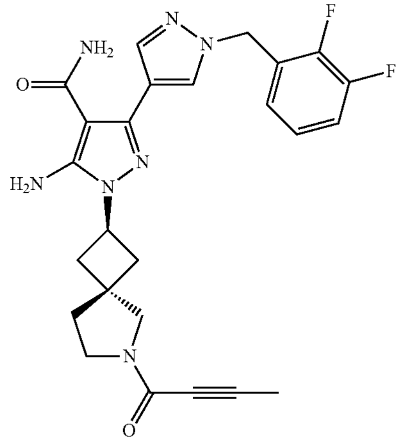 [SMILES: CC#CC(=O)N1CC[C@]2(C1)C[C@H](n1nc(-c3cnn(Cc4cccc(F)c4F)c3)c(C(N)=O)c1N)C2] | 0.3 | B | 0.707 | 494.2 |
| 60 | 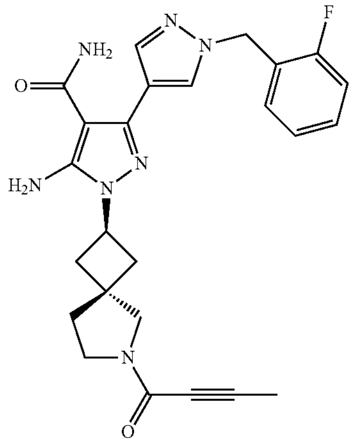 [SMILES: CC#CC(=O)N1CC[C@]2(C1)C[C@H](n1nc(-c3cnn(Cc4ccccc4F)c3)c(C(N)=O)c1N)C2] | 0.5 | B | 0.688 | 476.3 |

In a second generic embodiment, there is provided a pharmaceutical composition comprising a therapeutically effective amount of a compound according to the first embodiment or any of its related embodiments or a pharmaceutically acceptable salt thereof.

In a third generic embodiment, there is provided a method of treating a disease chosen from rheumatoid arthritis, systemic lupus erythromatosis, lupus nephritis, Sjogren's disease, vasculitis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis and uveitis, comprising administering to a patient a therapeutically effective amount of a compound according to the first embodiment or any of its related embodiments or a pharmaceutically acceptable salt thereof.

In a forth generic embodiment, there is provided a process for preparation of a compound according to the first embodiment or any of its related embodiments by:

(i) coupling a compound of formula A

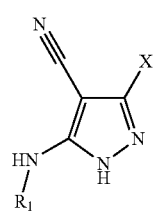

A with a compound of formula E

E to form a compound of formula G

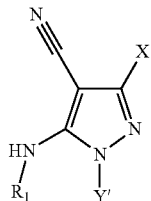

(G)

wherein each $R_1$ is independently chosen from hydrogen or methyl; X is a halogen (i.e. chloro, bromo, or iodo); LG is a leaving group; and Y' is $C_6$-$C_8$ spirocycle containing 1 ring nitrogen capped by a protecting group;

(ii) coupling the compound of formula (I-1) with a heterocyclic boronic ester or acid of formula C

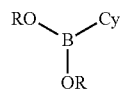

(C)

in presence of a suitable base and palladium catalyst followed by hydrolysis of the nitrile to carboxamide to form a compound of formula (II-1)

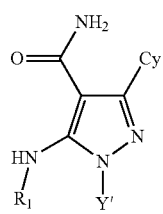

(II-1)

wherein each R group of the compound of formula C is H, alkyl, or both R groups are connected to form a ring;

Cy in the compound of formula (II-1) is chosen from

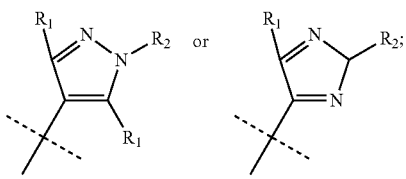

$R_2$ is L-Ar, wherein Ar is phenyl or pyridinyl and each is optionally substituted by one or more of halogen, halo $C_{1-4}$ alkyl, $C_{1-4}$ alkyl, $C_{1-4}$ alkoxy, —CN, halo $C_{1-4}$ alkoxy, or cycloalkyl;

L is —($CH_2$)— or —($CHCH_3$)—; and (iii) Deprotecting the capped nitrogen of the compound of formula (II-1) under an acidic condition and coupling the deprotected compound of formula (II-1) with a compound chosen from

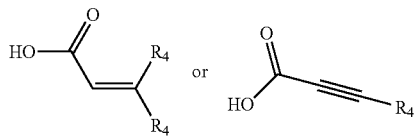

to form a compound of formula (I)

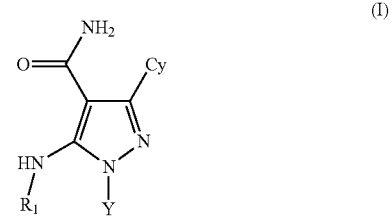

(I)

wherein Y is $C_6$-$C_8$ spirocycle containing 1 ring nitrogen bonded or covalently linked to $R_3$, wherein $R_3$ is

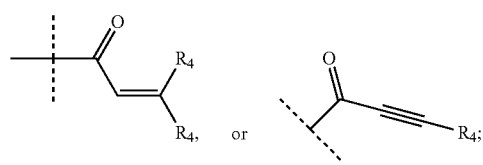

each $R_4$ is independently chosen from hydrogen, $C_{1-4}$ alkyl, or $C_{3-4}$ cycloalkyl;

or a pharmaceutically acceptable salt thereof.

BRIEF DESCRIPTION OF THE DRAWINGS

The accompanying drawing, which is included to provide further understanding of the subject technology and is incorporated in and constitute a part of this specification, illustrates aspects of the subject technology and together with the description serves to explain the principles of the subject technology.

FIG. 1 shows that the compounds of the present invention, e.g., Examples 12 and 22, elicit no effect on mean arterial pressure (MAP) in-vivo in comparison to the comparative compounds A-C (described in the example section).

DETAILED DESCRIPTION OF THE INVENTION

Definitions

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number, indicates that the chain or ring structure or combination of chain and ring structure as a whole, specified and mentioned in direct association, may consist of a maximum of y and a minimum of x carbon atoms.

Alkyl denotes monovalent, saturated hydrocarbon chains, which may be present in both straight-chain (unbranched)

and branched form. If an alkyl is substituted, the substitution may take place independently of one another, by mono- or polysubstitution in each case, on all the hydrogen-carrying carbon atoms.

For example, the term "$C_{1-5}$ alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl; —$CH_2C(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$ alkylamino or $C_{x-y}$ alkoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Alkenyl may optionally be present in the cis or trans or E or Z orientation with regard to the double bond(s).

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF=CF_2$, —$CCl=CH_2$, —$CBr=CH_2$, —$C\equiv C$—$CF_3$, —$CHFCH_2CH_3$, —$CHFCH_2CF_3$ etc.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl.

Corresponding groups are an example:

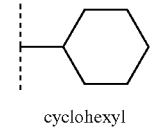

cyclohexyl

Spirocycle is a spiro-hydrocarbon ring one carbon atom (spiroatom) belongs to two rings together.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl and naphthyl.

The above definition of aryl also applies if aryl is part of another (combined) group as for example in arylamino, aryloxy or arylalkyl.

Heterocyclyl denotes ring systems, which are derived from the previously defined cycloalkyl or spirocycle by replacing one or more of the groups —$CH_2$— independently of one another in the hydrocarbon rings by the groups —O—, —S— or —NH—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO—, sulphone —SO$_2$—; nitrogen→N-oxide).

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuranyl, tetrahydropyranyl, piperidinyl, piperazinyl, pyrrolidinyl, morpholinyl, or the following heterocyclic spirocycles

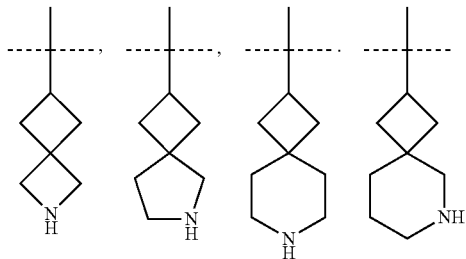

Heteroaryl denotes monocyclic heteroaromatic rings or polycyclic rings with at least one heteroaromatic ring, which compared with the corresponding aryl or cycloalkyl, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are pyridinyl, pyridazinyl, pyrimidinyl, pyrazinyl, benzoxazolyl, indolyl, isoindolyl, benzofuranyl, benzimidazolyl, benzothiazolyl, and the like.

Heteroatoms may optionally be present in all the possible oxidation stages (sulphur→sulphoxide —SO—, sulphone —SO$_2$—; nitrogen→N-oxide).

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl.

All cyclic and acyclic systems defined in this section hereinabove shall be understood to be optionally partially or fully halogenated where possible and unless otherwise indicated.

Stereochemistry/Solvates/Hydrates:

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. In general, the solvated forms such as hydrates are considered equivalent to the unsolvated forms for the purposes of the invention.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

Salts:

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulphonates, benzoates, besylates, bicarbonates, bitartrates, bromides/hydrobromides, Ca-edetates/edetates, camsylates, carbonates, chlorides/hydrochlorides, citrates, edisylates, ethane disulphonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulphonates, mesylates, methylbromides, methylnitrates, methylsulphates, mucates, napsylates, nitrates, oxalates, pamoates, pantothenates, phenyl acetates, phosphates/diphosphates, polygalacturonates, propionates, salicylates, stearates, subacetates, succinates, sulphamides, sulphates, tannates, tartrates, teoclates, toluenesulphonates, triethiodides, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetates), also comprise a part of the invention.

Some abbreviated notations and their structure correspondences are listed below:

In a representation such as for example

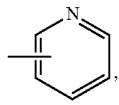

the solid line means that the ring system may be attached to the molecule via the carbon atom 1, 2 or 3, and is thus equivalent to the following representation

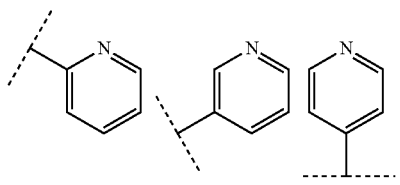

By a therapeutically effective amount for the purposes of this invention is meant a quantity of substance that is capable of obviating symptoms of illness or alleviating these symptoms, or which prolong the survival of a treated patient.

| List of abbreviations | |
|---|---|
| Ac | Acetyl |
| ACN | Acetonitrile |
| aq | Aqueous |
| Ar | Argon |
| ATP | adenosine triphosphate |
| Bn | Benzyl |
| Bu | Butyl |
| Boc | tert-butyloxycarbonyl |
| cat | Catalyst |
| conc | concentrated |
| d | day(s) |
| DCM | Dichloromethane |
| DIPEA | N,N-diisopropylethylamine |
| DMAP | 4-N,N-dimethylaminopyridine |
| DMA | Dimethylacetamide |
| DME | 1,2-dimethoxyethane |
| DMF | N,N-dimethylformamide |
| DMSO | Dimethylsulphoxide |
| dppf | 1.1'-bis(diphenylphosphino)ferrocene |
| EDC | 1-Ethyl-3-(3-dimethylaminopropyl)carbodiimide |
| ESI | electron spray ionization |
| Et | Ethyl |
| $Et_2O$ | diethyl ether |
| EtOAc | ethyl acetate |
| EtOH | Ethanol |
| h | hour(s) |
| HATU | O-(7-azabenzotriazol-1-yl)-N,N,N',N'-tetramethyl-uronium hexafluorophosphate |
| Hep | Heptane |
| HPLC | high performance liquid chromatography |
| i | Iso |
| IPAc | Isopropyl acetate |
| LC | liquid chromatography |
| LiHMDS | lithium bis(trimethylsilyl)amide |
| sln. | Solution |

| List of abbreviations -continued | |
|---|---|
| mCPBA | 3-Chloroperoxbenzoic acid |
| Me | Methyl |
| MeOH | Methanol |
| min | Minutes |
| MPLC | medium pressure liquid chromatography |
| MS | mass spectrometry |
| m/z | mass-to-charge ratio |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | Phenyl |
| Pr | Propyl |
| Pyr | Pyridine |
| rac | Racemic |
| Rf ($R_f$) | retention factor |
| RP | reversed phase |
| RT | Retention time (HPLC) |
| rt | ambient temperature |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | Triethylamine |
| temp. | Temperature |
| tert | Tertiary |
| Tf | Triflate |
| TFA | trifluoroacetic acid |
| THF | Tetrahydrofuran |
| TMS | Trimethylsilyl |
| TRIS | tris(hydroxymethyl)-aminomethane |
| Ts | p-Tosyl |
| TsOH | p-toluenesulphonic acid |
| UV | Ultraviolet |

Features and advantages of the present invention will become apparent from the following detailed examples which illustrate the fundamentals of the invention by way of example without restricting its scope:

Preparation of the Compounds According to the Invention

General Synthetic Methods

Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RHPLC). Discrete enantiomers may be obtained by resolution of racemic products using chiral HPLC. RHPLC purification methods used anywhere from 0-100% acetonitrile in water containing 0.1% formic acid, 0.1% TFA, or 2.5 mM ammonium bicarbonate and used one of the following columns:

a) Waters Sunfire OBD C18 5 μm 30×150 mm column b) Waters XBridge OBD C18 5 μm 30×150 mm column c) Waters ODB C8 5 μm 19×150 mm column d) Waters Atlantis ODB C18 5 μm 19×50 mm column e) Waters Atlantis T3 OBD 5 μm 30×100 mm column f) Phenomenex Gemini Axia C18 5 μm 30×100 mm column HPLC Methods:

TABLE 1

Analytical HPLC Method A

| Method | Mobile Phase A | Mobile Phase B | Gradient Time (min) | % A | % B | Flow (mL/min.) | Column |
|---|---|---|---|---|---|---|---|
| A | 0.05% Formic Acid in 95% water/5% ACN | 0.05% Formic Acid in ACN | 0<br>1.19<br>1.70 | 90.0<br>0<br>0 | 10.0<br>100<br>100 | 0.8 | CSH C18 2.1 × 50 mm, 1.7 μm particle diameter |

TABLE 2

Analytical HPLC Method B

| Method | Mobile Phase A | Mobile Phase B | Gradient Time (min) | % A | % B | Flow (mL/min.) | Column |
|---|---|---|---|---|---|---|---|
| A | 0.1% Formic Acid in Water | 0.1% Formic Acid in ACN | 0<br>1.0<br>1.3<br>1.4<br>1.7 | 95.0<br>5.0<br>5.0<br>95.0<br>95.0 | 5.0<br>95.0<br>95.0<br>5.0<br>5.0 | 0.8 | BEH 2.5 × 50 mm C18, 1.7 μm particle diameter |

TABLE 3

Analytical HPLC Method C

| Method | Mobile Phase A | Mobile Phase B | Gradient Time (min) | % A | % B | Flow (mL/min.) | Column |
|---|---|---|---|---|---|---|---|
| A | 0.05% Formic Acid in 95% water/5% ACN | 0.05% Formic Acid in ACN | 0<br>4.45<br>4.58 | 90.0<br>0<br>0 | 10.0<br>100<br>100 | 0.8 | CSH C18 2.1 × 50 mm, 1.7 μm particle diameter |

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Amide bond formations may be carried out by standard coupling conditions well-known in the art (e.g., Bodanszky, M. The Practice of Peptide Synthesis, Springer-Verlag, 1984, which is herein incorporated by reference in its entirety), such as reacting a carboxylic acid and an amine in the presence of a coupling reagents such as O-(7-azabenzotriazol-1-yl)-N,N,N',N'-tetramethyl-uronium hexafluorophosphate (HATU). Use of protective groups (i.e., protection or deprotection of a functional group) may be carried out by standard conditions well-known in the art (e.g., Greene, T. W.; Wuts, P. G. M. Protective Groups in Organic Synthesis, 3rd Ed. New York, Wiley, 1999, which is herein incorporated by reference in its entirety).

Compounds of formula I may be prepared as shown in Scheme I or II below.

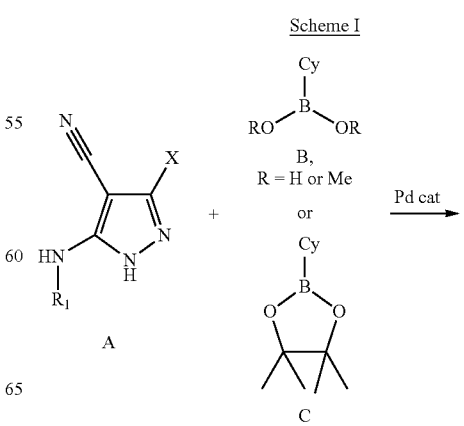

Scheme I

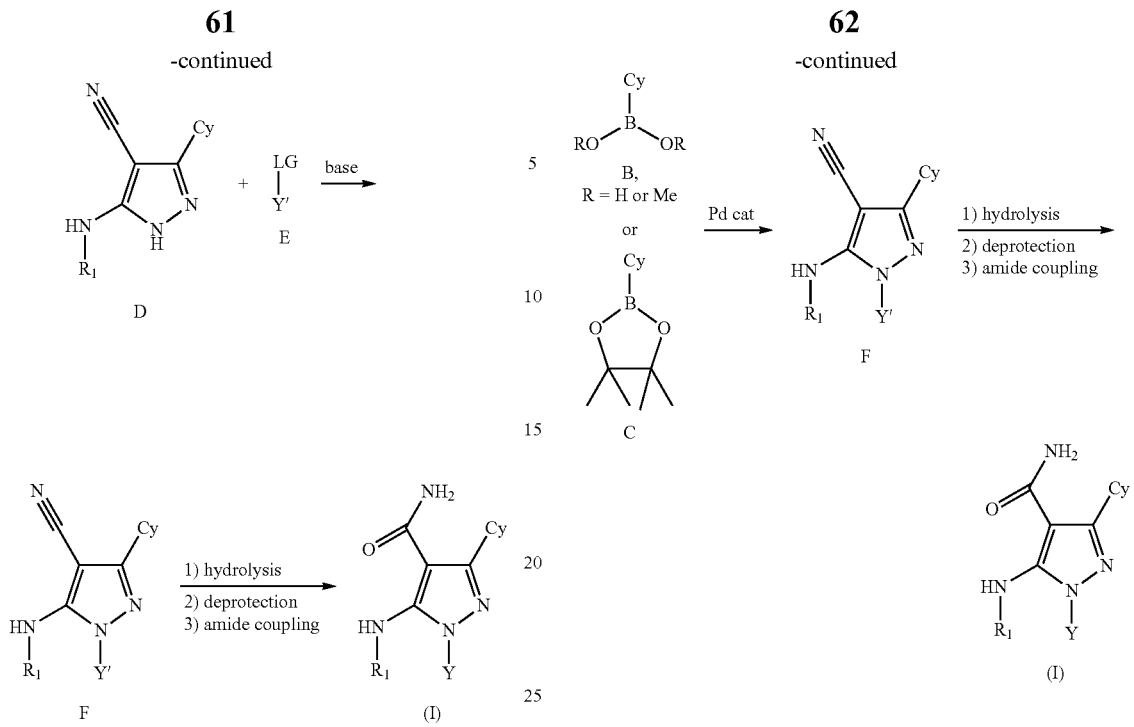

In Scheme I, a pyrazole of formula A, in which X may be bromo, chloro, or iodo, is reacted with a suitable boronic acid of formula B (R=H), a suitable boronic ester of formula B (R=methyl), or a suitable boronic ester of formula C under a palladium catalysed cross-coupling condition such as the presence of a suitable base (e.g., aqueous $Cs_2CO_3$, NaH), a suitable catalyst [e.g., tetrakis(triphenylphosphine)palladium(0)], in a suitable solvent (e.g., DME) and at a suitable temperature to provide a compound of formula D. The heterocycle D is reacted with a compound of formula E, wherein LG is a suitable leaving group (e.g., O-Ts), in a suitable solvent (e.g., DMA), in the presence of a suitable base (e.g., NaH) and at a suitable temperature to afford a compound of formula F. The nitrile F is hydrolysed to the corresponding carboxamide under a suitable condition such as in a suitable solvent or a mixture of solvents (e.g., a mixture of water and ethanol), in the presence of a suitable reagent such as (hydrido(dimethylphosphinous acid-KP)[hydrogen bis(dimethylphosphinito-KP)]platinum(II) and at a suitable temperature. The subsequent deprotection and amide coupling using conditions well-known in the art such as those described above provide a compound of formula (I).

Additionally, compounds of formula I may be prepared according to Scheme II.

Scheme II

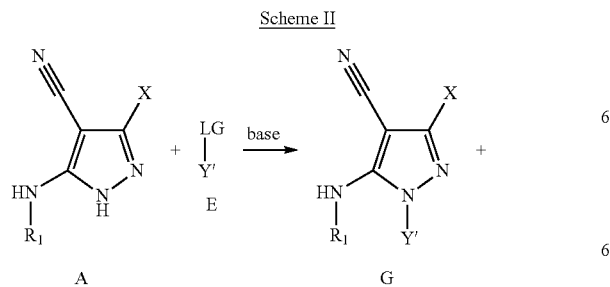

According to Scheme II, a pyrazole of formula A, in which X may be bromo, chloro, or iodo, may be reacted with a compound of formula E, wherein LG is a leaving group (e.g., O-Ts), in a suitable solvent (e.g., acetone), in the presence of a suitable base such (e.g., $Cs_2CO_3$, NaH) and at a suitable temperature to afford a heterocycle of formula G. The amino-pyrazole G may be reacted with a suitable boronic acid of formula B (R=H), a suitable boronic ester of formula B (R=methyl) or a suitable boronic ester of formula C under a palladium catalysed cross-coupling condition such as the presence of a suitable base (e.g., aqueous $K_2CO_3$), a suitable catalyst [e.g., tetrakis(triphenylphosphine)palladium(0)], in a suitable solvent (e.g., DME) and at a suitable temperature to generate a compound of formula F. The nitrile F may be converted to a compound of formula (I) according to the method described in Scheme I.

SYNTHETIC EXAMPLES

Method A
Synthesis of Intermediate I-1

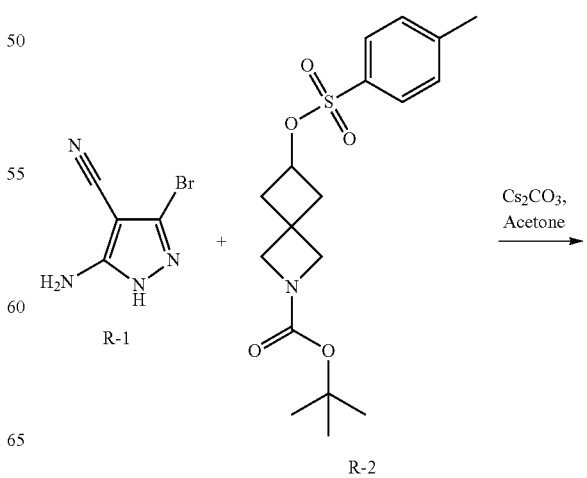

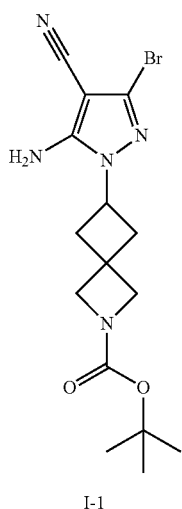

Cs$_2$CO$_3$ is added to a solution of the R-1 (22.0 g, 118 mmol) and R-2 (47.6 g, 129 mmol) in acetone (250 mL). The mixture is heated at 80° C. for 2 days. The mixture is diluted with water (200 mL) and extracted with CH$_2$Cl$_2$ (100 mL×2). The organics are then collected and concentrated to give I-1 (25 g), m/z=382.1 [M+H].

Method B
Synthesis of Intermediate I-2

Sodium hydride (14.3 g; 372.2 mmol) is added to a solution of the R-1 (58 g; 310.2 mmol) in DMA (460 mL). After 30 min, R-3 (130.2 g; 341.2 mmol) is added and heated at 80° C. for 18 h. The reaction is cooled to room temperature and diluted with MeOH (250 mL) and water (35 mL). The reaction is then stirred vigorously overnight. The heterogeneous mixture is vacuum filtered to yield, after drying, 96 g of a solid as a 1:1 mixture of pyrazole isomers. The solid is combined with 240 mL of CH$_2$Cl$_2$ and stirred vigorously overnight. The heterogeneous mixture is vacuum filtered and yielded 40 g of an off white solid. The solid is combined with 58 mL of CH$_2$Cl$_2$ and stirred vigorously. After 2 h, the heterogeneous solution is sonicated for 5 minutes and then cooled to 5° C. and stirred for 1 h. The heterogeneous solution is vacuum filtered and the solid is washed with cold CH$_2$Cl$_2$ (2×), collected and dried to yield I-2 (27.7 g). The combined filtrates are diluted with 180 mL of i-PrOH and stirred vigorously for 3 h. The heterogeneous solution is filtered and the solid is washed with a small amount of i-PrOH (2×). The filtrate is concentrated in vacuo to give a residue that is combined with 32 mL of CH$_2$Cl$_2$ and sonicated for 5 minutes. After an additional 1 h of stirring, the solution is cooled to 0° C. and stirred 1 h. The heterogeneous solution is filtered and solid collected and dried to yield additional amounts of I-2 (5.6 g). Total amount of I-2 isolated is 33.3 g, m/z 394.0/396.0 [M+H].

Method C
Synthesis of Intermediate I-3

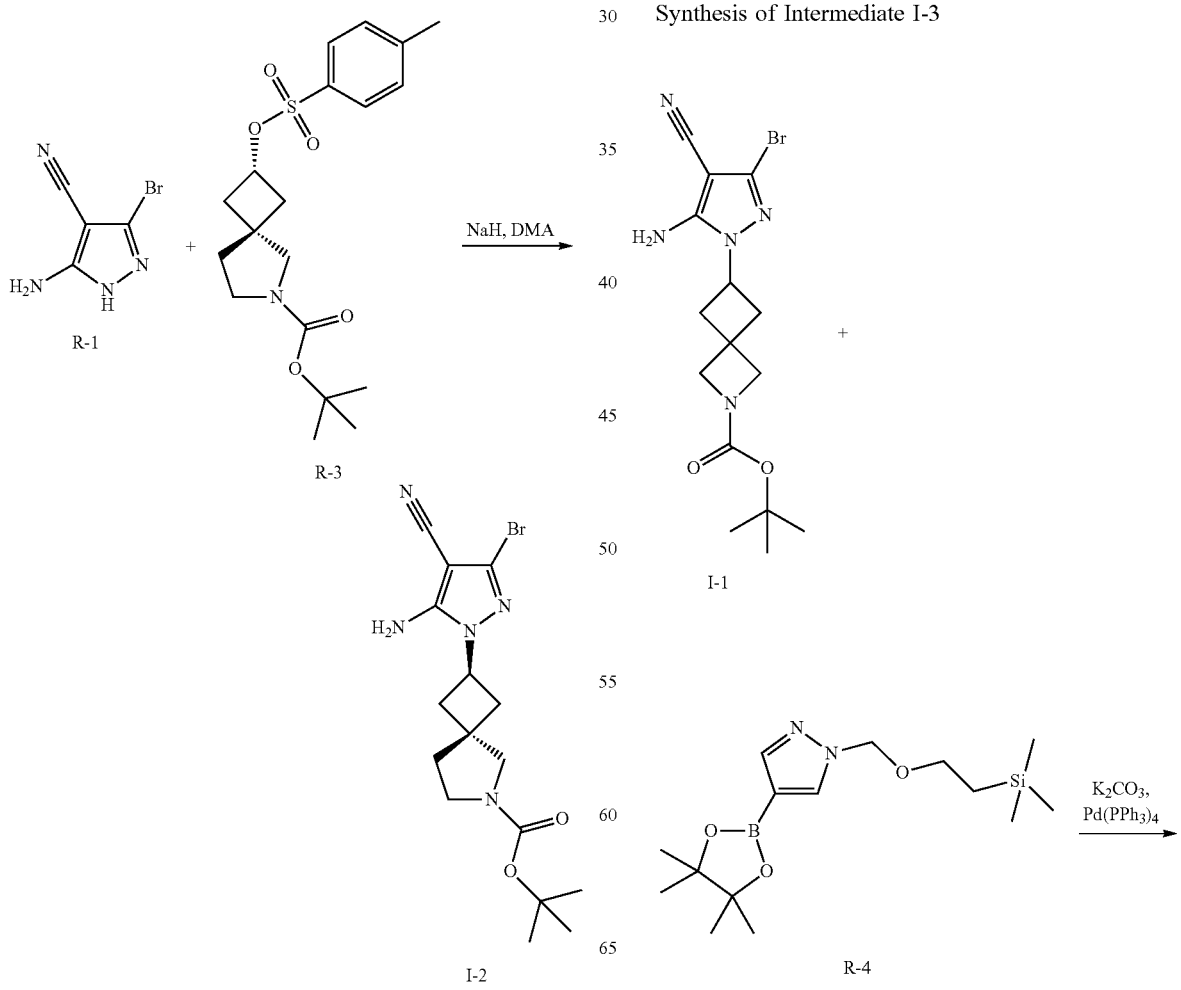

Method D

Synthesis of Intermediate I-5

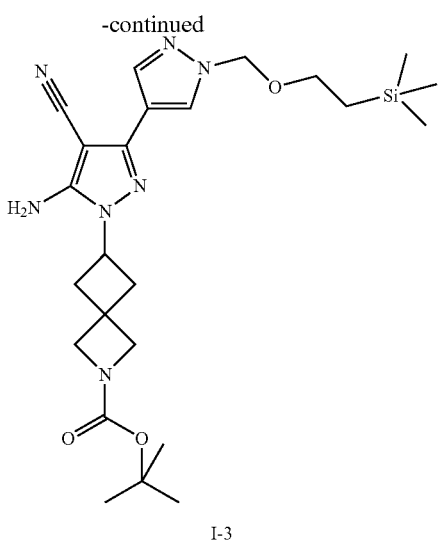

I-3

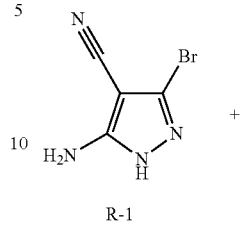

R-1

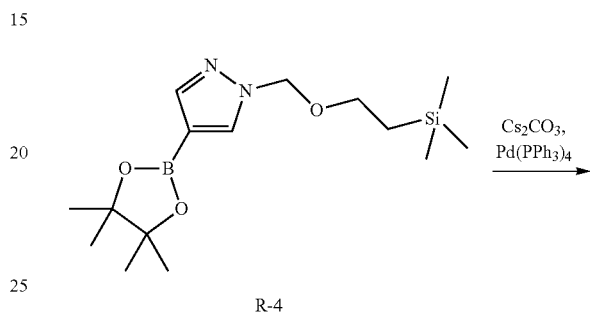

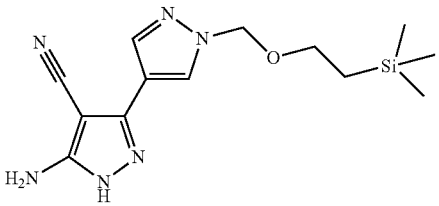

I-5

I-I (1.1 g, 2.9 mmol), R-4 (1.71 g, 3.2 mmol), 2M aqueous potassium carbonate (2.9 ml, 5.8 mmol), tetrakis(triphenylphosphine)palladium(0) (333 mg, 0.3 mmol) and DME (6 mL) are combined and sealed in a microwave tube and heated to 120° C. thermally overnight. The mixture is filtered, then diluted with water (100 mL) and extracted with EtOAc (4×200 mL). The combined EtOAc layers are dried over sodium sulfate and concentrated. The crude residue is purified by flash chromatography (SiO$_2$, 0-60% EtOAc/Heptane) to yield 1.2 g of I-3, m/z=500.5 [M+H].

The following intermediate is prepared in similar fashion:

| Structure | Intermediate | m/z |
|---|---|---|
| 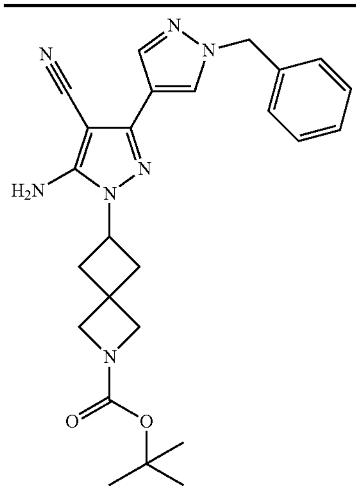 | I-4 | 460.7 [M + H] |

R-1 (2.0 g, 10.7 mmol), R-4 (6.4 g, 60%, 11.8 mmol), 2M aqueous Cs$_2$CO$_3$ (10.7 ml; 21 mmol), tetrakis(triphenylphosphine)palladium(0) (1.2 g; 1.1 mmol), and DME (6 mL) are combined in a microwave tube and heated to 135° C. in a microwave for 2 hours. The mixture is filtered, then diluted with water and extracted with EtOAc. The combined extracts are dried over sodium sulfate and concentrated to provide a crude residue that is purified by flash chromatography (0-100% EtOAc in heptane) to yield 3.2 g of I-5, m/z=382.1 [M+H].

The following intermediates are prepared in similar fashion:

| Structure | Intermediate | m/z |
|---|---|---|
| 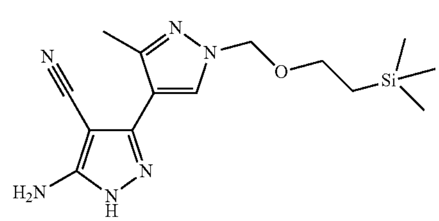 [SMILES: Cc1nn(COCC[Si](C)(C)C)cc1-c1n[nH]c(N)c1C#N] | I-6 | 319.1 [M + H] |

| Structure | Intermediate | m/z |
|---|---|---|
| 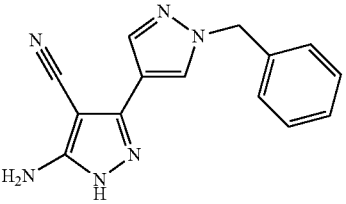 [SMILES: N#Cc1c(-c2cnn(Cc3ccccc3)c2)n[nH]c1N] | I-7 | 265.2 [M + H] |

Method E

Synthesis of Intermediate I-8

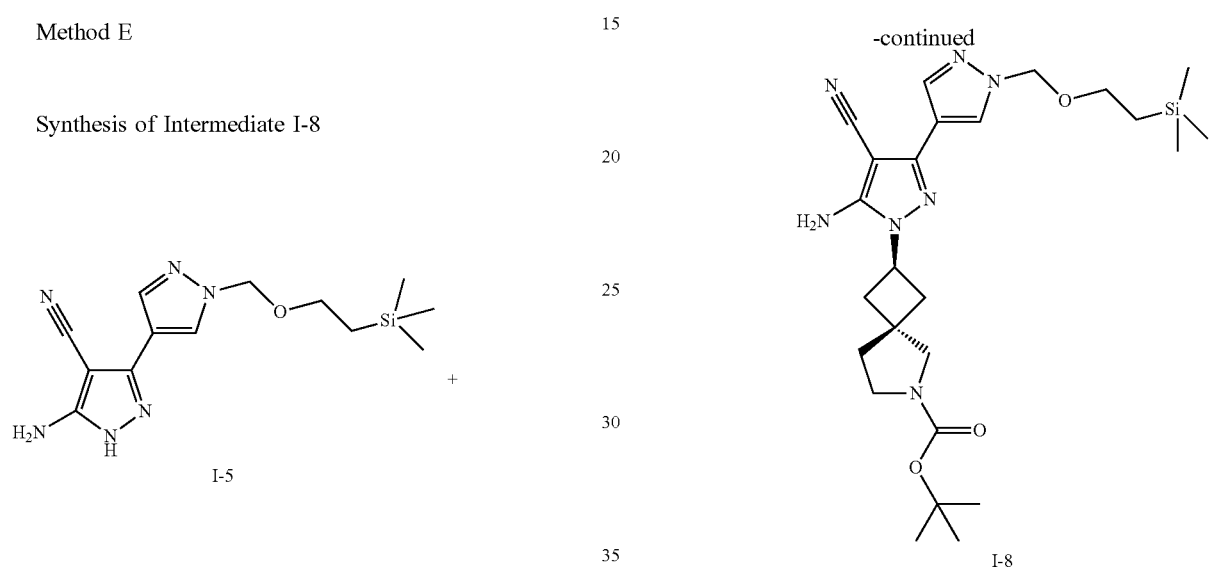

Sodium hydride (250 mg, 6.5 mmol) is added to a solution of I-5 (1.64 g, 5.4 mmol) in DMA (10 mL). After 5 min, R-3 (2.26 g, 5.9 mmol) is added and heated at 70° C. for 18 h. The mixture is diluted with water (20 mL) and extracted with EtOAc (4×10 mL). The combined EtOAc extracts are dried over sodium sulfate, filtrate and then concentrated in vacuo. The crude residue is purified by flash chromatography (SiO$_2$, 0-50% EtOAc in heptane) to provide 1.1 g of I-8, m/z=514.5 [M+H].

The following intermediate is prepared in similar fashion:

| Structure | Intermediate | m/z |
|---|---|---|
| 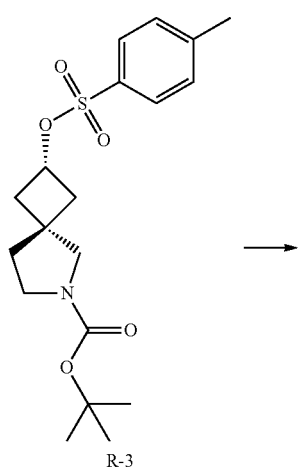 | I-9 | 528.3 [M + H] |

Method F
Synthesis of Intermediate I-10

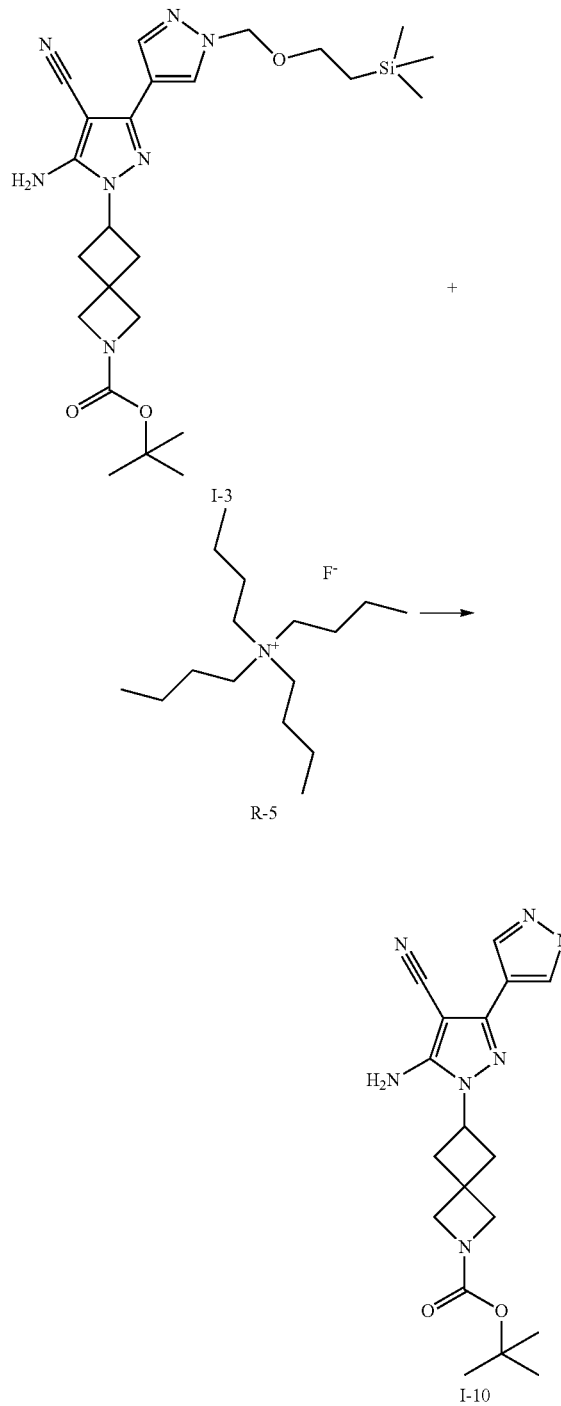

I-3 (845 mg, 1.7 mmol) is dissolved in THF (15 mL). A 1M solution of R-5 in THF (5.1 ml, 5.1 mmol) is added to the solution. The mixture is stirred at 70° C. overnight. The reaction solution is partitioned between saturated NH₄Cl (aq. solution) and EtOAc. The layers are separated and the organic layer is concentrated in vacuo. A small amount of CH₂Cl₂ is added to the residue and the resulting solid is filtered to yield 900 mg of I-10, m/z=370.3 [M+H].

The following intermediates are prepared in similar fashion:

| Structure | Intermediate | m/z |
|---|---|---|
| 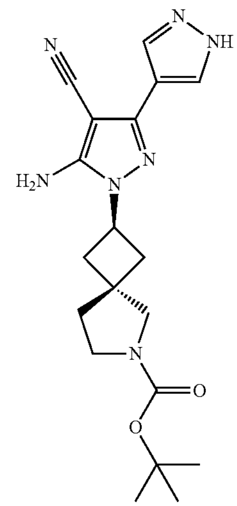 [SMILES: CC(C)(C)OC(=O)N1CC[C@]2(C1)C[C@H](n1nc(-c3cn[nH]c3)c(C#N)c1N)C2] | I-11 | 384.3 [M + H] |
| 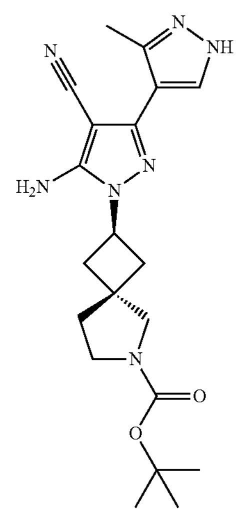 [SMILES: Cc1n[nH]cc1-c1nn([C@H]2C[C@@]3(CCN(C(=O)OC(C)(C)C)C3)C2)c(N)c1C#N] | I-12 | 398.2 [M + H] |

Method G
Synthesis of Intermediate I-13

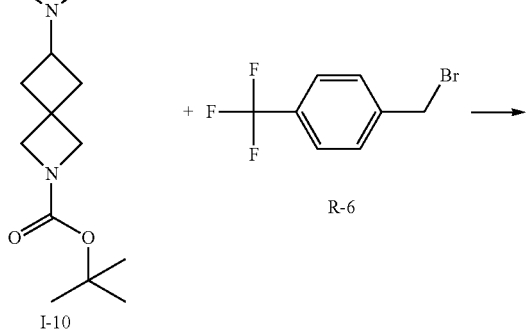

-continued

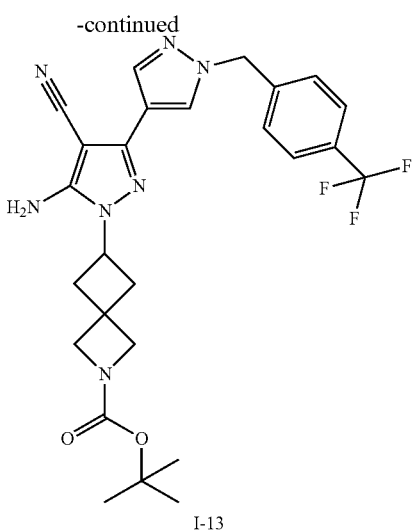

I-13

Potassium carbonate (270 mg, 1.94 mmol) is added to a solution of I-10 (143 mg, 0.39 mmol) in DMA (5 mL). After 5 min, R-6 (110 mg, 0.47 mmol) is added and the solution is heated to 70° C. for 18 h. The crude solution is loaded directly onto a silica column and purified (Gradient: 0-60% EtOAc in heptane) to yield 71 mg of I-13, m/z=528.4 [M+H].

The following intermediates are prepared in similar fashion:

| Structure | Intermediate | m/z |
|---|---|---|
| 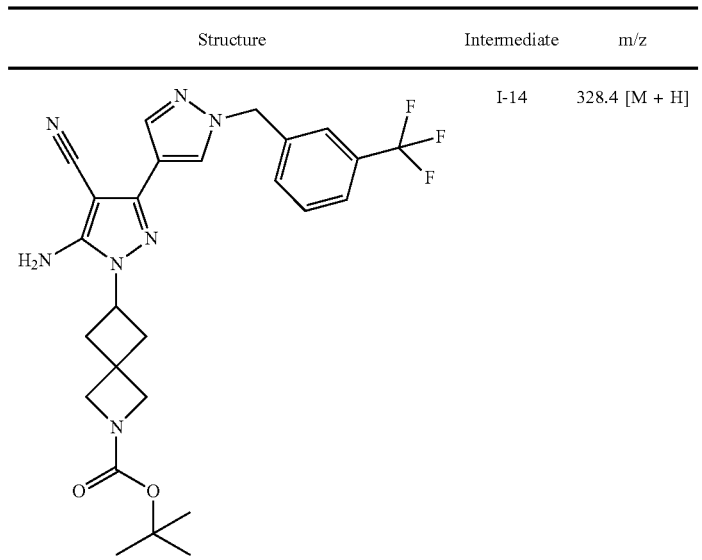 | I-14 | 328.4 [M + H] |
| 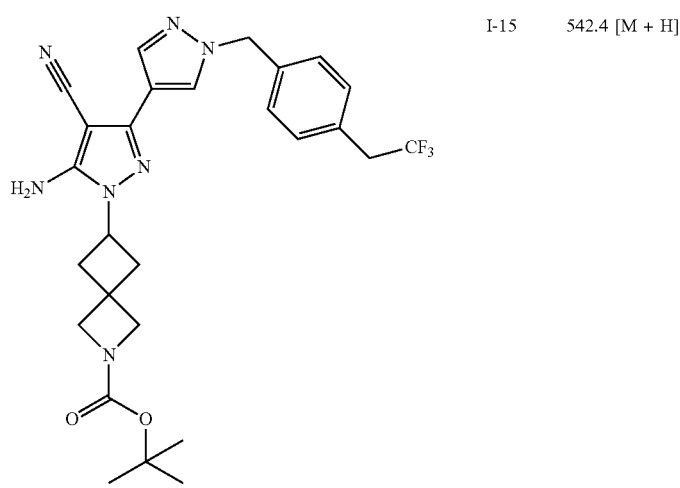 | I-15 | 542.4 [M + H] |

-continued

| Structure | Intermediate | m/z |
|---|---|---|
| 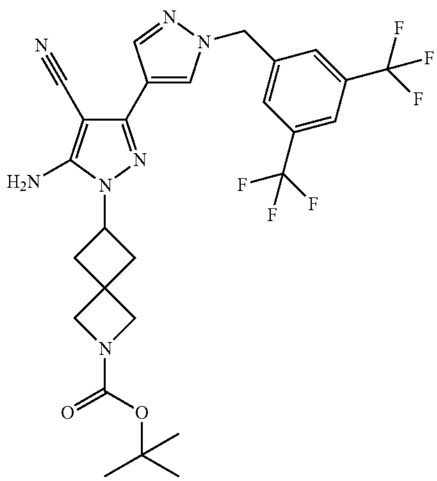 [SMILES: CC(C)(C)OC(=O)N1CC2(CC(n3nc(-c4cnn(Cc5cc(C(F)(F)F)cc(C(F)(F)F)c5)c4)c(C#N)c3N)C2)C1] | I-16 | 596.4 [M + H] |
| 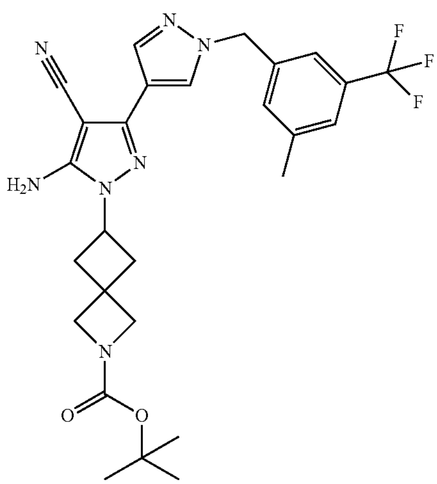 [SMILES: Cc1cc(Cn2cc(-c3nn(C4CC5(C4)CN(C(=O)OC(C)(C)C)C5)c(N)c3C#N)cn2)cc(C(F)(F)F)c1] | I-17 | 542.4 [M + H] |
| 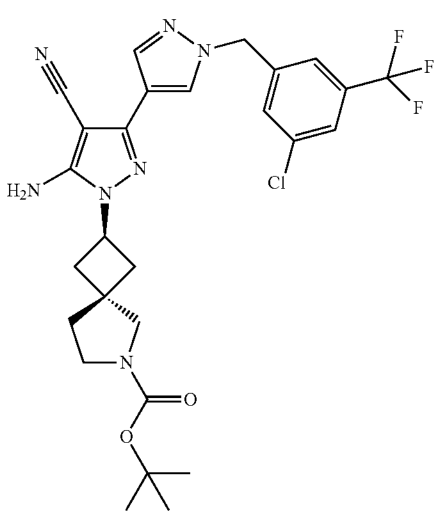 [SMILES: CC(C)(C)OC(=O)N1CC[C@]2(C1)C[C@H](n1nc(-c3cnn(Cc4cc(Cl)cc(C(F)(F)F)c4)c3)c(C#N)c1N)C2] | I-18 | 576.3 [M + H] |

-continued
| Structure | Intermediate | m/z |
|---|---|---|
| 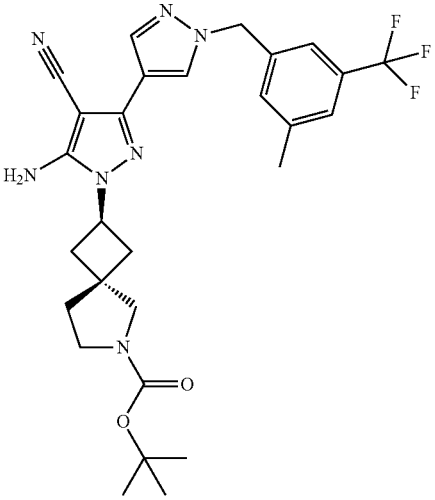 [SMILES: Cc1cc(Cn2cc(-c3nn([C@H]4C[C@@]5(CCN(C(=O)OC(C)(C)C)C5)C4)c(N)c3C#N)cn2)cc(C(F)(F)F)c1] | I-19 | 556.4 [M + H] |
| 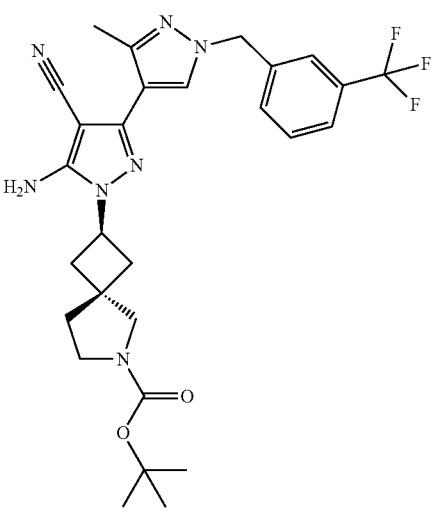 [SMILES: Cc1nn(Cc2cccc(C(F)(F)F)c2)cc1-c1nn([C@H]2C[C@@]3(CCN(C(=O)OC(C)(C)C)C3)C2)c(N)c1C#N] | I-20 | 556.3 [M + H] |
Method H
Synthesis of Intermediate I-21
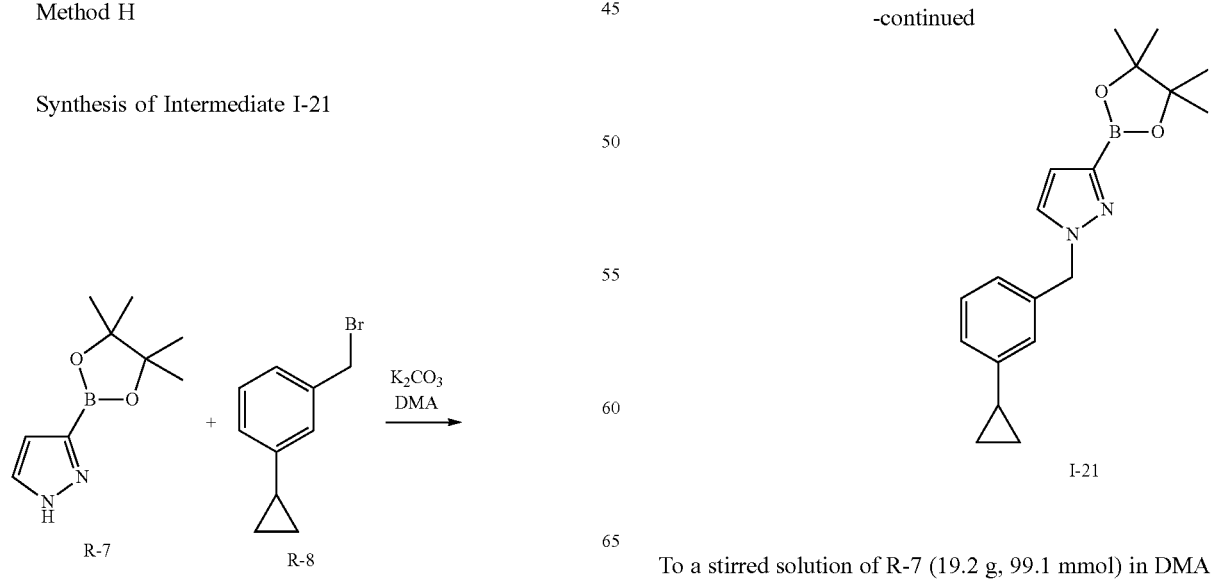
To a stirred solution of R-7 (19.2 g, 99.1 mmol) in DMA (54 mL) is added potassium carbonate (27.4 g, 198.1 mmol).

R-8 (23.0 g, 109 mmol) is then added slowly. The reaction is stirred at room temperature for 6 h. The reaction is then quenched with water and extracted with EtOAc. The EtOAc is concentrated in vacuo and residue is purified by flash chromatography (SiO$_2$, 10% EtOAc in hexanes) to yield 18 g of I-21, m/z=324.4 [M+H].

The following intermediates are prepared in similar fashion:

| Structure | Intermediate | m/z |
|---|---|---|
| 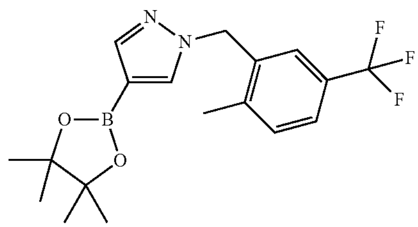 [SMILES: Cc1ccc(C(F)(F)F)cc1Cn1cc(B2OC(C)(C)C(C)(C)O2)cn1] | I-22 | 367.2 [M + H] |
| 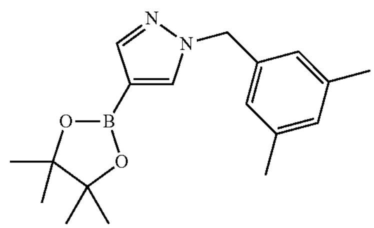 | I-23 | 313.6 [M + H] |
| 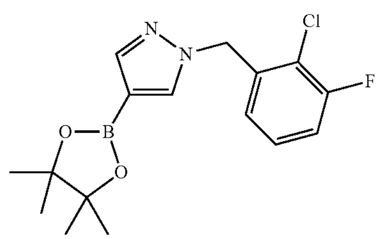 [SMILES: CC1(C)OB(c2cnn(Cc3cccc(F)c3Cl)c2)OC1(C)C] | I-24 | 337.1/339.2 [M + H] |
| 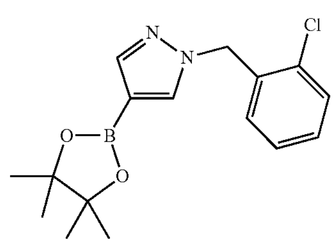 [SMILES: CC1(C)OB(c2cnn(Cc3ccccc3Cl)c2)OC1(C)C] | I-25 | 319.2/321.1 [M + H] |
| 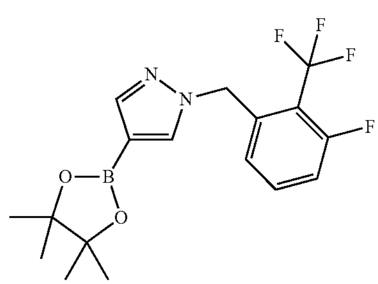 [SMILES: CC1(C)OB(c2cnn(Cc3cccc(F)c3C(F)(F)F)c2)OC1(C)C] | I-26 | 370.1/371.9 [M + H] |

-continued
| Structure | Intermediate | m/z |
|---|---|---|
| 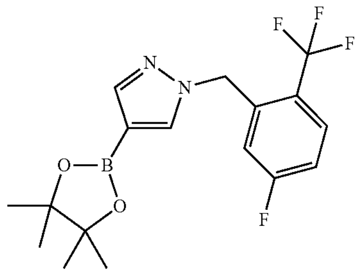 [SMILES: CC1(C)OB(c2cnn(Cc3cc(F)ccc3C(F)(F)F)c2)OC1(C)C] | I-27 | 370.3 [M + H] |
| 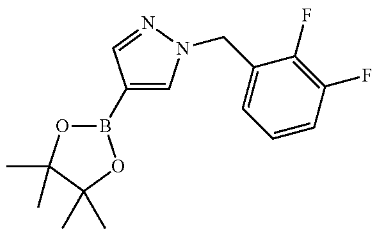 [SMILES: CC1(C)OB(c2cnn(Cc3cccc(F)c3F)c2)OC1(C)C] | I-28 | 321.4 [M + H] |
| 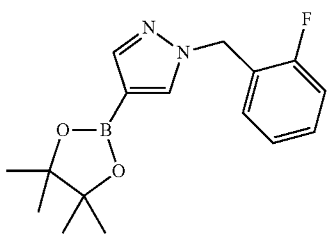 [SMILES: CC1(C)OB(c2cnn(Cc3ccccc3F)c2)OC1(C)C] | I-29 | 303.4 [M + H] |
| 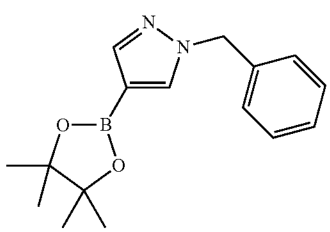 [SMILES: CC1(C)OB(c2cnn(Cc3ccccc3)c2)OC1(C)C] | I-30 | 286.0 [M + H] |
Method I
Synthesis of Intermediate I-31
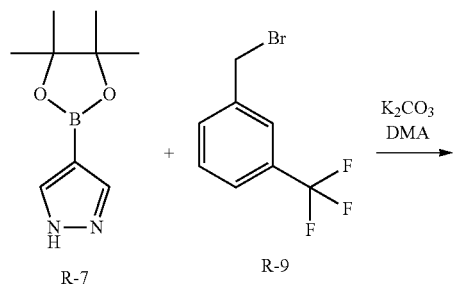
-continued
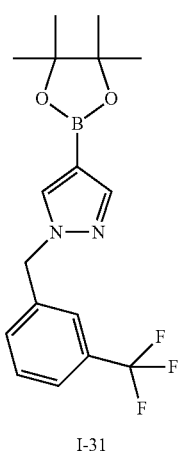
I-31
In a 1 L flask is placed R-7 (25 g, 128.8 mmol) and potassium carbonate (35.6 g, 257.7 mmol) in 100 ml of DMF. To this mixture is added R-9 (33.9 g, 141.7 mmol) and the reaction allowed to stir overnight. The reaction is then filtered and concentrated. The residue is dissolved in CH₂Cl₂ and filtered through Celite. The filtrate is concentrated to provide 45.4 g of I-31, m/z=353.4 [M+H]. Intermediate I-31 is used in subsequent steps without further purification.

The following intermediates are prepared in similar fashion:

| Structure | Intermediate | m/z |
|---|---|---|
| 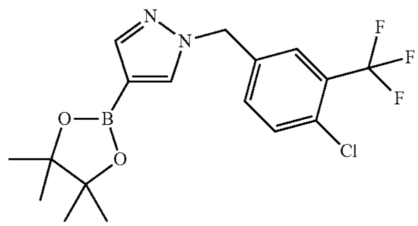 | I-32 | 367.1 [M + H] |
| 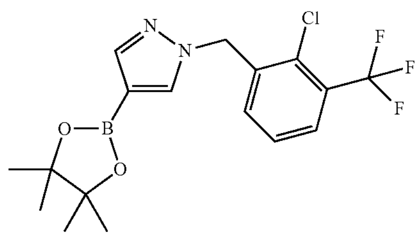 [SMILES: CC1(C)OB(c2cnn(Cc3cccc(C(F)(F)F)c3Cl)c2)OC1(C)C] | I-33 |  |
| 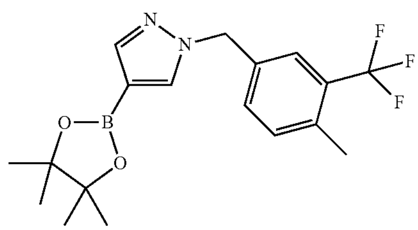 [SMILES: Cc1ccc(Cn2cc(B3OC(C)(C)C(C)(C)O3)cn2)cc1C(F)(F)F] | I-34 |  |
| 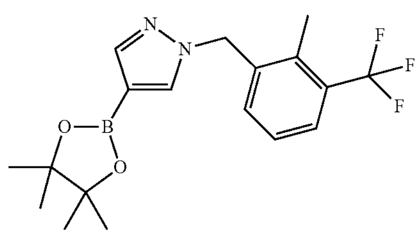 [SMILES: Cc1c(Cn2cc(B3OC(C)(C)C(C)(C)O3)cn2)cccc1C(F)(F)F] | I-35 | 367.2 [M + H] |
| 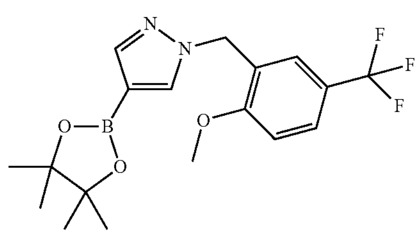 [SMILES: COc1ccc(C(F)(F)F)cc1Cn1cc(B2OC(C)(C)C(C)(C)O2)cn1] | I-36 | 383.1 [M + H] |
| 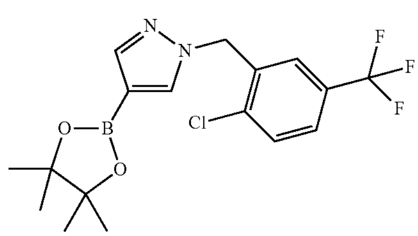 [SMILES: CC1(C)OB(c2cnn(Cc3cc(C(F)(F)F)ccc3Cl)c2)OC1(C)C] | I-37 | 387.1 [M + H] |

-continued

| Structure | Intermediate | m/z |
|---|---|---|
| 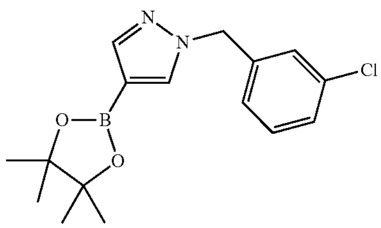 [SMILES: CC1(C)OB(c2cnn(Cc3cccc(Cl)c3)c2)OC1(C)C] | I-38 | 319.2 [M + H] |
| 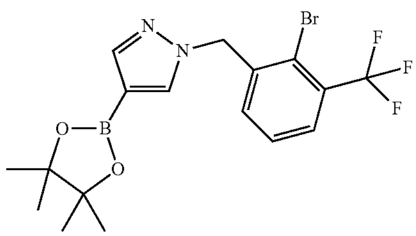 [SMILES: CC1(C)OB(c2cnn(Cc3cccc(C(F)(F)F)c3Br)c2)OC1(C)C] | I-39 | 431.1 [M + H] |
| 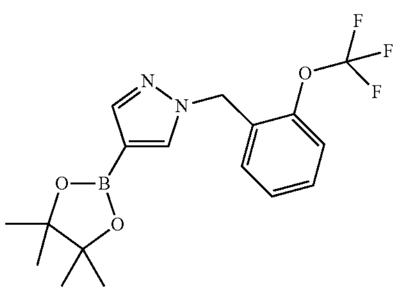 [SMILES: CC1(C)OB(c2cnn(Cc3ccccc3OC(F)(F)F)c2)OC1(C)C] | I-40 | 369.2 [M + H] |
| 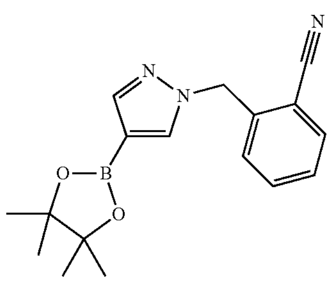 [SMILES: CC1(C)OB(c2cnn(Cc3ccccc3C#N)c2)OC1(C)C] | I-41 | 310.1 [M + H] |
| 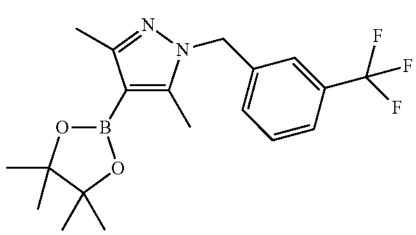 | I-42 | 377.7 [M + H] |
| 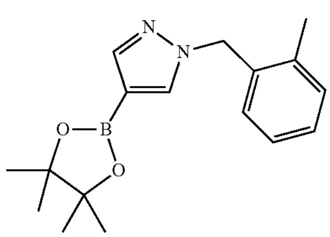 [SMILES: Cc1ccccc1Cn1cc(B2OC(C)(C)C(C)(C)O2)cn1] | I-43 | 300.5 [M + H] |

-continued

| Structure | Intermediate | m/z |
|---|---|---|
| 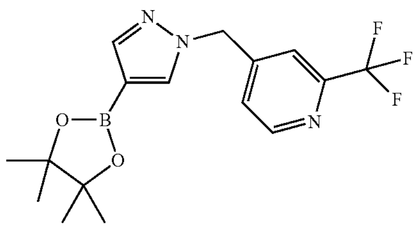 [SMILES: CC1(C)OB(c2cnn(Cc3ccnc(C(F)(F)F)c3)c2)OC1(C)C] | I-44 | 353.9 [M + H] |
| 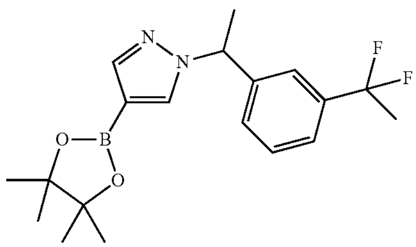 | I-45 | 367.3 [M + H] |
| 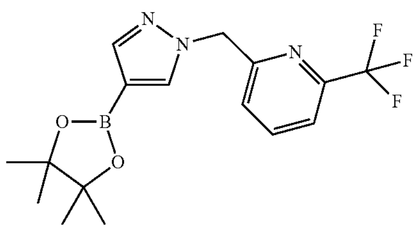 [SMILES: CC1(C)OB(c2cnn(Cc3cccc(C(F)(F)F)n3)c2)OC1(C)C] | I-46 | 354.3 [M + H] |
| 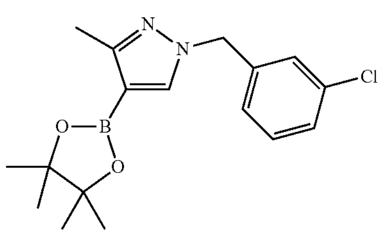 | I-47 | 330.0 [M + H] |
| 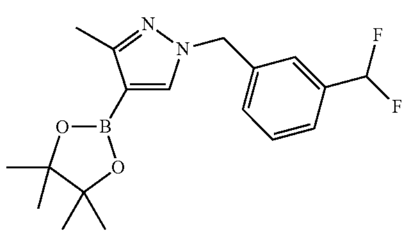 [SMILES: Cc1nn(Cc2cccc(C(F)F)c2)cc1B1OC(C)(C)C(C)(C)O1] | I-48 | 349.4 [M + H] |
| 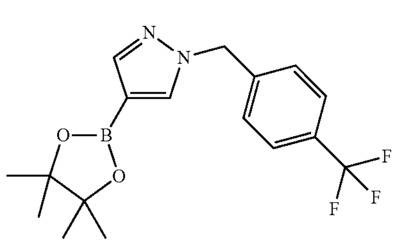 [SMILES: CC1(C)OB(c2cnn(Cc3ccc(C(F)(F)F)cc3)c2)OC1(C)C] | I-49 | 353.5 [M + H] |

| Structure | Intermediate | m/z |
|---|---|---|
| 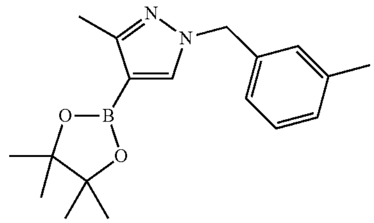 | I-50 | 313.1 [M + H] |
| 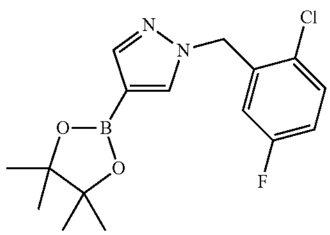 [SMILES: CC1(C)OB(c2cnn(Cc3cc(F)ccc3Cl)c2)OC1(C)C] | I-51 | 336.1/338.1 [M + H] |

Method J
Synthesis of Intermediate I-52

Method K
Synthesis of Mixture of Intermediates I-53

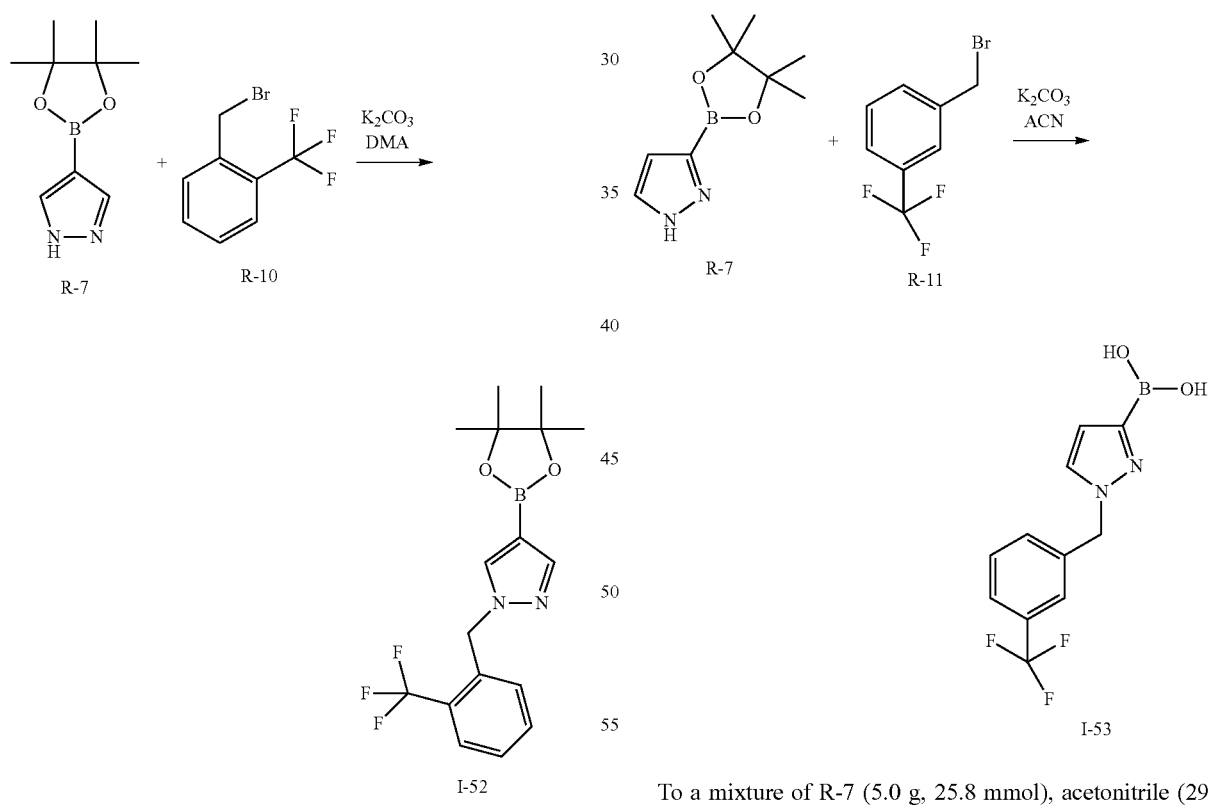

In a 1 L flask is placed R-7 (75 g, 386.5 mmol) and K$_2$CO$_3$ (106.7 g, 773 mmol) in 100 mL DMF. To this is added R-10 (101.6 g, 425.2 mmol) and the reaction allowed to stir overnight. The reaction is filtered and concentrated. The residue is dissolved in CH$_2$Cl$_2$ and filtered through Celite. The filtrate is concentrated to provide 136 g of I-52, m/z=353.0 [M+H]. Intermediate I-52 is used in subsequent steps without further purification.

To a mixture of R-7 (5.0 g, 25.8 mmol), acetonitrile (29 mL) and potassium carbonate (7.1 g, 51.5 mmol) is added R-11 (3.9 mL, 25.6 mmol). The mixture is stirred for 18 h under Ar. The reaction is then concentrated and the residue is partitioned between EtOAc and water. The layers are separated and the aqueous layer is extracted with EtOAc (2×). The combined organic layers are washed with brine, dried over MgSO$_4$, filtered and concentrated to yield 8.75 g of I-53, m/z=271.0 [M+H]. Intermediate I-53 mixture is used in subsequent steps without further purification.

The following intermediates are prepared in similar fashion:

| Structure | Intermediate | m/z |
|---|---|---|
| 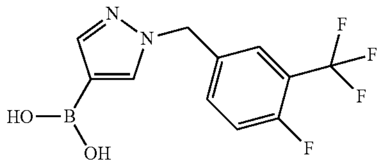 [SMILES: OB(O)c1cnn(Cc2ccc(F)c(C(F)(F)F)c2)c1] | I-54 | 289 [M + H] |
| 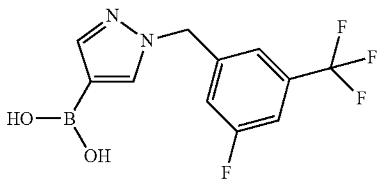 [SMILES: OB(O)c1cnn(Cc2cc(F)cc(C(F)(F)F)c2)c1] | I-55 | 289 [M + H] |
| 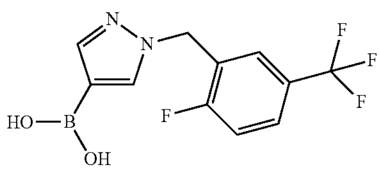 [SMILES: OB(O)c1cnn(Cc2cc(C(F)(F)F)ccc2F)c1] | I-56 | 289 [M + H] |
| 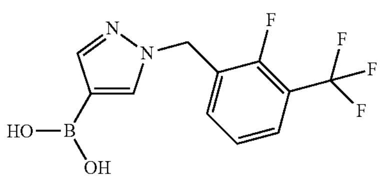 [SMILES: OB(O)c1cnn(Cc2cccc(C(F)(F)F)c2F)c1] | I-57 | 289 [M + H] |
| 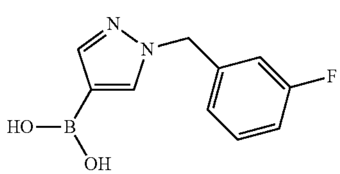 [SMILES: OB(O)c1cnn(Cc2cccc(F)c2)c1] | I-58 | 221 [M + H] |
| 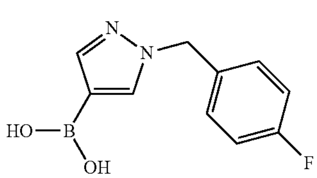 [SMILES: OB(O)c1cnn(Cc2ccc(F)cc2)c1] | I-59 | 221 [M + H] |

Method L
Synthesis of Intermediate I-60

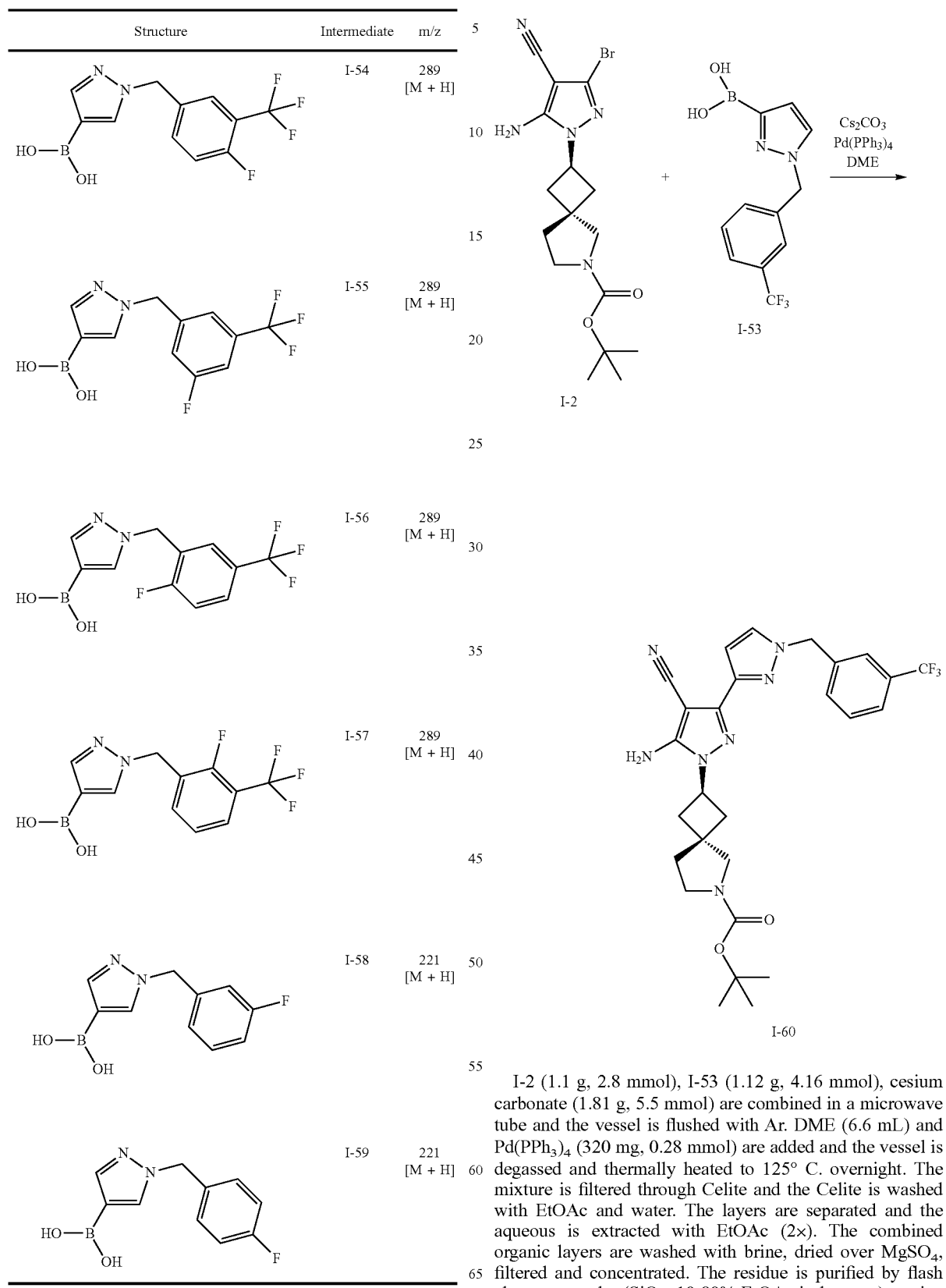

I-2 (1.1 g, 2.8 mmol), I-53 (1.12 g, 4.16 mmol), cesium carbonate (1.81 g, 5.5 mmol) are combined in a microwave tube and the vessel is flushed with Ar. DME (6.6 mL) and Pd(PPh$_3$)$_4$ (320 mg, 0.28 mmol) are added and the vessel is degassed and thermally heated to 125° C. overnight. The mixture is filtered through Celite and the Celite is washed with EtOAc and water. The layers are separated and the aqueous is extracted with EtOAc (2×). The combined organic layers are washed with brine, dried over MgSO$_4$, filtered and concentrated. The residue is purified by flash chromatography (SiO$_2$, 10-80% EtOAc in heptane) to give 407 mg of I-60, m/z=542.2 [M+H].

Method M
Synthesis of Intermediate I-61

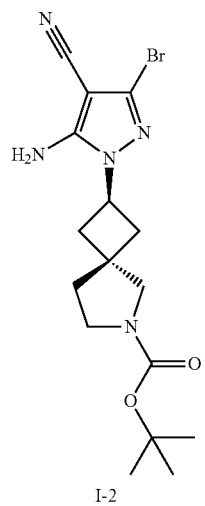
I-2

+

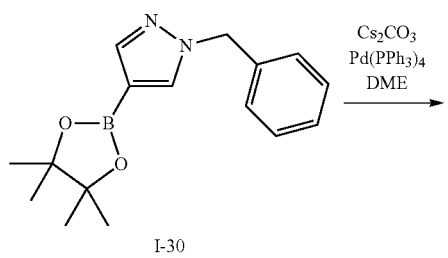
I-30

→ (Cs₂CO₃, Pd(PPh₃)₄, DME)

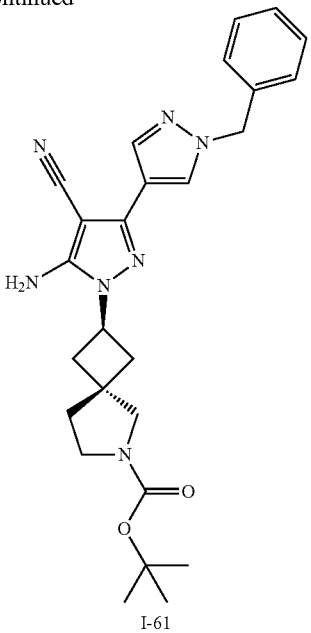
I-61

I-2 (1.0 g, 1.31 mmol), I-30 (790 mg, 2.8 mmol), cesium carbonate (1.6 g, 5.1 mmol), Pd(PPh₃)₄ (0.29 g, 0.25 mmol) and DME (6 mL) are combined in a microwave tube and heated thermally to 125° C. overnight. The mixture is filtered, then diluted with water (30 mL) and extracted with EtOAc (4×30 mL). The combined organic extracts are dried over sodium sulfate, filtered and concentrated to provide the crude residue. The crude material is purified via flash chromatography (SiO₂, 0-100% EtOAc in heptane) to yield 1.1 g of I-61, m/z=474.3 [M+H].

The following intermediates are prepared in similar fashion:

| Structure | Intermediate | m/z |
|---|---|---|
| 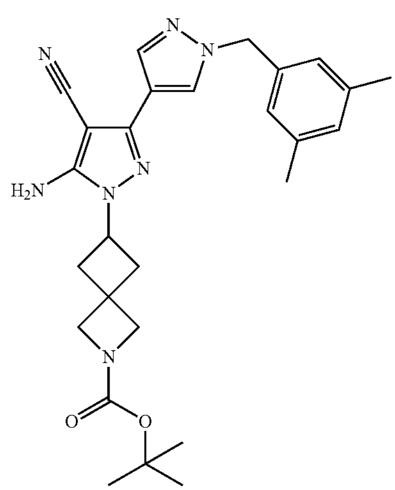 [SMILES: Cc1cc(C)cc(Cn2cc(-c3nn(C4CC5(C4)CN(C(=O)OC(C)(C)C)C5)c(N)c3C#N)cn2)c1] | I-62 | 488.5 [M + H] |

-continued

| Structure | Intermediate | m/z |
|---|---|---|
| 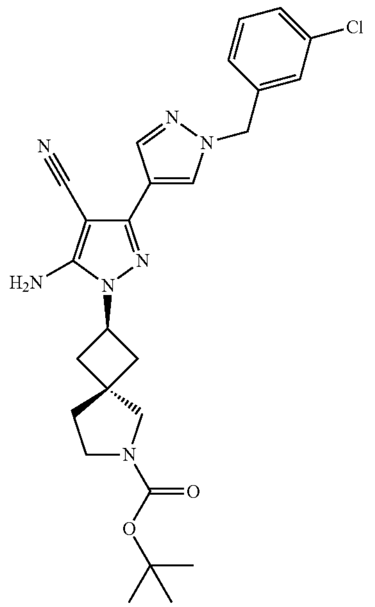 [SMILES: CC(C)(C)OC(=O)N1CC[C@]2(C1)C[C@H](n1nc(-c3cnn(Cc4cccc(Cl)c4)c3)c(C#N)c1N)C2] | I-63 | 508.2/510.2 [M + H] |
| 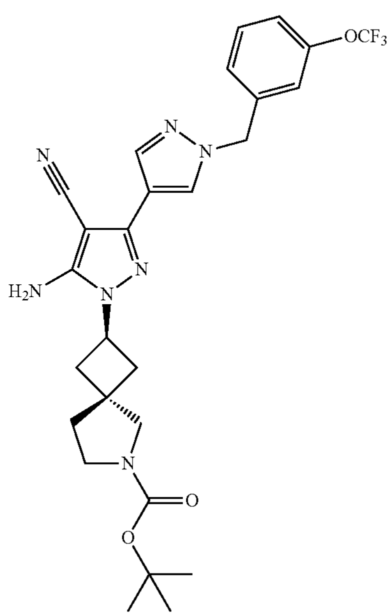 [SMILES: CC(C)(C)OC(=O)N1CC[C@]2(C1)C[C@H](n1nc(-c3cnn(Cc4cccc(OC(F)(F)F)c4)c3)c(C#N)c1N)C2] | I-64 | 558.4 [M + H] |

-continued
| Structure | Intermediate | m/z |
|---|---|---|
| 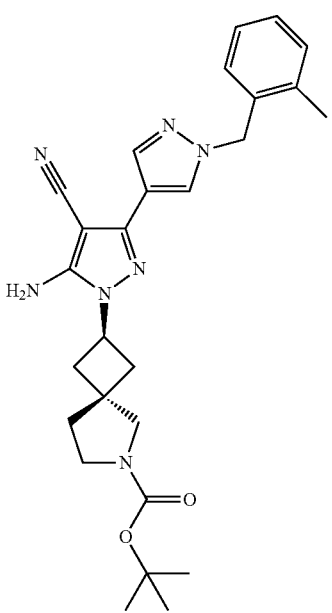 [SMILES: Cc1ccccc1Cn1cc(-c2nn([C@H]3C[C@@]4(CCN(C(=O)OC(C)(C)C)C4)C3)c(N)c2C#N)cn1] | I-65 | 488.4 [M + H] |
| 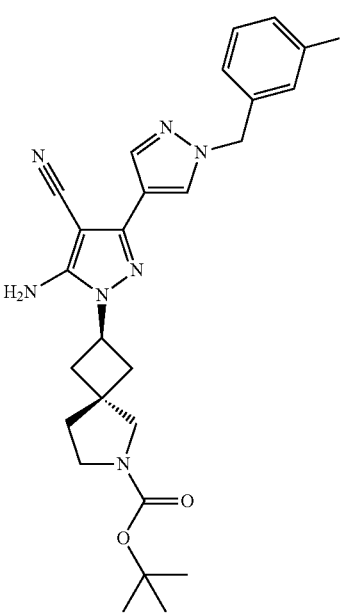 | I-66 | 492.0 [M + H] |

-continued
| Structure | Intermediate | m/z |
|---|---|---|
| 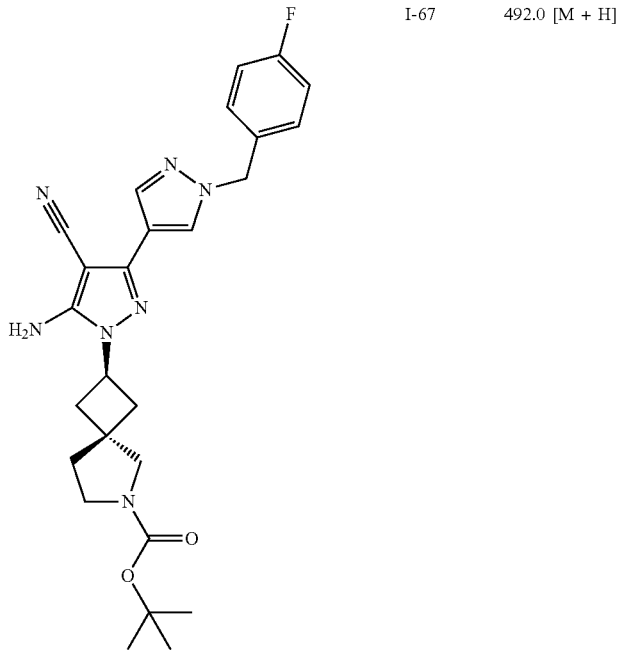 | I-67 | 492.0 [M + H] |
| 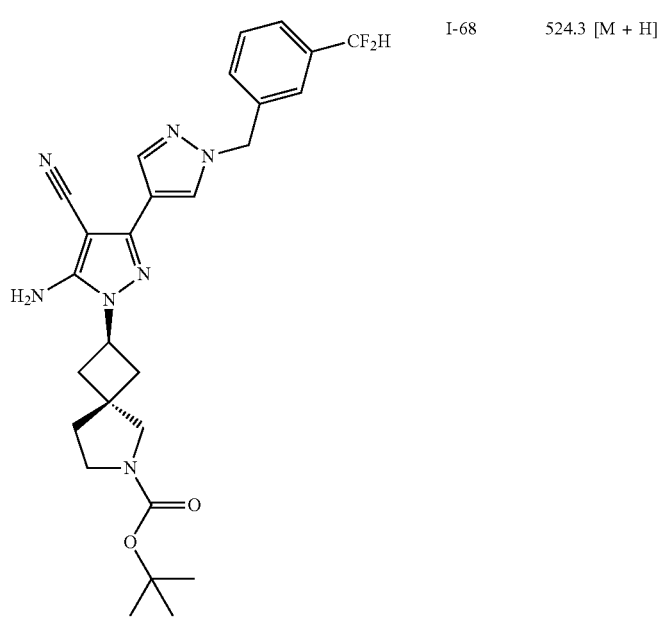 | I-68 | 524.3 [M + H] |

| Structure | Intermediate | m/z |
|---|---|---|
| 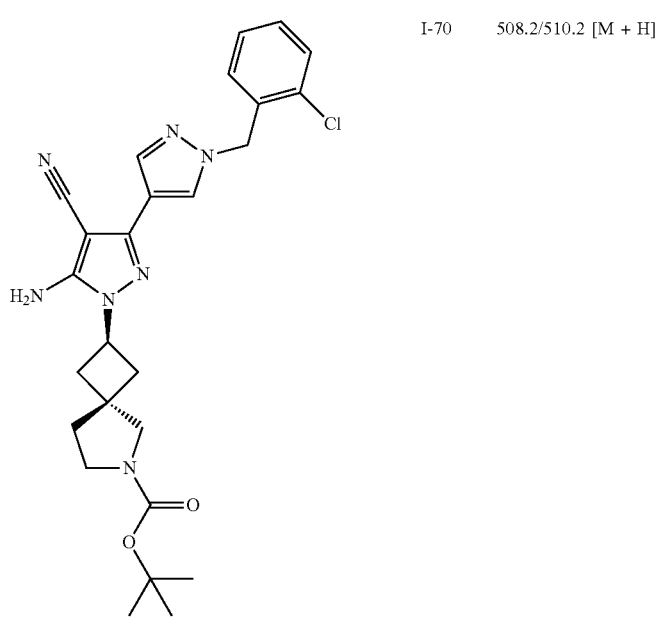 | I-69 | 542.5 [M + H] |
| 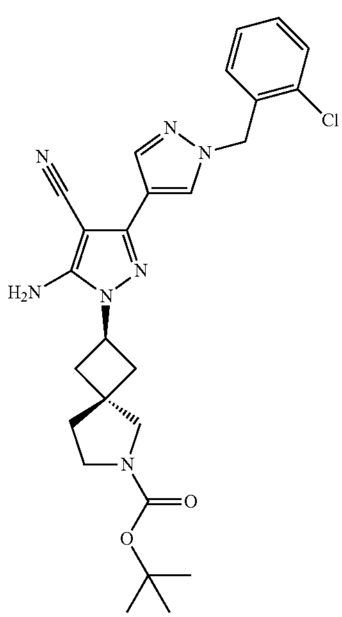 [SMILES: CC(C)(C)OC(=O)N1CC[C@]2(C1)C[C@H](n1nc(-c3cnn(Cc4ccccc4Cl)c3)c(C#N)c1N)C2] | I-70 | 508.2/510.2 [M + H] |

-continued
| Structure | Intermediate | m/z |
|---|---|---|
| 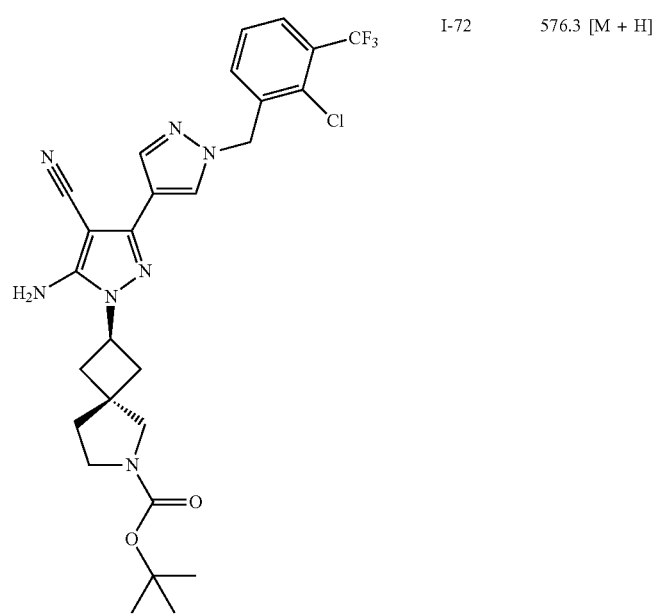 | I-71 | 576.3 [M + H] |
| 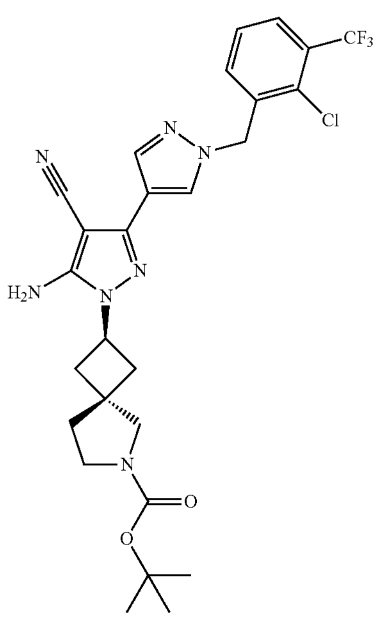 [SMILES: CC(C)(C)OC(=O)N1CC[C@]2(C1)C[C@H](n1nc(-c3cnn(Cc4cccc(C(F)(F)F)c4Cl)c3)c(C#N)c1N)C2] | I-72 | 576.3 [M + H] |

-continued
| Structure | Intermediate | m/z |
|---|---|---|
| 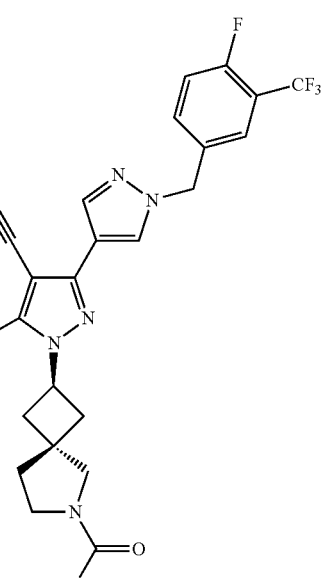 | I-73 | 560.0 [M + H] |
| 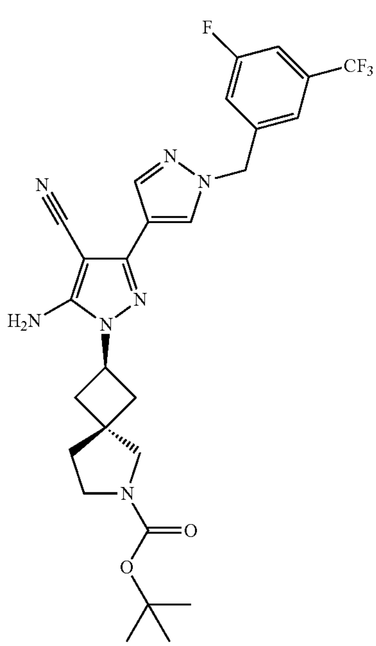 [SMILES: CC(C)(C)OC(=O)N1CC[C@]2(C1)C[C@H](n1nc(-c3cnn(Cc4cc(F)cc(C(F)(F)F)c4)c3)c(C#N)c1N)C2] | I-74 | 560.0 [M + H] |

-continued
| Structure | Intermediate | m/z |
|---|---|---|
| 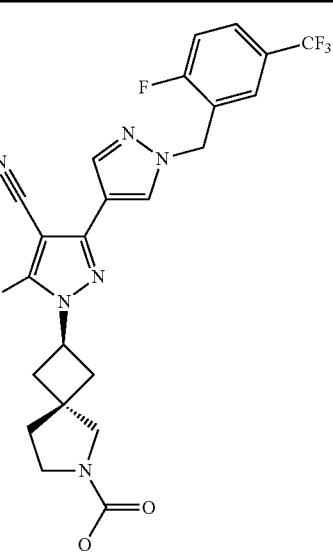 | I-75 | 560.0 [M + H] |
| 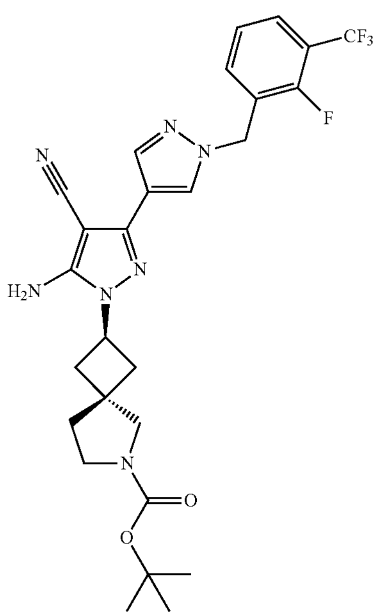 | I-76 | 560.0 [M + H] |

-continued

| Structure | Intermediate | m/z |
|---|---|---|
| 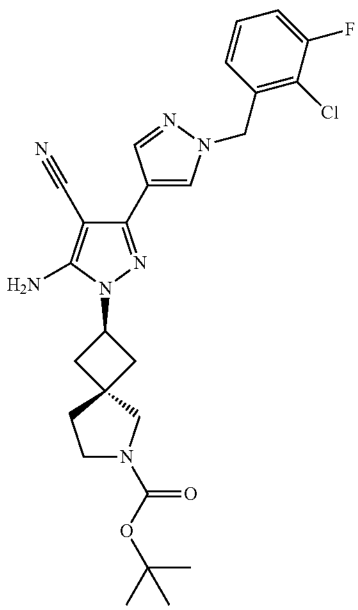 [SMILES: CC(C)(C)OC(=O)N1CC[C@]2(C1)C[C@H](n1nc(-c3cnn(Cc4cccc(F)c4Cl)c3)c(C#N)c1N)C2] | I-77 | 526.2/528.2 [M + H] |
| 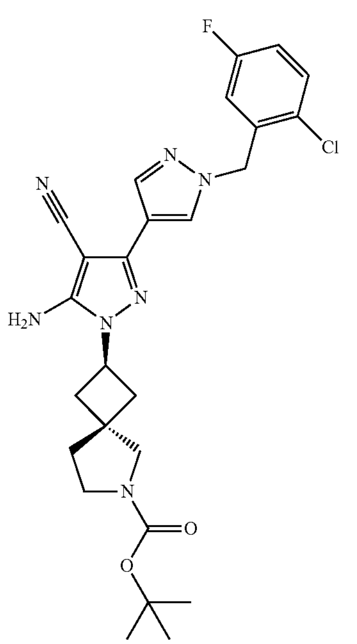 [SMILES: CC(C)(C)OC(=O)N1CC[C@]2(C1)C[C@H](n1nc(-c3cnn(Cc4cc(F)ccc4Cl)c3)c(C#N)c1N)C2] | I-78 | 526.3/528.2 [M + H] |

-continued
| Structure | Intermediate | m/z |
|---|---|---|
| 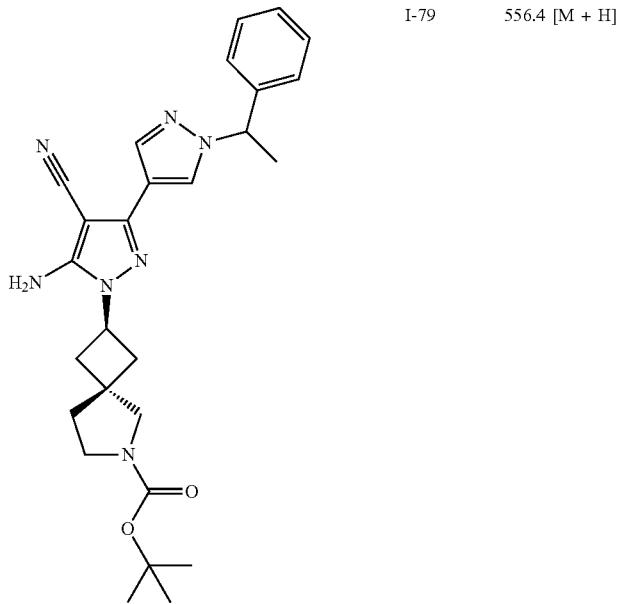 | I-79 | 556.4 [M + H] |
| 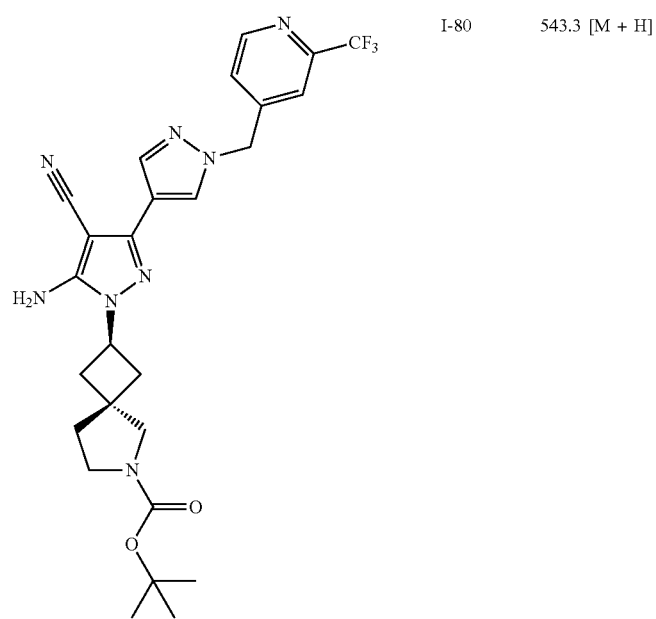 | I-80 | 543.3 [M + H] |

| Structure | Intermediate | m/z |
|---|---|---|
| 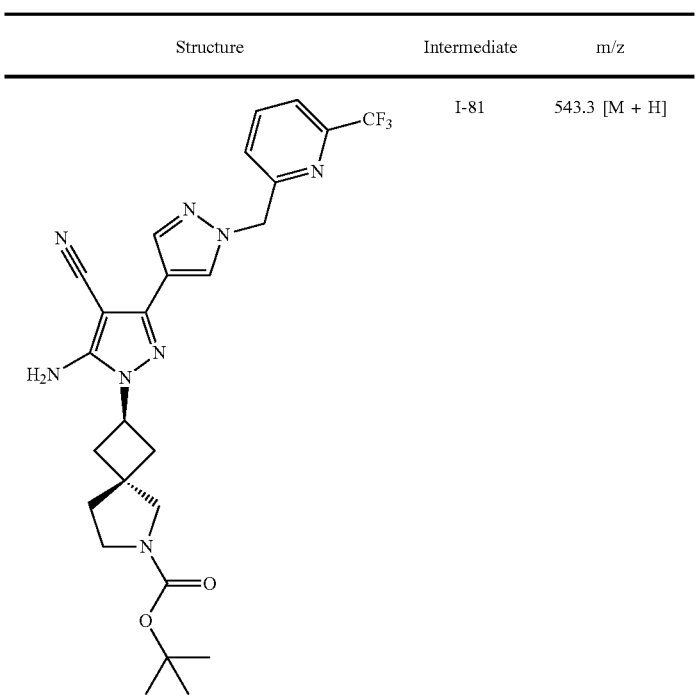 | I-81 | 543.3 [M + H] |
| 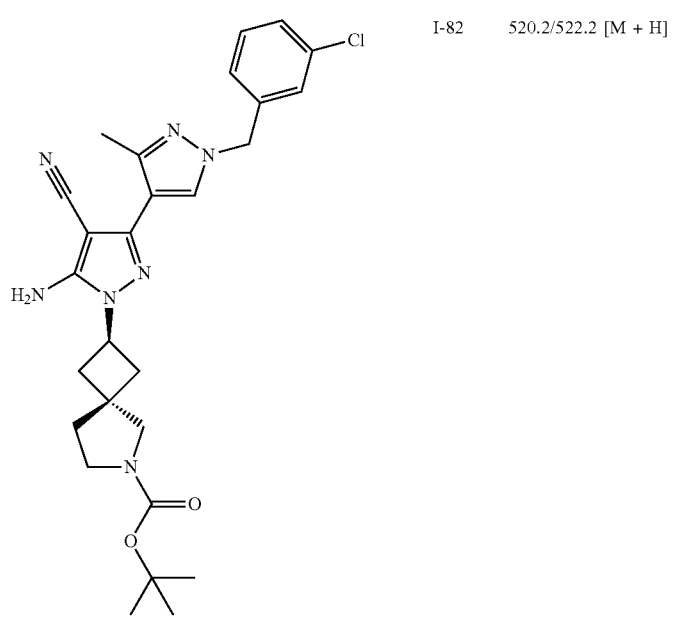 | I-82 | 520.2/522.2 [M + H] |

-continued
| Structure | Intermediate | m/z |
|---|---|---|
| 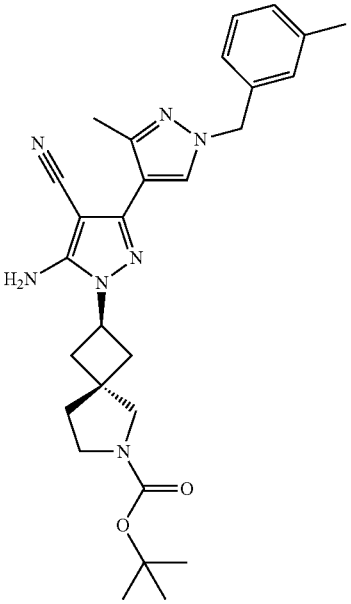 [SMILES: Cc1cccc(Cn2cc(-c3nn([C@H]4C[C@@]5(CCN(C(=O)OC(C)(C)C)C5)C4)c(N)c3C#N)c(C)n2)c1] | I-83 | 502.3 [M + H] |
| 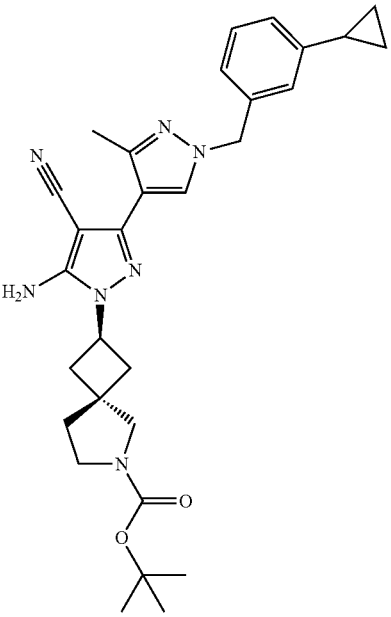 [SMILES: Cc1nn(Cc2cccc(C3CC3)c2)cc1-c1nn([C@H]2C[C@@]3(CCN(C(=O)OC(C)(C)C)C3)C2)c(N)c1C#N] | I-84 | 528.4 [M + H] |

-continued
| Structure | Intermediate | m/z |
|---|---|---|
| 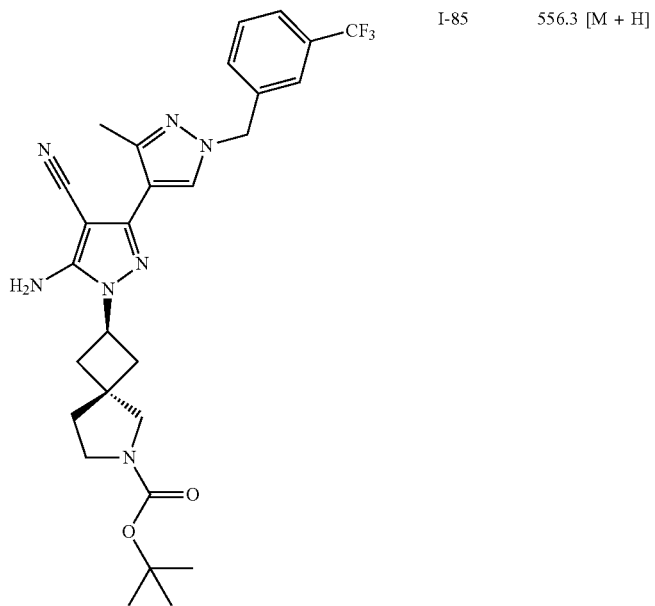 | I-85 | 556.3 [M + H] |
| 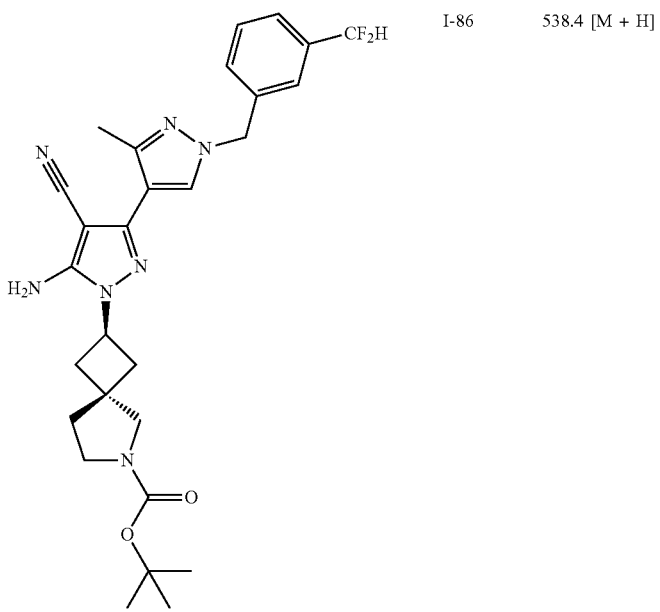 | I-86 | 538.4 [M + H] |

Method N
Synthesis of Intermediate I-87

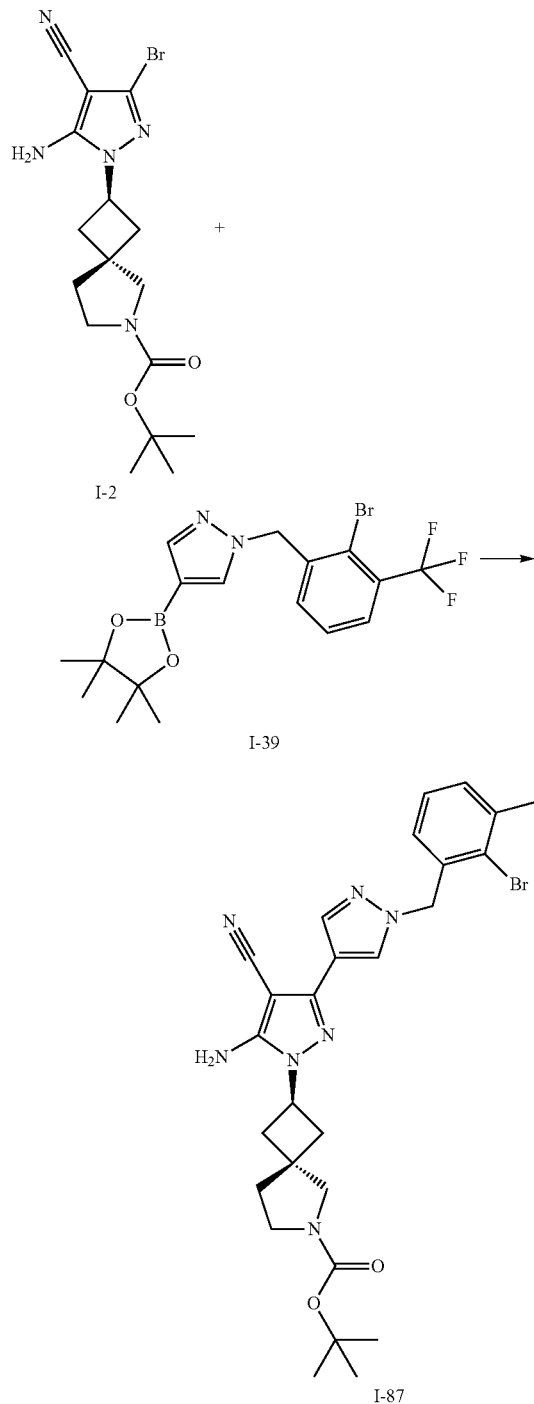

I-2 (0.7 g, 1.8 mmol), I-39 (1.5 g, 3.5 mmol), cesium carbonate (1.15 g, 3.5 mmol), Pd(PPh₃)₄ (0.2 g, 0.21 mmol), are combined in a microwave tube. Degassed dioxane (8 mL) and water (2 mL) are added. The reaction vessel is sealed under Ar and heated in a microwave for 60 min at 125° C. The reaction is transferred to a separatory funnel, diluted with EtOAc and rinsed with water and brine. The organics are dried, filtered, and evaporated in vacuo. The residue is then purified via flash chromatography (SiO₂, 0-55% EtOAc/heptane) to yield 710 mg of I-87, m/z=622.2 [M+H].

The following intermediates are prepared in similar fashion:

| Structure | Intermediate | m/z |
|---|---|---|
| 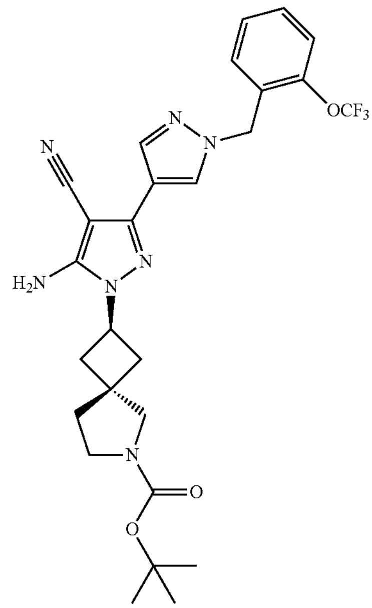 [SMILES: CC(C)(C)OC(=O)N1CC[C@]2(C1)C[C@H](n1nc(-c3cnn(Cc4ccccc4OC(F)(F)F)c3)c(C#N)c1N)C2] | I-88 | 558.4 [M + H] |
| 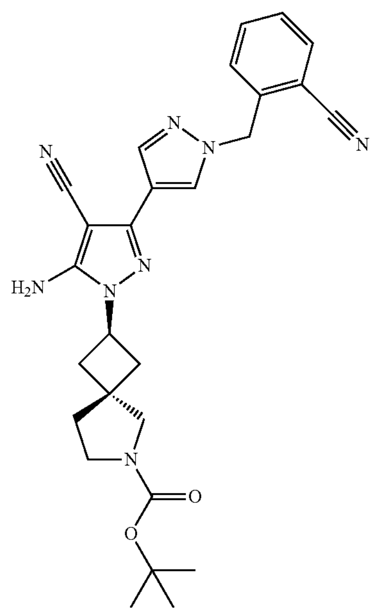 [SMILES: CC(C)(C)OC(=O)N1CC[C@]2(C1)C[C@H](n1nc(-c3cnn(Cc4ccccc4C#N)c3)c(C#N)c1N)C2] | I-89 | |

| Structure | Intermediate | m/z |
|---|---|---|
| 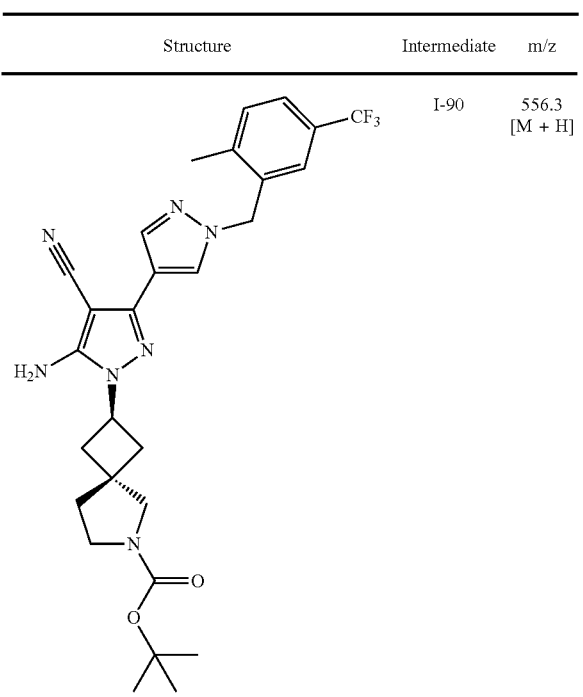 | I-90 | 556.3 [M + H] |
| 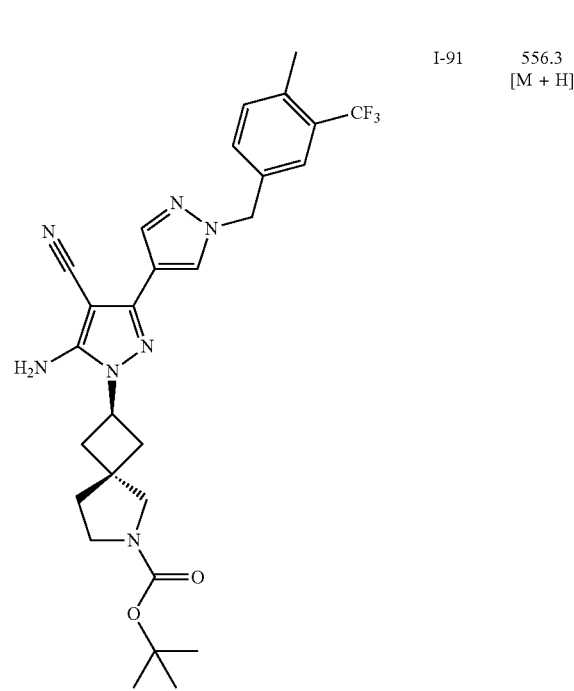 | I-91 | 556.3 [M + H] |
| Structure | Intermediate | m/z |
|---|---|---|
| 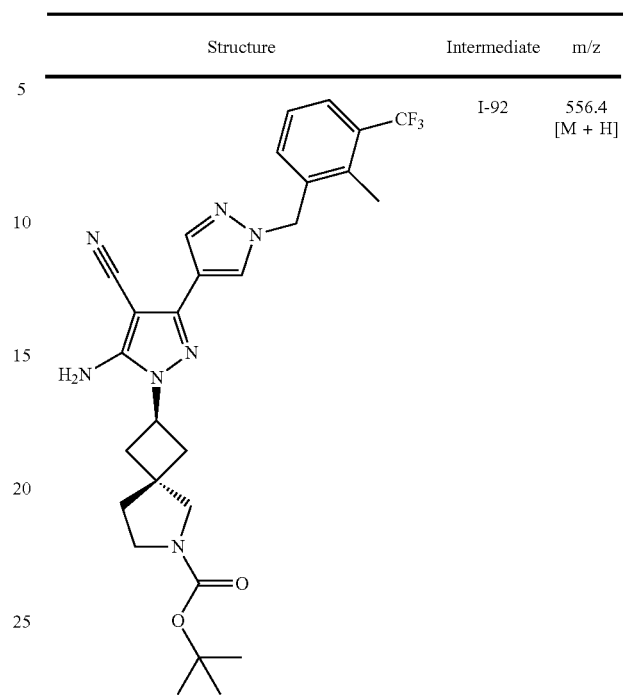 | I-92 | 556.4 [M + H] |
| 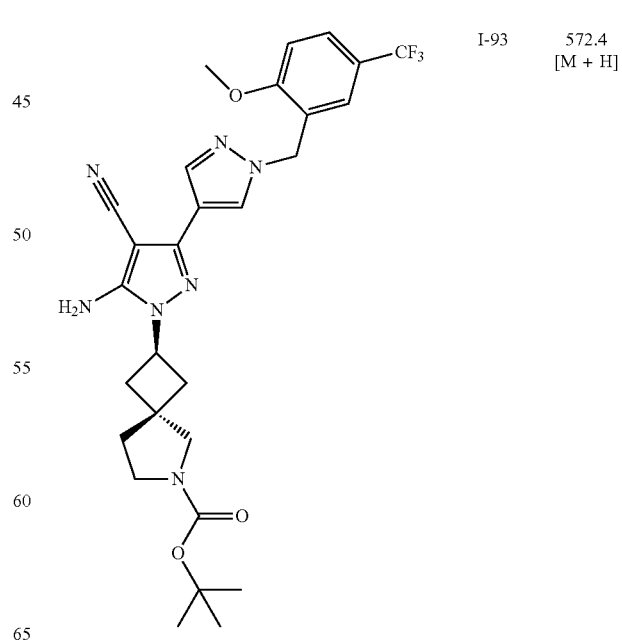 | I-93 | 572.4 [M + H] |

| Structure | Intermediate | m/z |
|---|---|---|
| 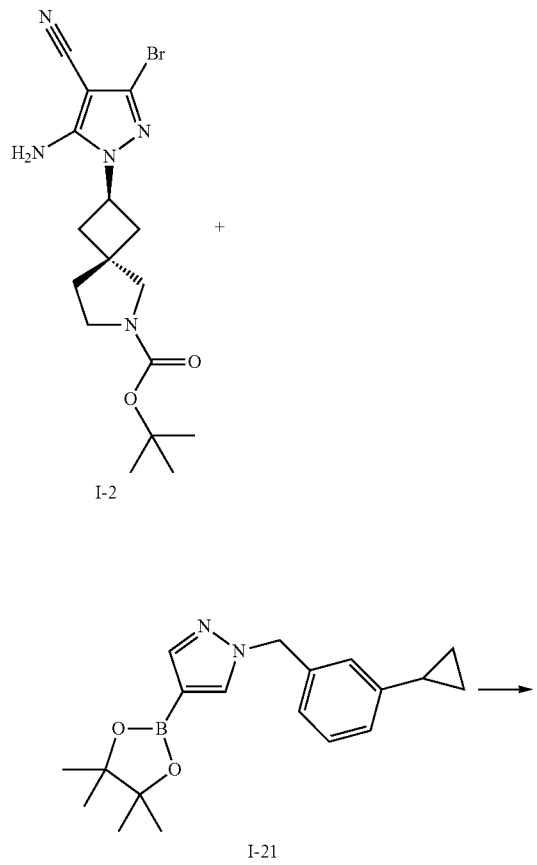 | I-94 | 576.3 [M + H] |

Method O

Synthesis of Intermediate I-95

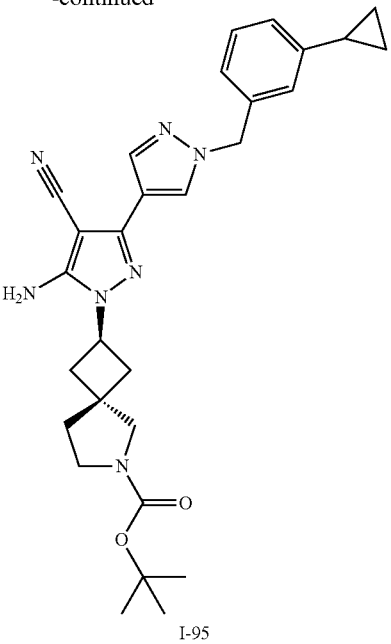

I-2 (310 mg, 0.78 mmol), I-21 (380 mg, 1.17 mmol), tricyclohexylphosphine (175 mg, 0.63 mmol) and potassium phosphate (500 mg, 2.3 mmol) are combined in 20 mL microwave vial in 8 ml of dioxane and 2 mL of water. Ar is bubbled through the solution for 10 minutes. Tris(dibenzylideneacetone)dipalladium (0) is then added and Ar is bubbled through the reaction for another 5 minutes. The reaction is sealed and heated in a microwave for 60 min at 120° C. After cooling to rt, the reaction solution is diluted with water and extracted with EtOAc (2×).

The combined organic extracts are dried over $MgSO_4$, filtered, and concentrated in vacuo. The crude reside is purified by flash chromatography ($SiO_2$, 10-90% EtOAc in heptane) and yields 340 mg of I-95, m/z=514.3 [M+H].

The following intermediates are prepared in similar fashion:

| Structure | Intermediate | m/z |
|---|---|---|
| 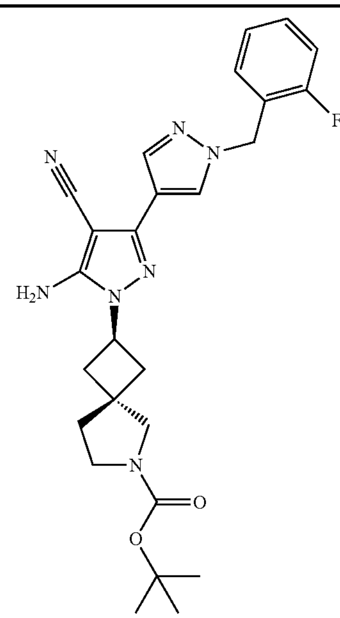 | I-96 | 492.3 [M + H] |

| Structure | Intermediate | m/z |
|---|---|---|
| 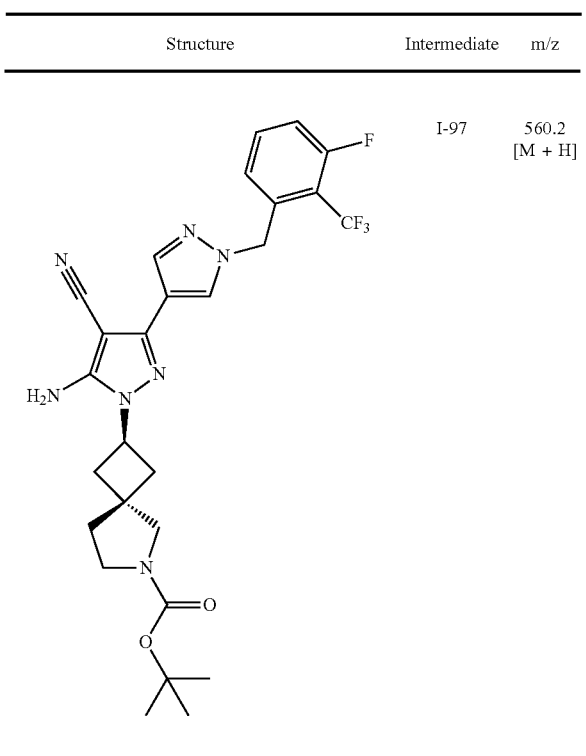 | I-97 | 560.2 [M + H] |
| | I-98 | 560.0 [M + H] |
| Structure | Intermediate | m/z |
|---|---|---|
| 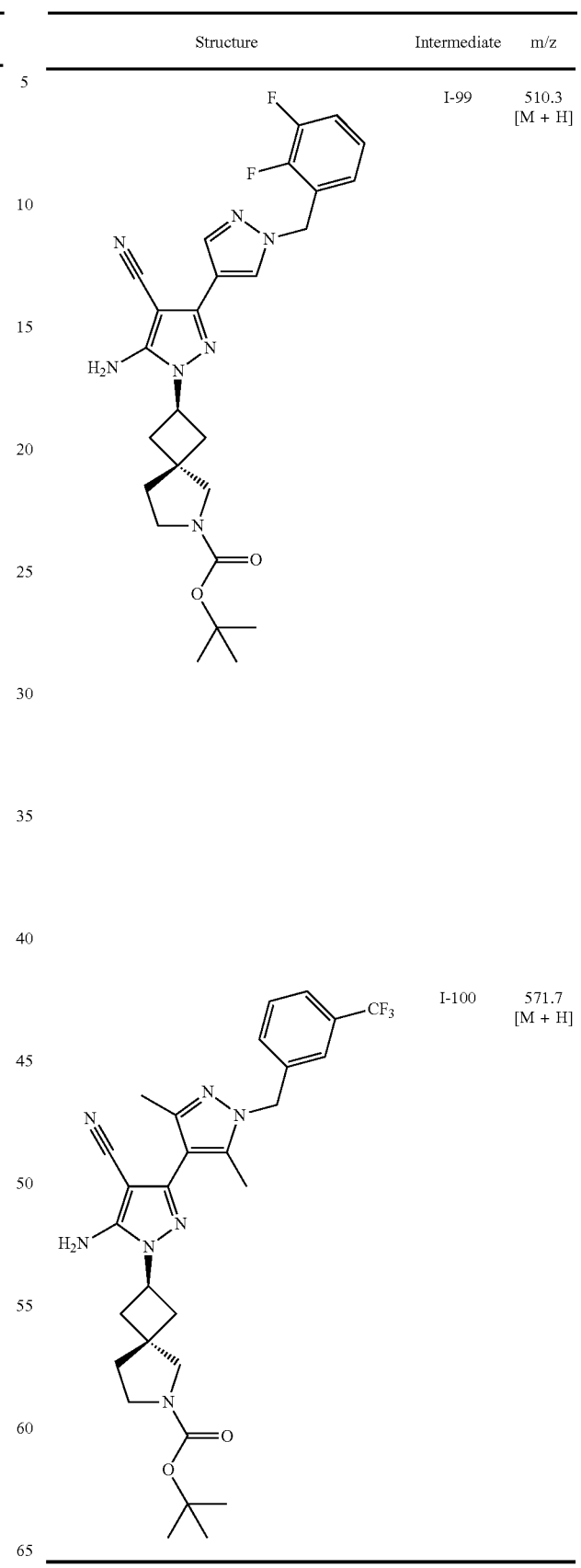 | I-99 | 510.3 [M + H] |
| | I-100 | 571.7 [M + H] |

Method P
Synthesis of Intermediate I-101

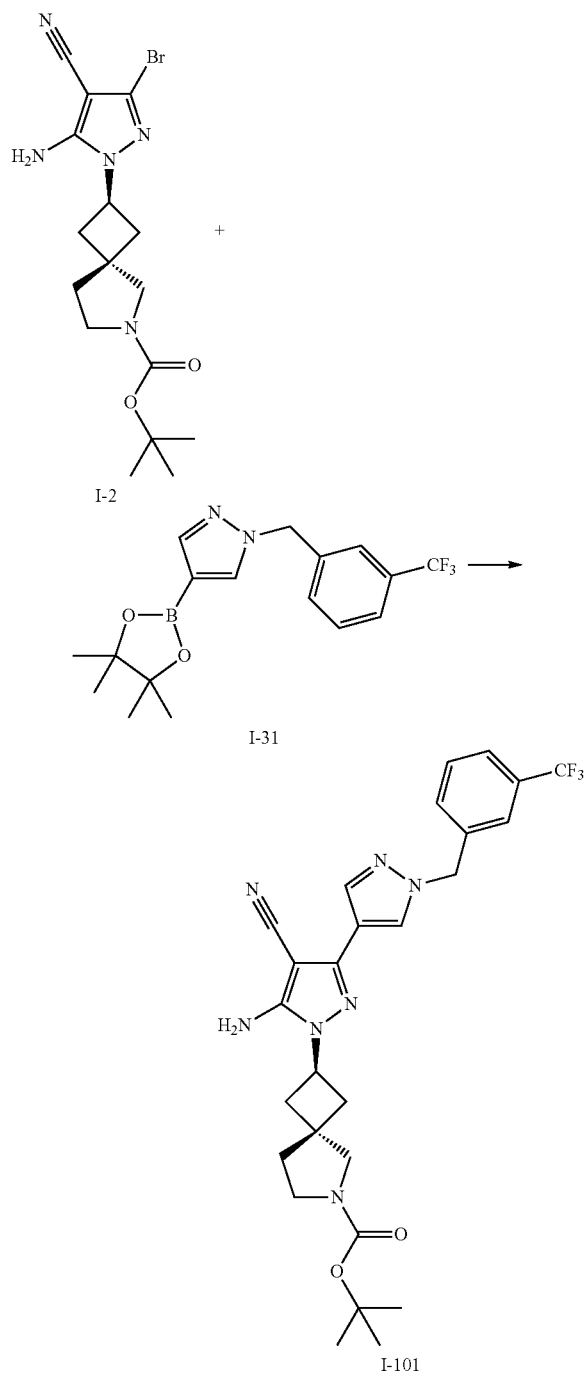

In a 1 L flask is placed I-2 (32.0 g, 80.8 mmol), I-31 (56.9 g, 161.5 mmol), cesium carbonate (52.6 g, 161.5 mmol) and Pd(PPh₃)₄ in 225 ml of Ar degassed DMA and 75 ml of water. This is equipped with a condenser under argon and then heated to 140° C. on a preheated reaction block. After 45 min, the reaction is cooled to rt and then filtered. The solids are rinsed with minimal EtOAc. The combined filtrates are transferred to a 2 L separatory funnel, diluted with approximately 750 mL of water and extracted with EtOAc (750 mL). The EtOAc is then rinsed with another 750 mL of water and then 750 mL of brine. The organics are then combined, dried over sodium sulfate, filtered and concentrated in vacuo. Flash chromatography (SiO₂, 0-75% EtOAc/heptane) yields 25 g of I-101. The impure fractions are isolated and re-purified by flash chromatography (SiO₂, 0-75% EtOAc/heptane) to yield 7.5 g of I-101. Total 33 g of I-101 (75%), m/z=560.4 [M+H].

The following intermediate is prepared in similar fashion:

| Structure | Intermediate | m/z |
|---|---|---|
| 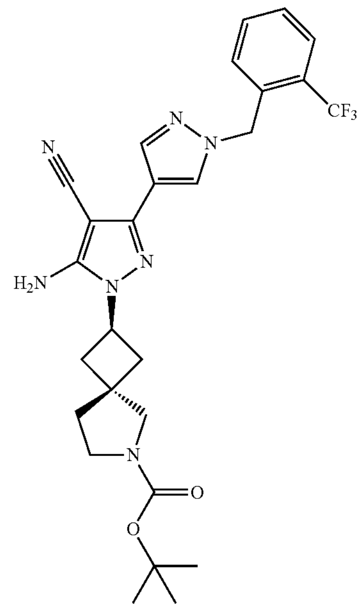 [SMILES: CC(C)(C)OC(=O)N1CC[C@]2(C1)C[C@H](n1nc(-c3cnn(Cc4ccccc4C(F)(F)F)c3)c(C#N)c1N)C2] | I-102 | 542.3/543.3 [M + H] |

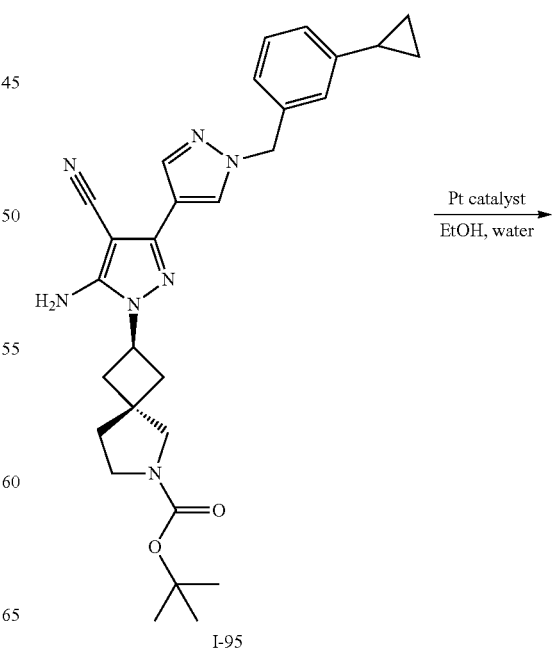

Method Q
Synthesis of Intermediate I-103

-continued

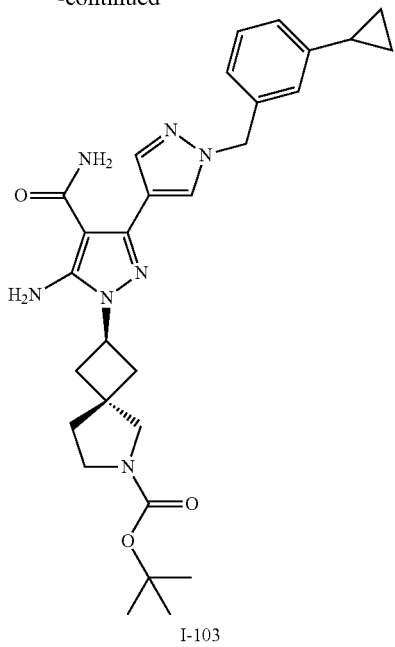

I-103

Hydrido(dimethylphosphinous acid-KP)[hydrogen bis(dimethylphosphinito-KP)]platinum(II) (79 mg, 0.19 mmol) is added to I-95 (1.0 g, 1.9 mmol) in water (3.0 mL) and ethanol (15 mL). The heterogeneous reaction is heated to 80° C. After 18 h, the reaction is cooled to rt. The reaction is concentrated in vacuo. The residue is combined with EtOAc and filtered. The filtrate is concentrated in vacuo to yield 500 mg of I-103, m/z=532.3 [M+H]. The product is used in subsequent steps without further purification.

The following intermediates are prepared in similar fashion:

| Structure | Intermediate | m/z |
|---|---|---|
|  | I-104 | 560.4 [M + H] |
| 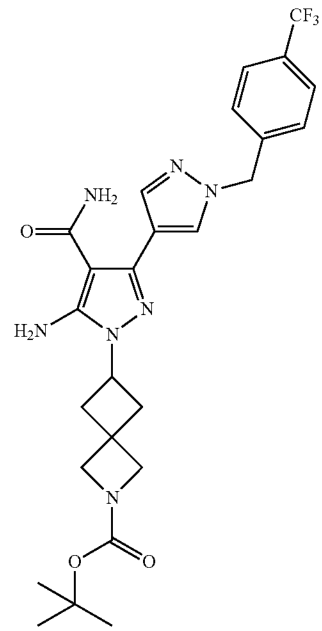 [SMILES: CC(C)(C)OC(=O)N1CC2(CC(n3nc(-c4cnn(Cc5ccc(C(F)(F)F)cc5)c4)c(C(N)=O)c3N)C2)C1] | I-105 | 546.4 [M + H] |
| 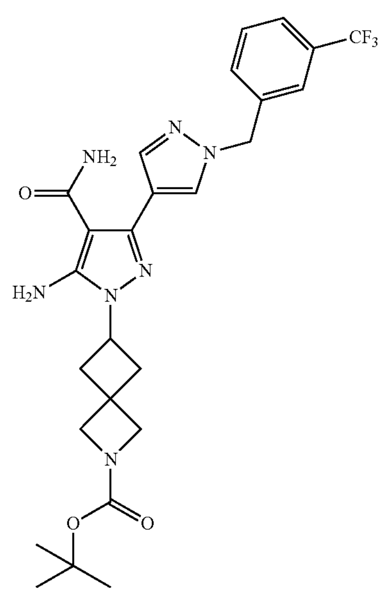 | I-106 | 614.4 [M + H] |

| Structure | Intermediate | m/z |
|---|---|---|
| 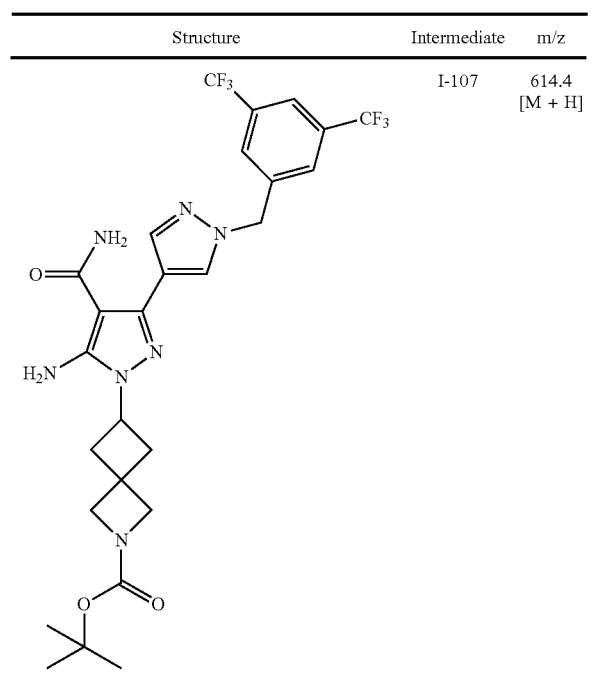 | I-107 | 614.4 [M + H] |
| Structure | Intermediate | m/z |
|---|---|---|
| | I-109 | |
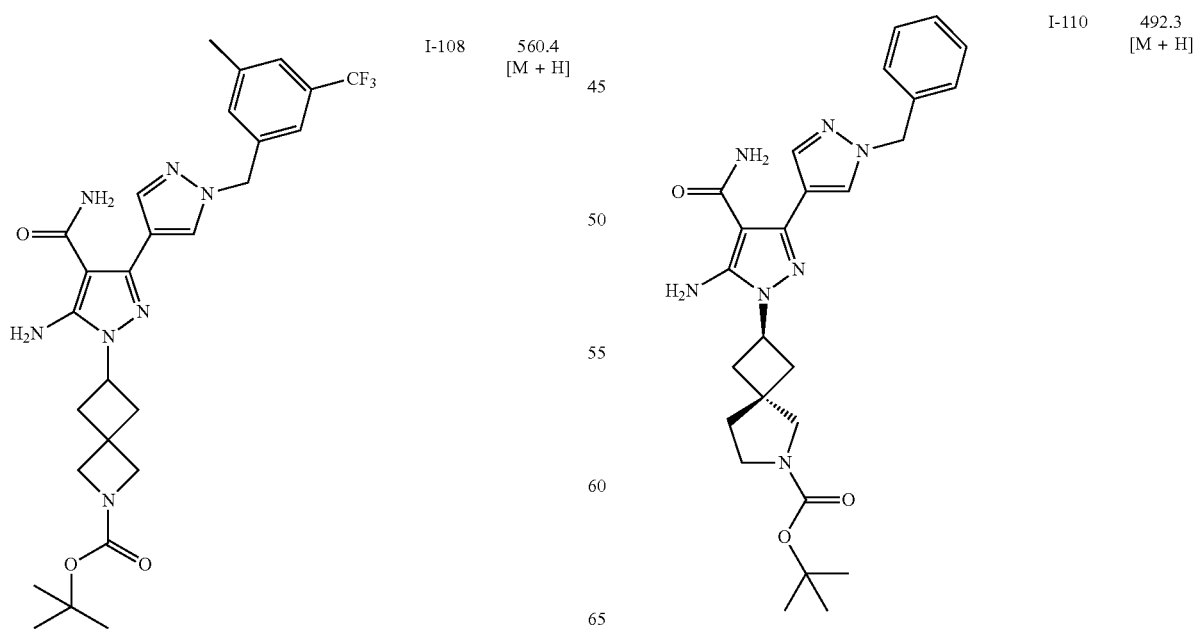
| | I-108 | 560.4 [M + H] |
| | I-110 | 492.3 [M + H] |

| Structure | Intermediate | m/z |
|---|---|---|
| 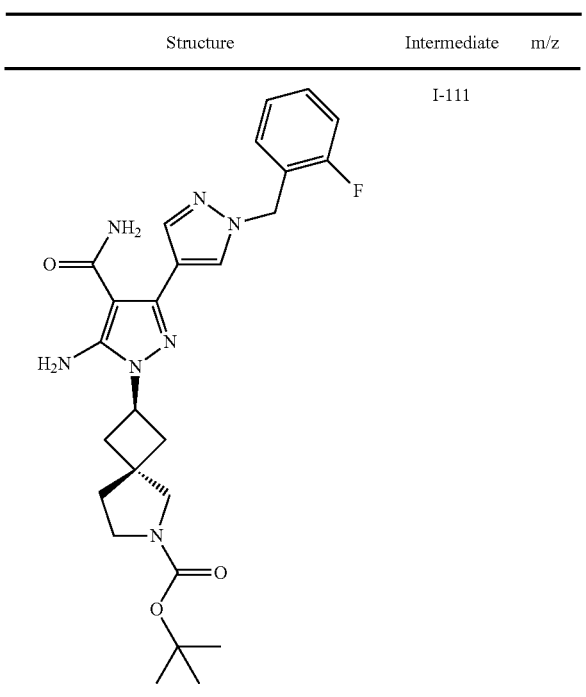 | I-111 | |
| | I-112 | 506.4 [M + H] |
| Structure | Intermediate | m/z |
|---|---|---|
| 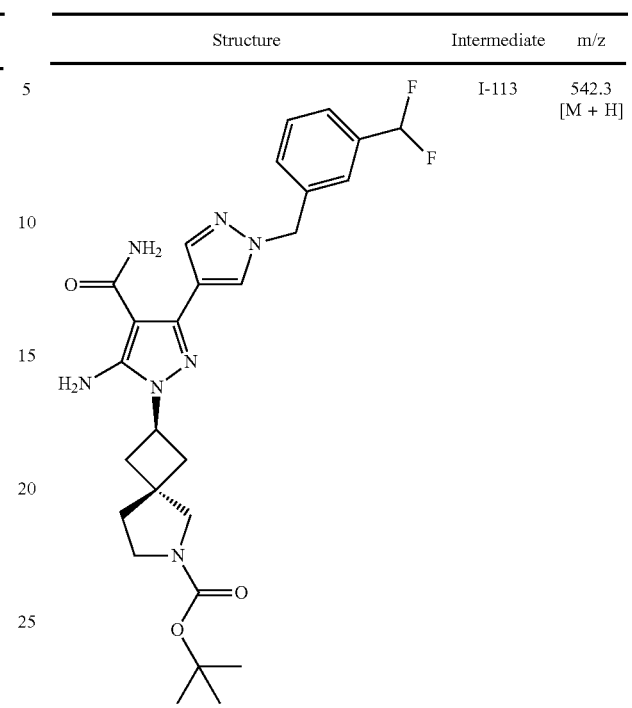 | I-113 | 542.3 [M + H] |
| | I-114 | 560.2 [M + H] |
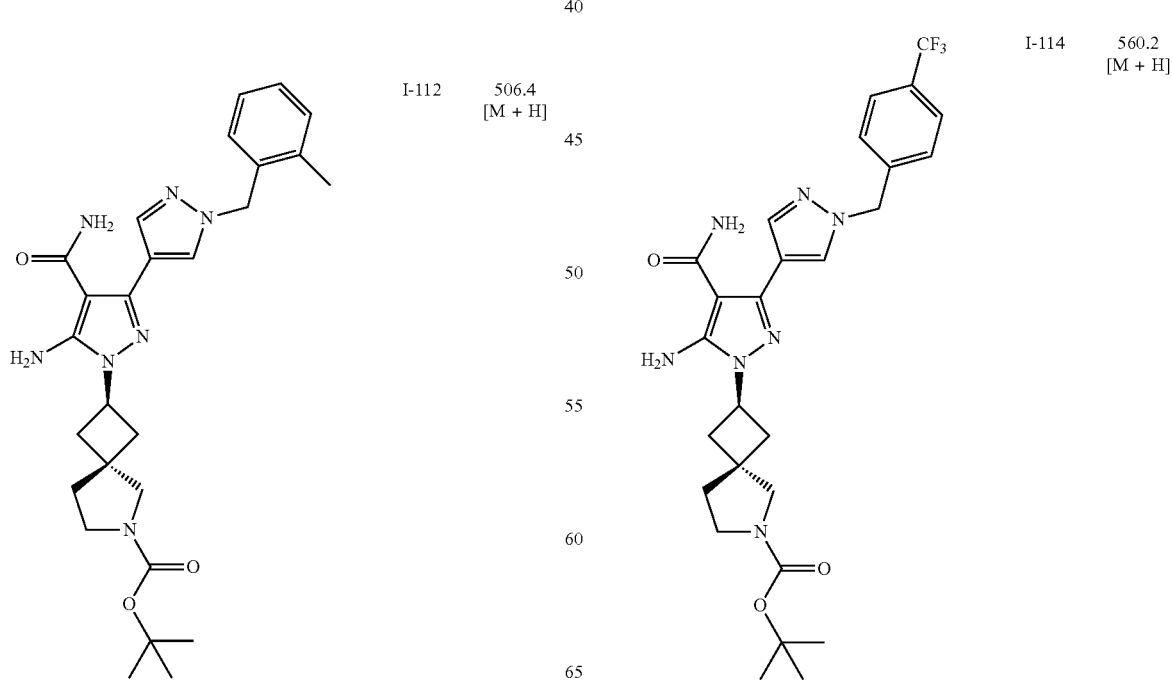

| Structure | Intermediate | m/z |
|---|---|---|
| 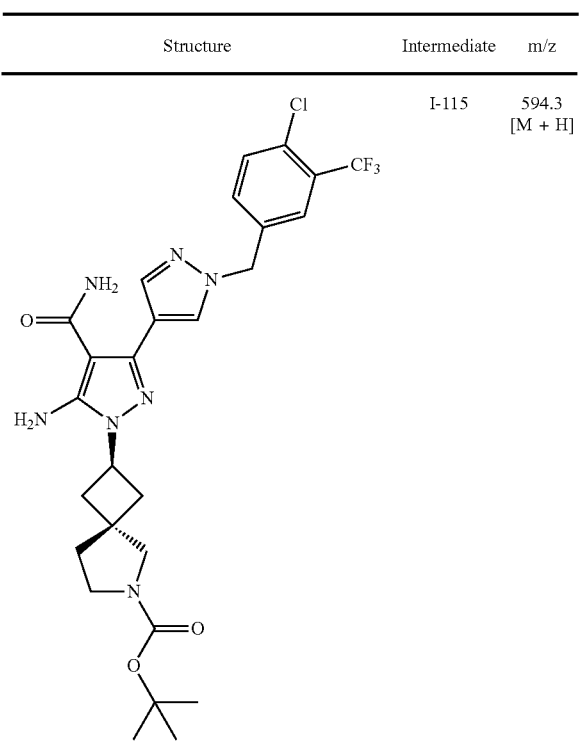 | I-115 | 594.3 [M + H] |
| | I-116 | 594.3 [M + H] |
| Structure | Intermediate | m/z |
|---|---|---|
| 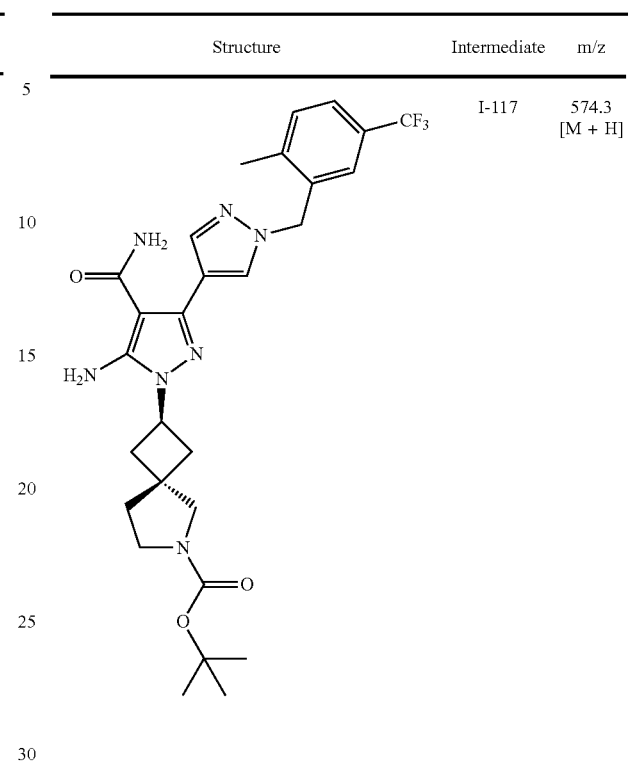 | I-117 | 574.3 [M + H] |
| 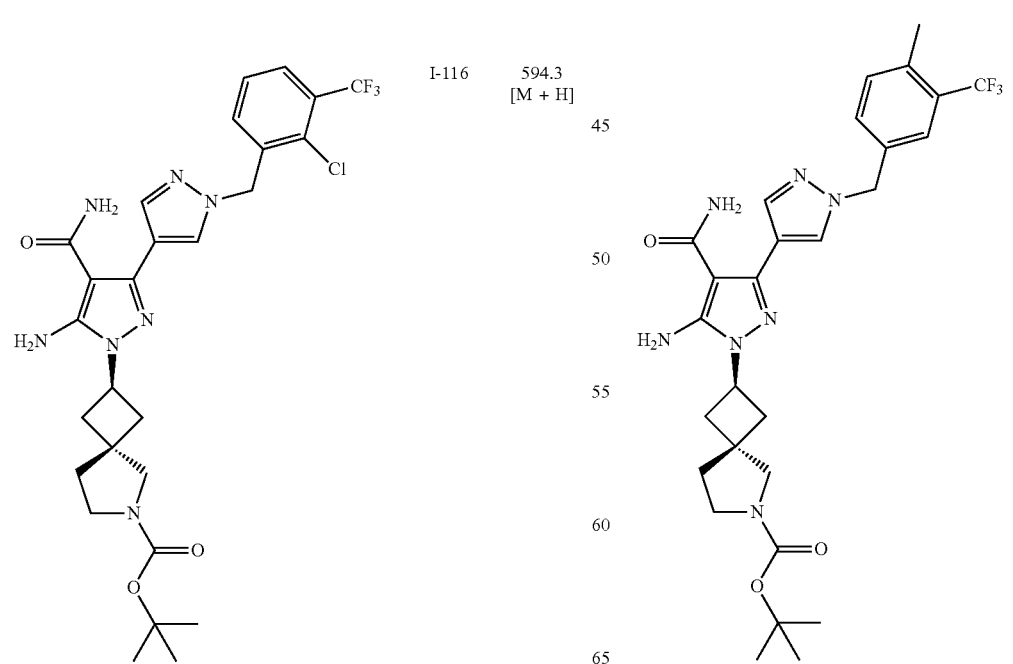 | I-118 | 574.4 [M + H] |

| Structure | Intermediate | m/z |
|---|---|---|
| 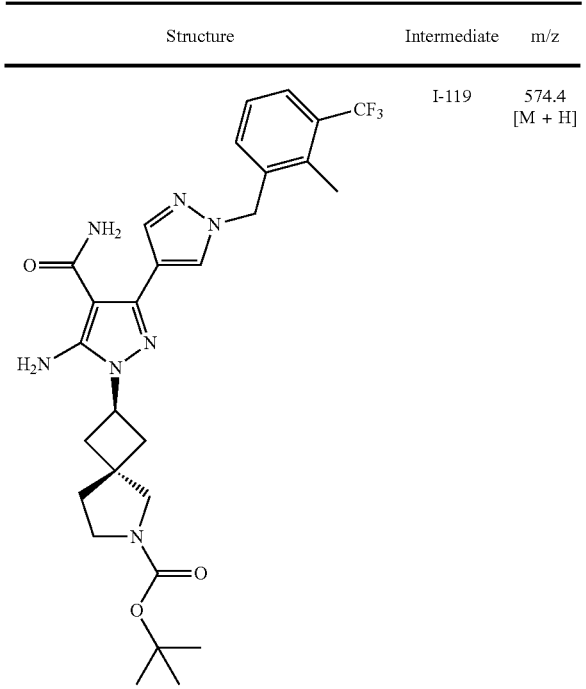 | I-119 | 574.4 [M + H] |
| 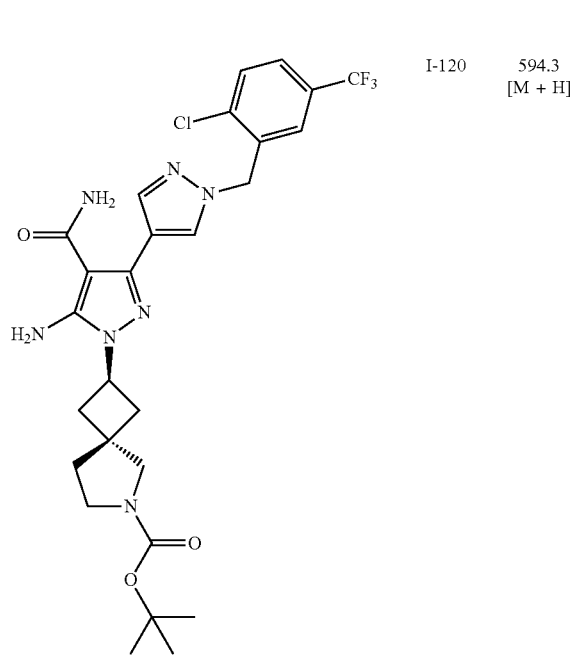 | I-120 | 594.3 [M + H] |
| Structure | Intermediate | m/z |
|---|---|---|
| 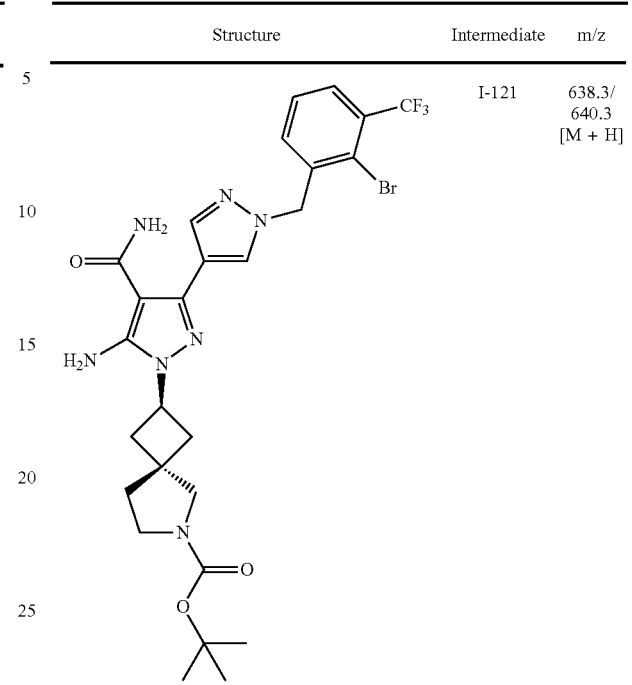 | I-121 | 638.3/ 640.3 [M + H] |
| 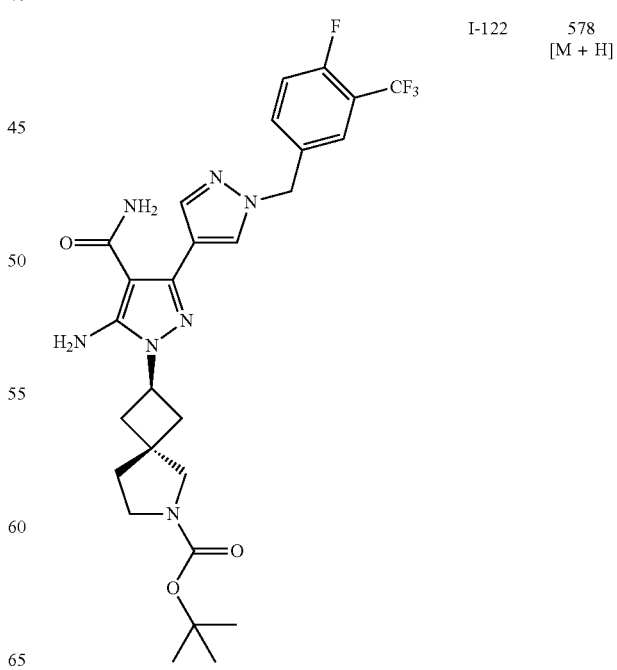 | I-122 | 578 [M + H] |

| Structure | Intermediate | m/z |
|---|---|---|
| 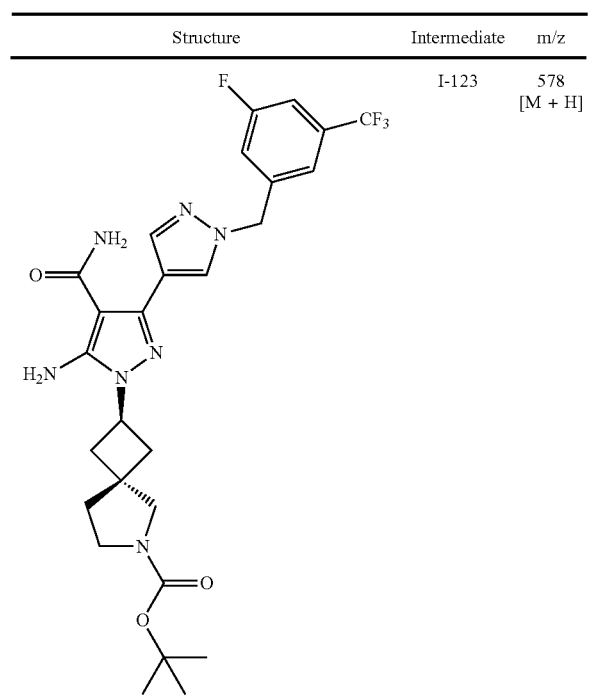 | I-123 | 578 [M + H] |
| | I-124 | 578 [M + H] |
| Structure | Intermediate | m/z |
|---|---|---|
| 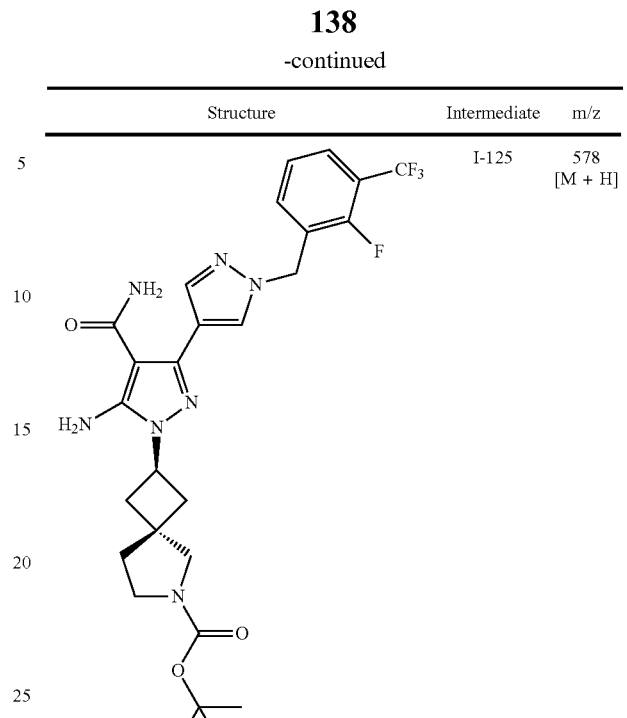 | I-125 | 578 [M + H] |
| | I-126 | 574.2 [M + H] |
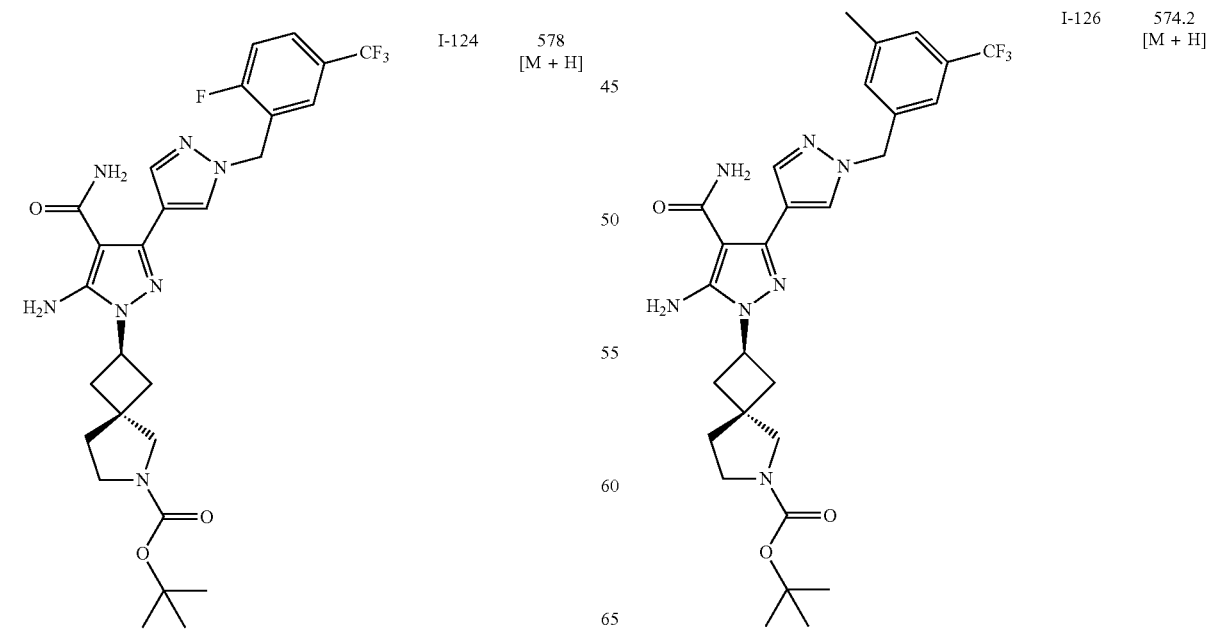

| Structure | Intermediate | m/z |
|---|---|---|
| 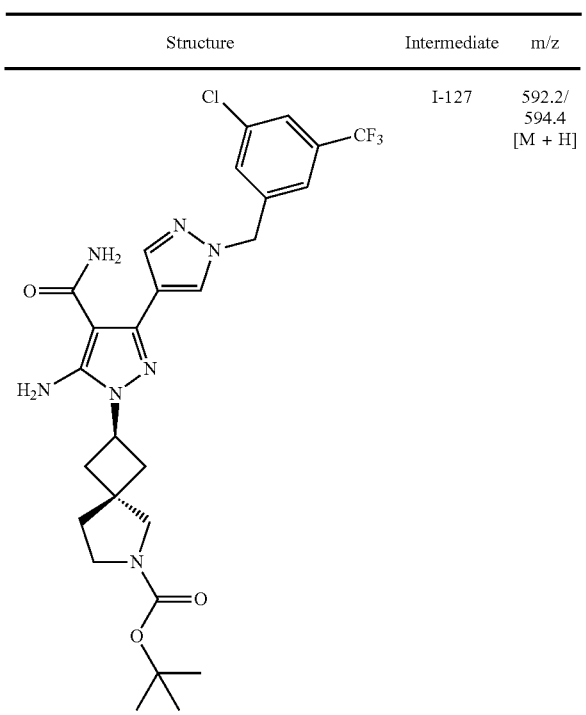 | I-127 | 592.2/ 594.4 [M + H] |
| 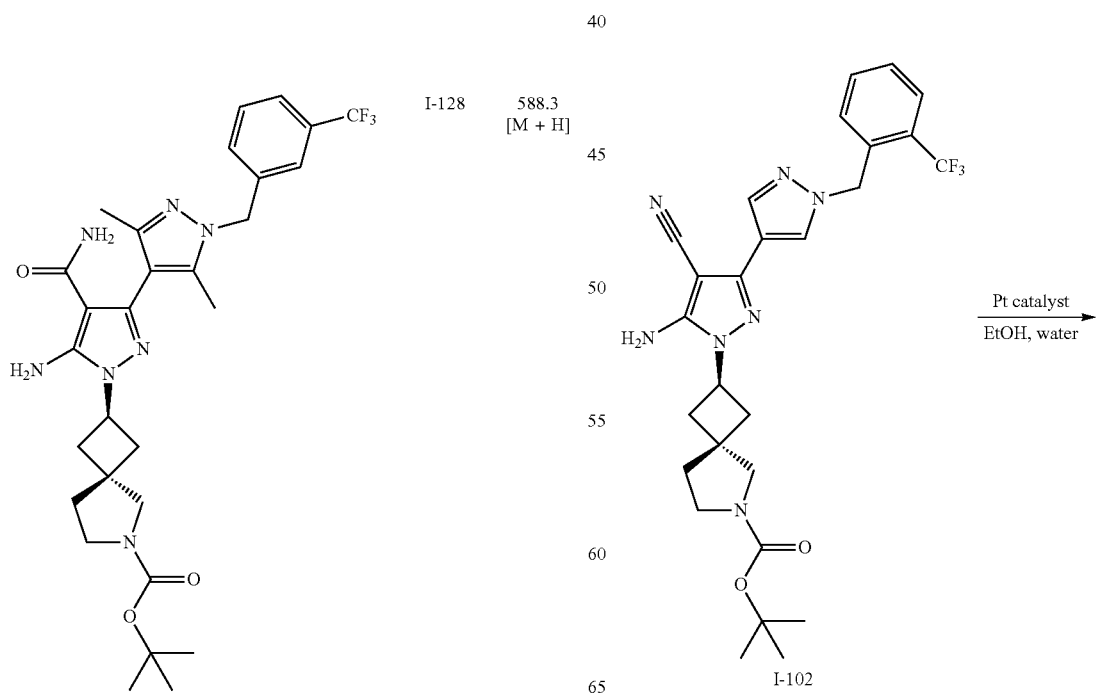 | I-128 | 588.3 [M + H] |
| Structure | Intermediate | m/z |
|---|---|---|
| 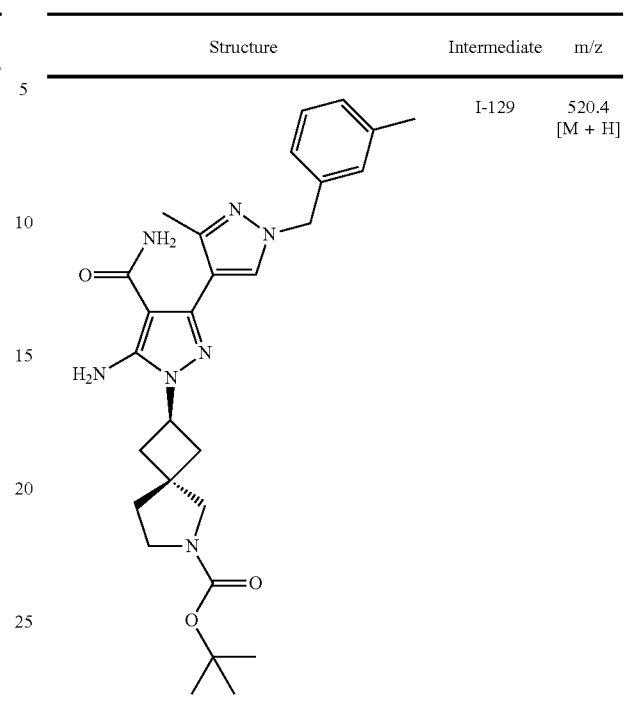 | I-129 | 520.4 [M + H] |
Method R
Synthesis of Intermediate I-130

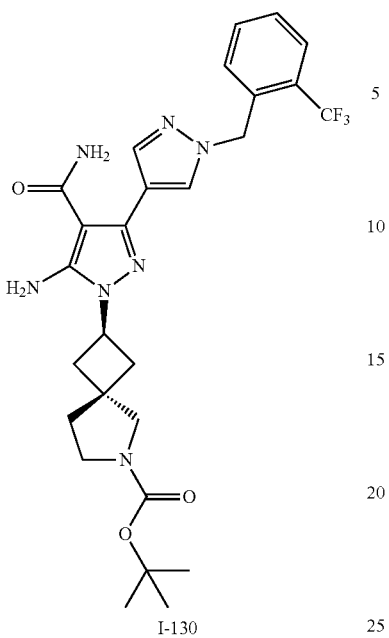

I-130

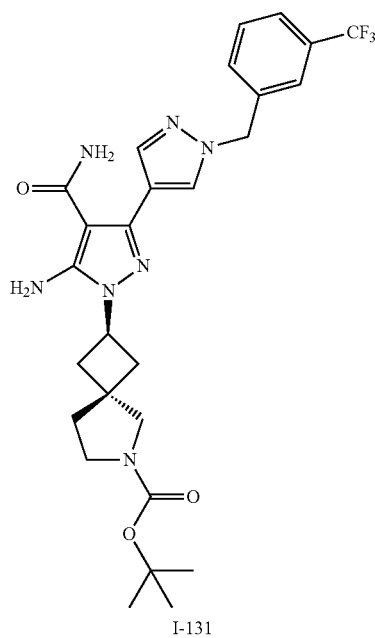

I-131

I-102 (61.5 g; 113.6 mmol) is dissolved in ethanol (200 mL) and water (40 mL). Hydrido(dimethylphosphinous acid-KP)[hydrogen bis(dimethylphosphinito-KP)]platinum (II) (2.91 g; 6.8 mmol) is added and the reaction allowed to stir at 80° C. for 16 h. The reaction solution is diluted with water, extracted with 5% MeOH/CH$_2$Cl$_2$ and the organic layer is collected, dried over MgSO$_4$, filtered and concentrated in vacuo. The residue is purified by flash chromatography (SiO$_2$, 0-100% EtOAc in Hep then 0-20% MeOH in CH$_2$Cl$_2$) to yield 57.2 g of I-130, m/z=560.3 [M+H].

Method S

Synthesis of Intermediate I-131

Hydrido(dimethylphosphinous acid-KP)[hydrogen bis(dimethylphosphinito-KP)]platinum(II) (2.91 g; 6.8 mmol) (863 mg 2.0 mmol) is added to the solution of I-101 (11.4 g, 20.2 mmol) in water (30 mL) and ethanol (100 mL) in a sealable vessel. The vessel is sealed and heated to 95° C. overnight. The reaction is concentrated in vacuo, diluted with EtOAc and filtered through Celite. The filtrate is concentrated in vacuo to yield 12 g of I-131, m/z=560.4 [M+H]. The material (I-131) is used without further purification.

Method T

Synthesis of Intermediate I-132

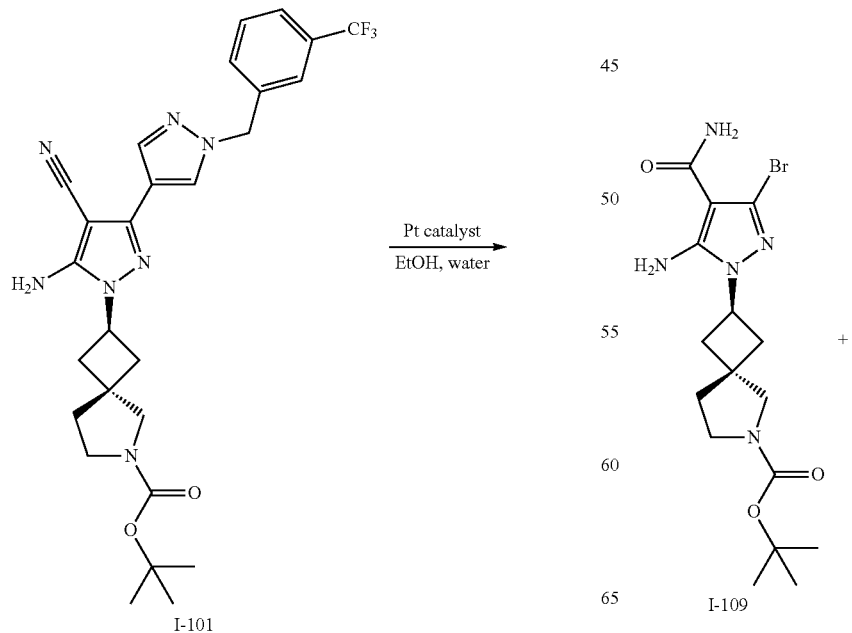

143
-continued

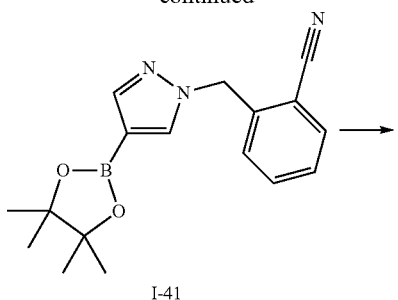

I-41

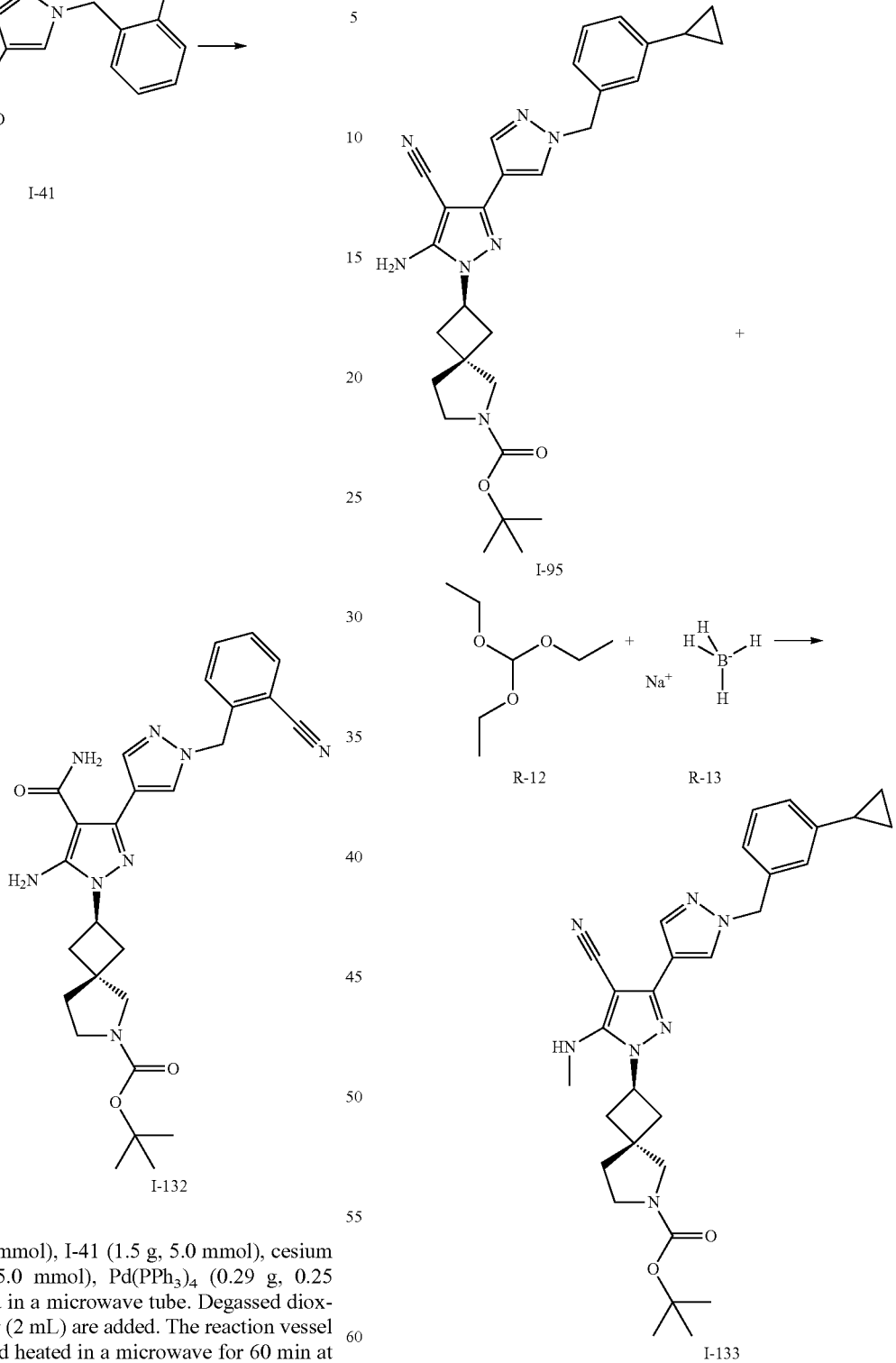

I-109 (1.04 g, 2.5 mmol), I-41 (1.5 g, 5.0 mmol), cesium carbonate (1.64 g, 5.0 mmol), Pd(PPh$_3$)$_4$ (0.29 g, 0.25 mmol), are combined in a microwave tube. Degassed dioxane (8 mL) and water (2 mL) are added. The reaction vessel is sealed under Ar and heated in a microwave for 60 min at 125° C. The reaction is transferred to a separatory funnel, diluted with EtOAc and rinsed with water and brine. The organics are dried, filtered, and concentrated in vacuo. The residue is then purified via flash chromatography (SiO$_2$, 0-20% MeOH in DCM) to yield 1000 mg of I-132, m/z=517.4 [M+H].

144
Method U
Synthesis of Intermediate I-133

I-95 (1.34 g, 2.6 mmol) is heated to 140° C. in trimethylorthoformate (R-12) (17.4 mL). After 18 h the excess trimethylorthoformate is removed in vacuo. The yellow residue is diluted with absolute ethanol (15 mL), sodium borohydride (R-13) (118 mg, 3.1 mmol) is added and the mixture stirred at rt. After 3 h, the solvent is removed in vacuo. The residue is diluted with water, extracted with EtOAc, dried over MgSO$_4$, filtered and concentrated in vacuo. The crude residue is purified by flash chromatography (SiO$_2$, 10-80% EtOAc in heptane) to yield 920 mg of I-133, m/z=528.3 [M+H].

The following intermediates are prepared in similar fashion:

| Structure | Intermediate | m/z |
|---|---|---|
| (3-Cl benzyl pyrazole structure) | I-134 | |
| (3-CF$_3$ benzyl pyrazole structure) | I-135 | 556.5 [M + H] |

Method V
Synthesis of Intermediate I-136

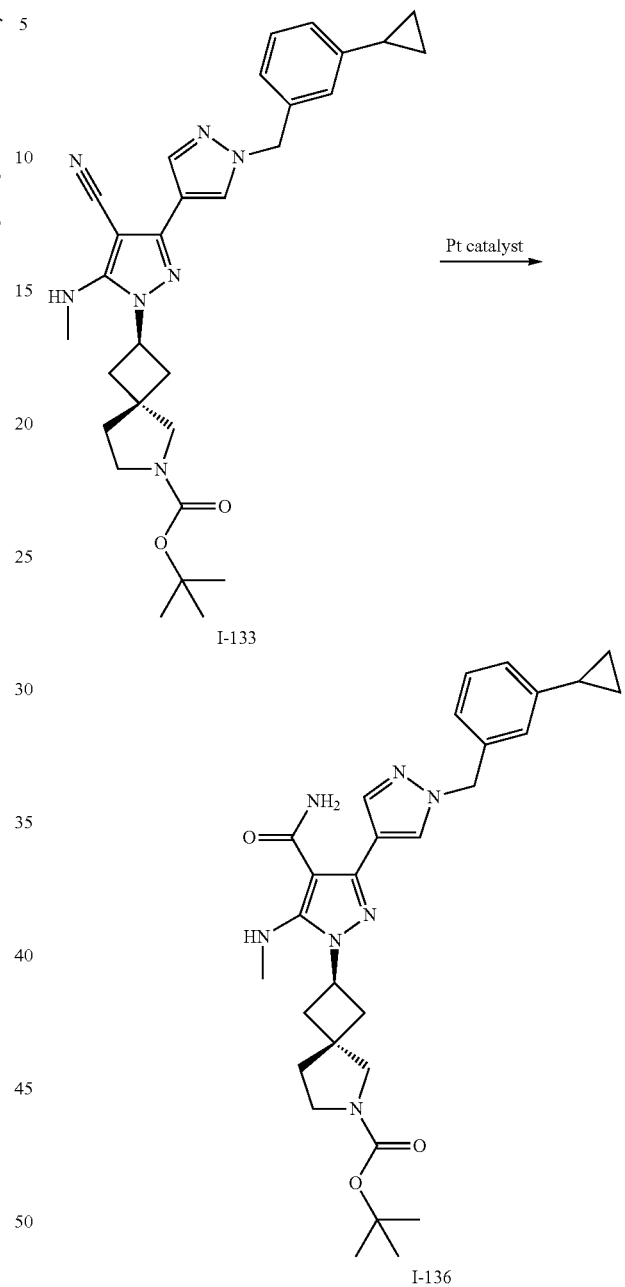

Hydrido(dimethylphosphinous acid-KP)[hydrogen bis(dimethylphosphinito-KP)]platinum(II) (70 mg, 0.16 mmol) is added to I-133 (890 mg, 1.7 mmol) in water (0.8 mL) and ethanol (2.4 mL). The heterogeneous reaction is heated to 80° C. After 18 h, the reaction is cooled to rt. Additional hydrido(dimethylphosphinous acid-KP)[hydrogen bis(dimethylphosphinito-KP)]platinum(II) (80 mg, 0.19 mmol) is added and the reaction is heated to 80° C. for 96 h. The reaction is concentrated in vacuo and partitioned between EtOAc and water. The layers are separated and the aqueous layer is extracted with EtOAc (2×). The combined organic layers are washed with brine, dried over MgSO$_4$, filtered and concentrated to give a residue that is purified by flash chromatography (SiO$_2$, 30-100% EtOAc in heptane) yielding 500 mg of I-136, m/z=546.4 [M+H].

The following intermediates are prepared in similar fashion:
| Structure | Intermediate | m/z |
|---|---|---|
| 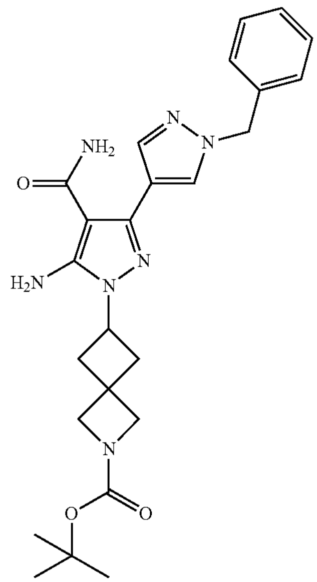 [SMILES: CC(C)(C)OC(=O)N1CC2(CC(n3nc(-c4cnn(Cc5ccccc5)c4)c(C(N)=O)c3N)C2)C1] | I-137 | 478.7 [M + H] |
| 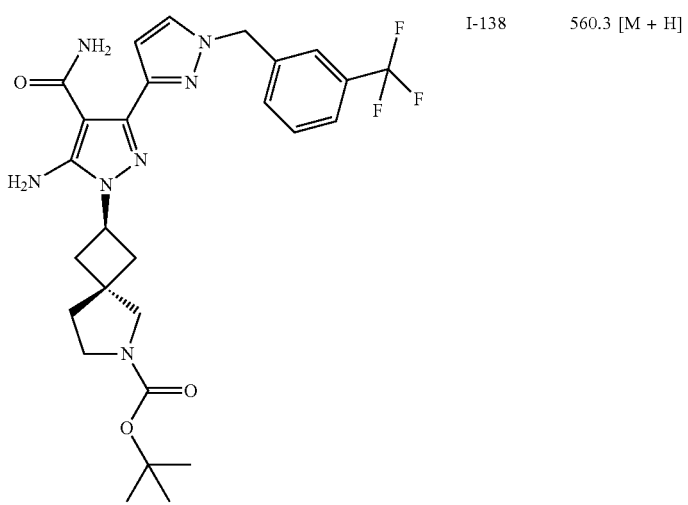 | I-138 | 560.3 [M + H] |

| Structure | Intermediate | m/z |
|---|---|---|
| 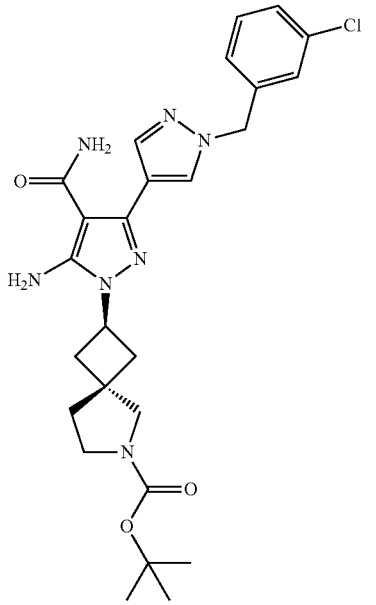 [SMILES: CC(C)(C)OC(=O)N1CC[C@]2(C1)C[C@H](n1nc(-c3cnn(Cc4cccc(Cl)c4)c3)c(C(N)=O)c1N)C2] | I-139 | 526.2 [M + H] |
| 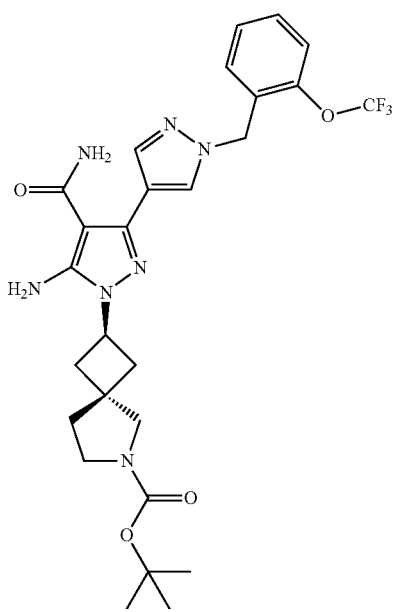 [SMILES: CC(C)(C)OC(=O)N1CC[C@]2(C1)C[C@H](n1nc(-c3cnn(Cc4ccccc4OC(F)(F)F)c3)c(C(N)=O)c1N)C2] | I-140 | 576.4 [M + H] |

-continued
| Structure | Intermediate | m/z |
|---|---|---|
| 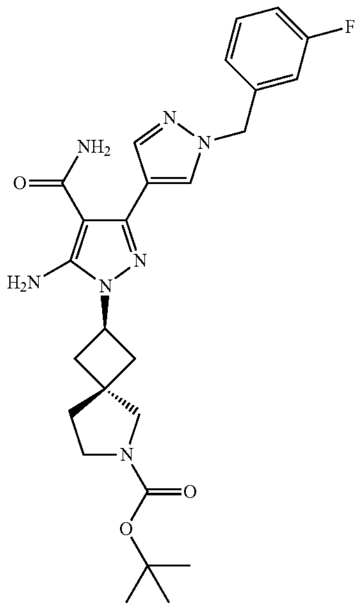 [SMILES: CC(C)(C)OC(=O)N1CC[C@]2(C1)C[C@H](n1nc(-c3cnn(Cc4cccc(F)c4)c3)c(C(N)=O)c1N)C2] | I-141 | 510 [M + H] |
| 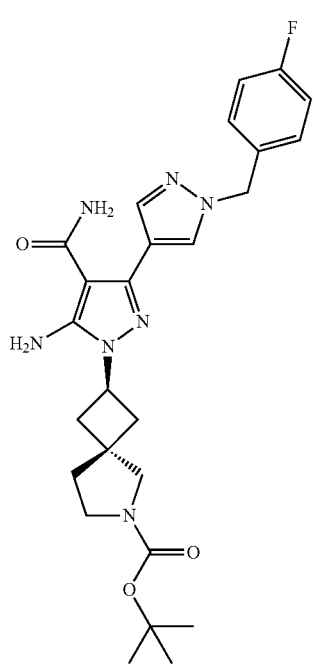 [SMILES: CC(C)(C)OC(=O)N1CC[C@]2(C1)C[C@H](n1nc(-c3cnn(Cc4ccc(F)cc4)c3)c(C(N)=O)c1N)C2] | I-142 | 510 [M + H] |

-continued
| Structure | Intermediate | m/z |
|---|---|---|
| 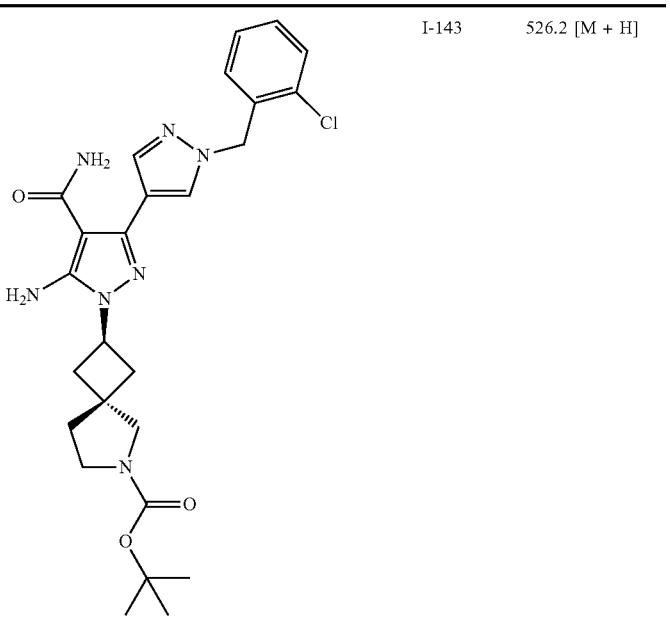 | I-143 | 526.2 [M + H] |
| 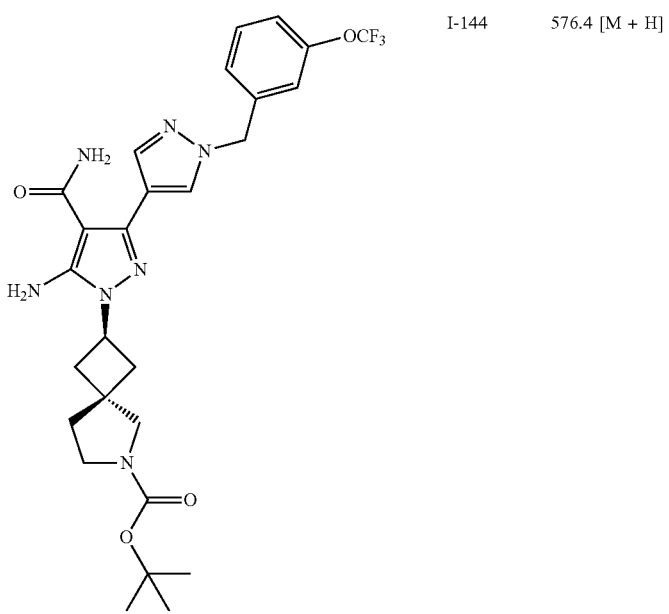 | I-144 | 576.4 [M + H] |

| Structure | Intermediate | m/z |
|---|---|---|
| 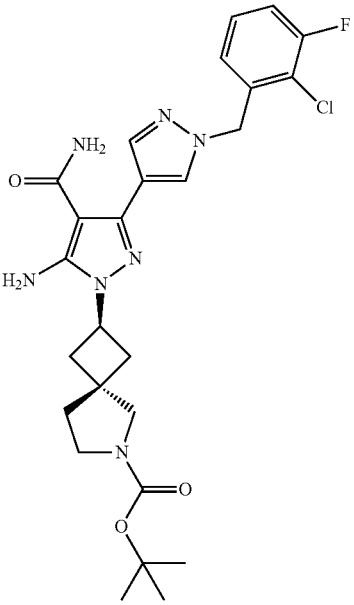 [SMILES: CC(C)(C)OC(=O)N1CC[C@]2(C1)C[C@H](n1nc(-c3cnn(Cc4cccc(F)c4Cl)c3)c(C(N)=O)c1N)C2] | I-145 | 544.2/546.2 [M + H] |
| 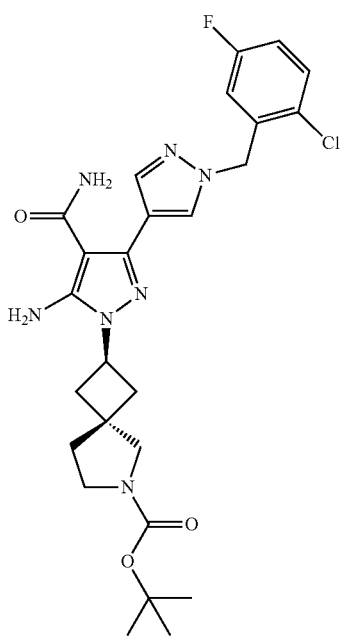 [SMILES: CC(C)(C)OC(=O)N1CC[C@]2(C1)C[C@H](n1nc(-c3cnn(Cc4cc(F)ccc4Cl)c3)c(C(N)=O)c1N)C2] | I-146 | 544.2/546.2 [M + H] |

| Structure | Intermediate | m/z |
|---|---|---|
| 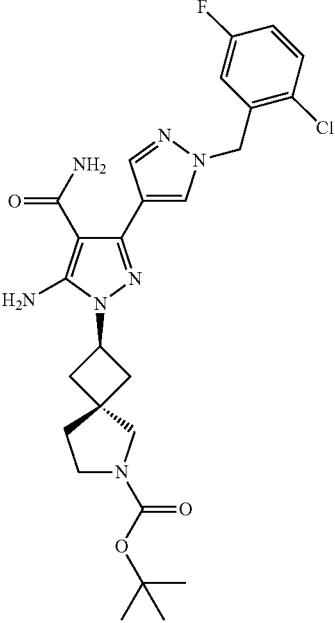 [SMILES: CC(C)(C)OC(=O)N1CC[C@]2(C1)C[C@H](n1nc(-c3cnn(Cc4cc(F)ccc4Cl)c3)c(C(N)=O)c1N)C2] | I-147 | 544.2/546.1 [M + H] |
| 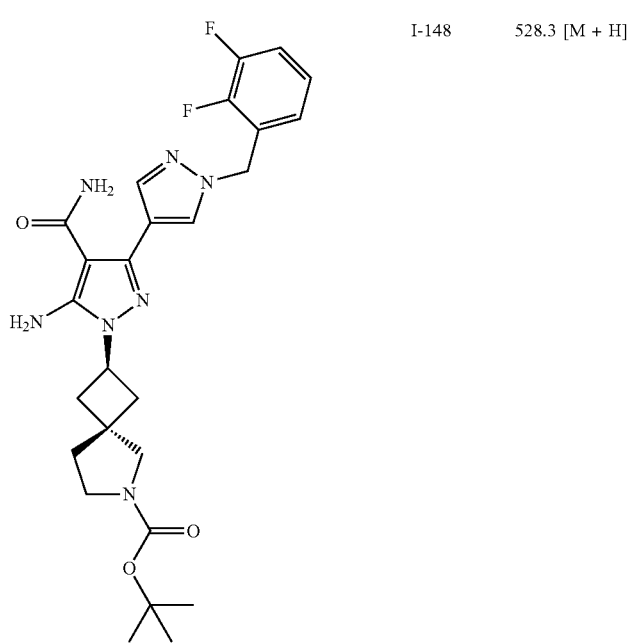 | I-148 | 528.3 [M + H] |

-continued
| Structure | Intermediate | m/z |
|---|---|---|
| 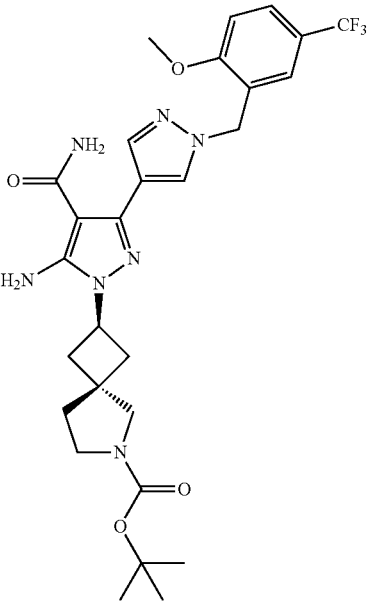 [SMILES: COc1ccc(C(F)(F)F)cc1Cn1cc(-c2nn([C@H]3C[C@@]4(CCN(C(=O)OC(C)(C)C)C4)C3)c(N)c2C(N)=O)cn1] | I-149 | 590.4 [M + H] |
| 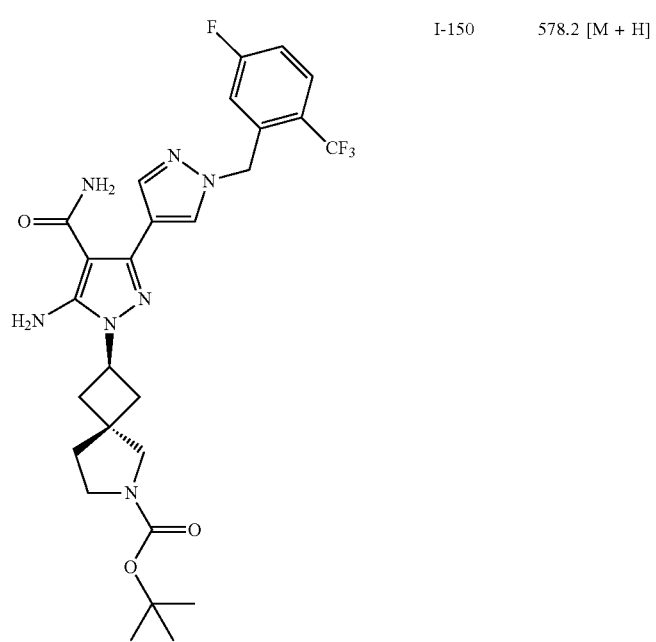 | I-150 | 578.2 [M + H] |

-continued
| Structure | Intermediate | m/z |
|---|---|---|
| 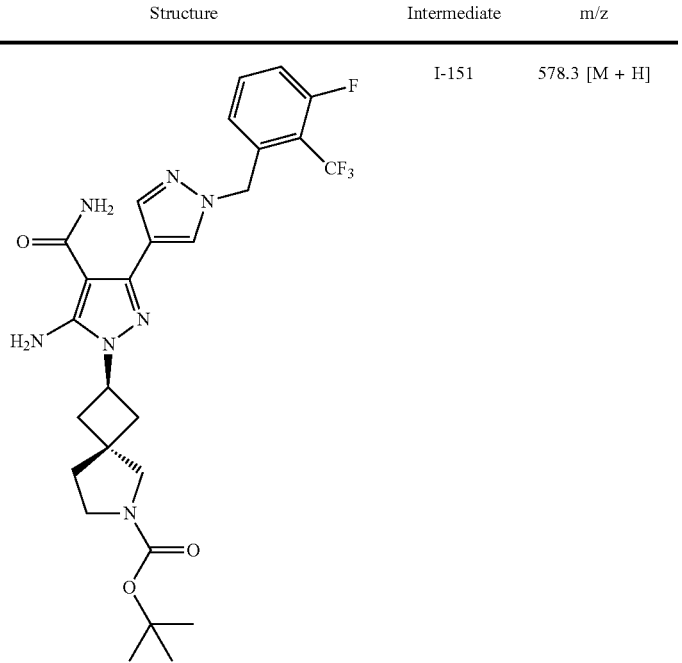 | I-151 | 578.3 [M + H] |
| 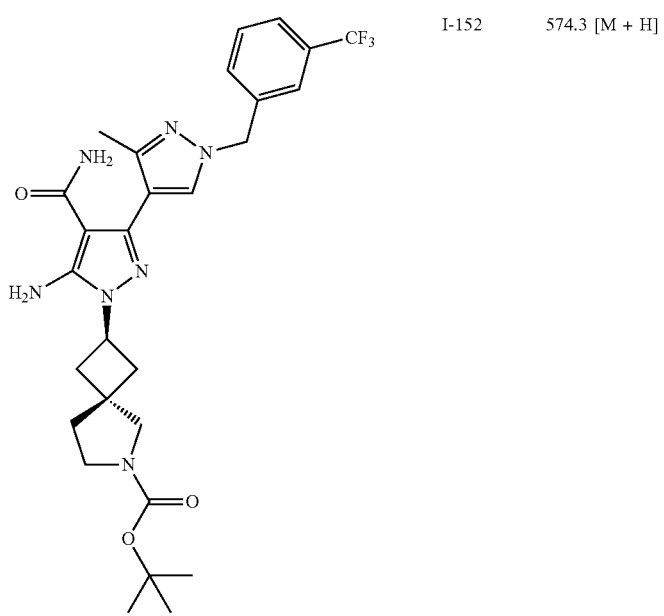 | I-152 | 574.3 [M + H] |

| Structure | Intermediate | m/z |
|---|---|---|
| 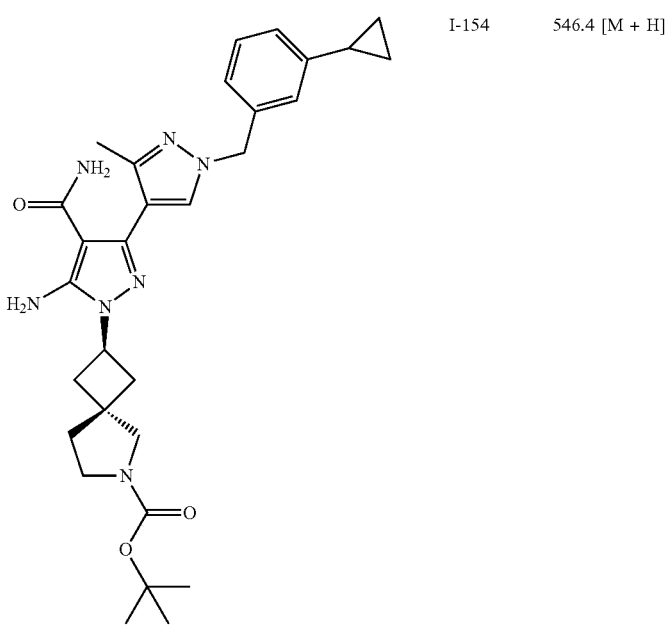 | I-153 | 556.3 [M + H] |
| 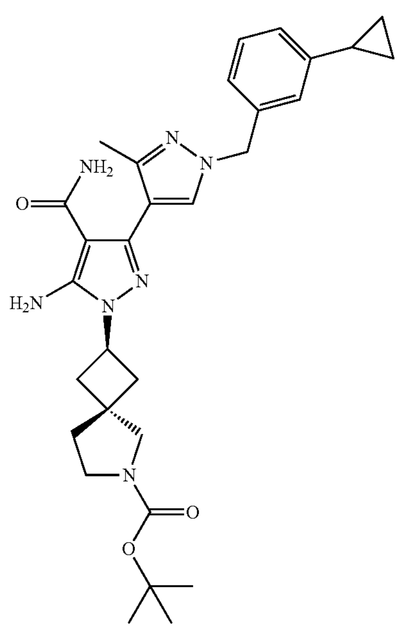 [SMILES: Cc1nn(Cc2cccc(C3CC3)c2)cc1-c1nn([C@H]2C[C@@]3(CCN(C(=O)OC(C)(C)C)C3)C2)c(N)c1C(N)=O] | I-154 | 546.4 [M + H] |

| Structure | Intermediate | m/z |
|---|---|---|
| 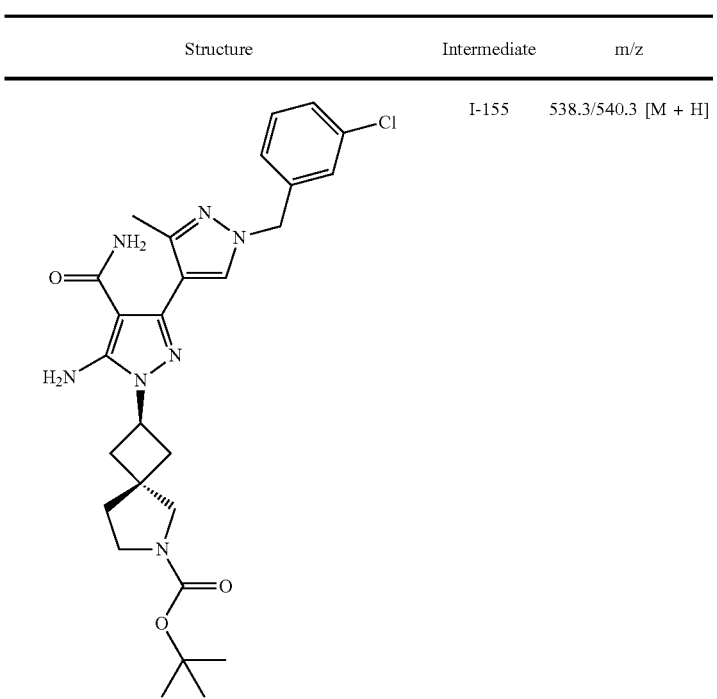 | I-155 | 538.3/540.3 [M + H] |
| 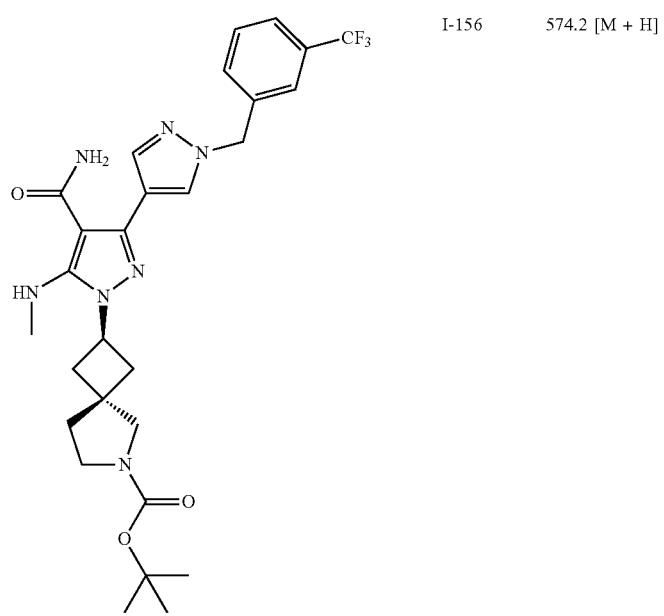 | I-156 | 574.2 [M + H] |

US 9,975,882 B2
167                                                                              168
-continued
| Structure | Intermediate | m/z |
|---|---|---|
| (structure shown) | I-157 | 540 [M + H] |
Method W
Synthesis of Example 1
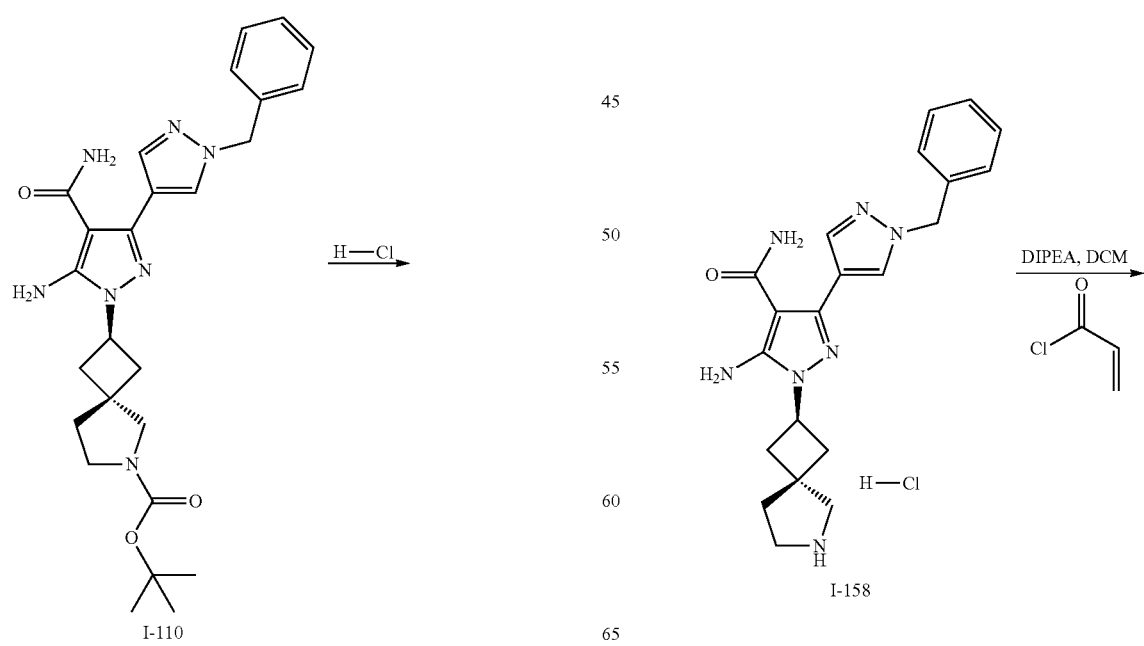

-continued

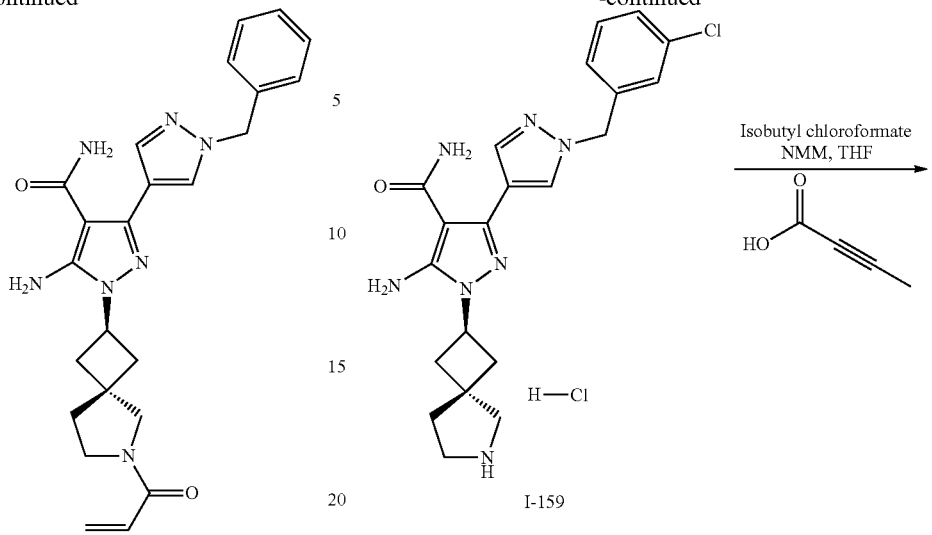

Example 1

I-110 (84 mg, 0.17 mmol) is treated with a 4.0M HCl solution in dioxane (0.427 ml, 1.7 mmol) and stirred at rt for 0.5 h. The reaction is concentrated in vacuo to afford 120 mg of I-158. To a solution of acryloyl chloride (0.03 ml 0.37 mmol) in $CH_2Cl_2$ (5 mL) is added I-158 and DIEA (0.15 mL, 0.84 mmol). After stirring at rt overnight, saturated aqueous ammonium chloride (4 mL) is added and the mixture is extracted with EtOAc (4×20 mL). The combined organic extracts are dried over sodium sulfate, filtered and concentrated in vacuo. The residue is purified by RHPLC (Column: Luna PFP(2) Prep; Gradient: 25% to 30% ACN in Water (0.1% TFA)) to give 5 mg of Example 1.

The following compound is made in similar fashion: Example 26.

Method X
Synthesis of Example 2

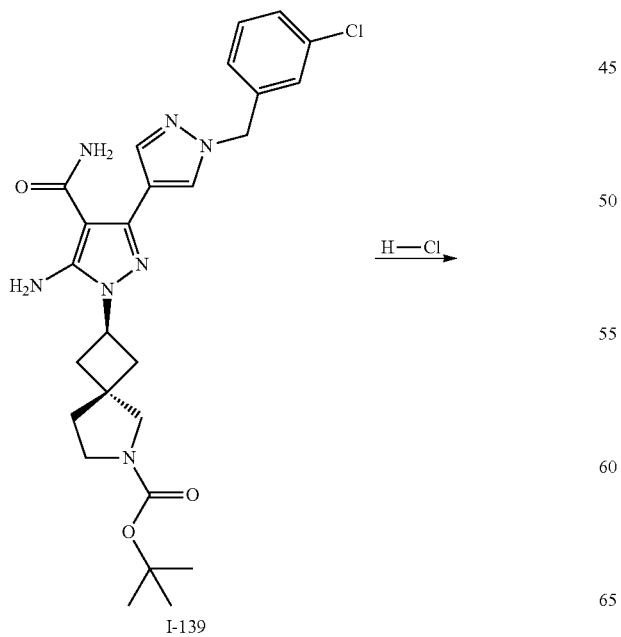

-continued

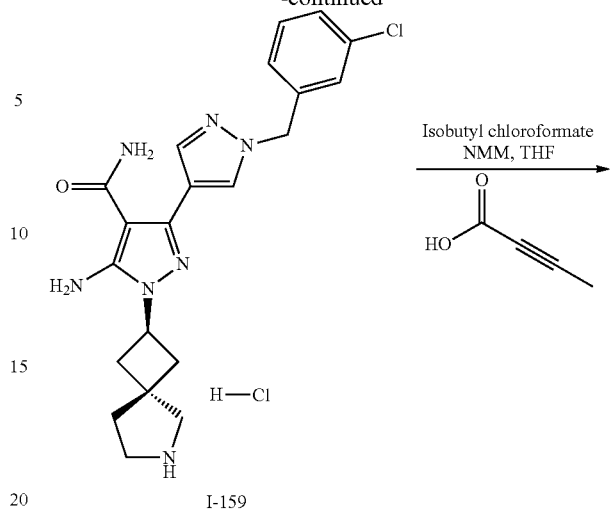

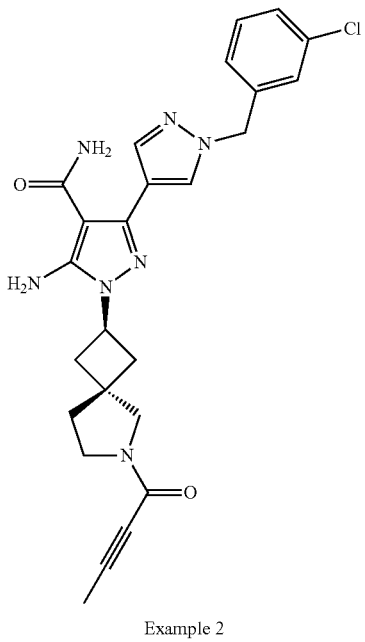

Example 2

To a solution of I-139 (220 mg, 0.42 mmol) in $CH_2Cl_2$ (5 mL) is added a 4.0M HCl solution in dioxane (2.0 ml; 8.0 mmol) and the reaction is stirred at rt for 16 h. The solution is concentrated in vacuo to afford 175 mg of I-159.

To a solution of 2-butynoic acid (35 mg; 0.41 mmol) in THF (5 ml) is added isobutyl chloroformate (62 mg; 0.45 mmol) and N-methylmorpholine (166 mg; 1.6 mmol). The reaction is stirred at rt for 15 min then is transferred to a solution of I-159 (175 mg; 0.41 mmol) in THF (10 mL) and stirred for 1 h at rt. The mixture is then portioned between 10% MeOH in $CH_2Cl_2$ and water and filtered through a phase separator and filtrate is concentrated. The residue is purified by flash chromatography ($SiO_2$, Ethyl acetate in heptane 0-100%, then MeOH in $CH_2Cl_2$ 0-20%) to yield, after concentrating in-vacuo, 127 mg of Example 2.

The following compounds are made in similar fashion: Examples 3-9, 13, 14, 19, 24, 27-29, 34-37, 44, 52-60.

Method Y

Synthesis of Example 12

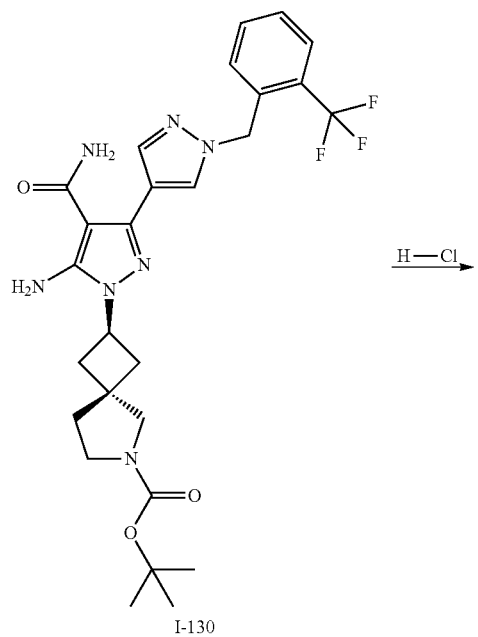

I-130

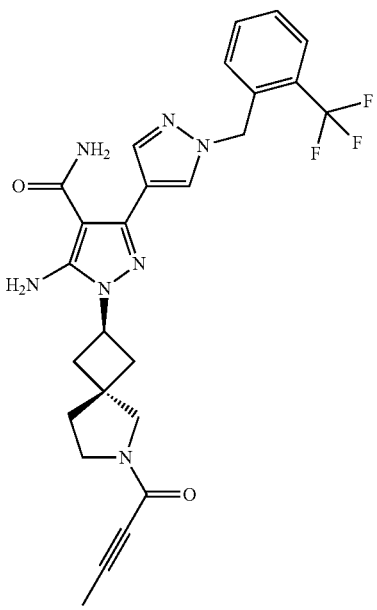

Example 12

To a solution of I-130 (57 g, 102 mmol) in CH$_2$Cl$_2$ (250 mL) is added a 4.0M HCl solution in dioxane (101.9 mL, 407.4 mmol). This reaction solution is allowed to stir at rt for 16 h then concentrated in vacuo to afford 57.5 g of I-160 that is used without further purification.

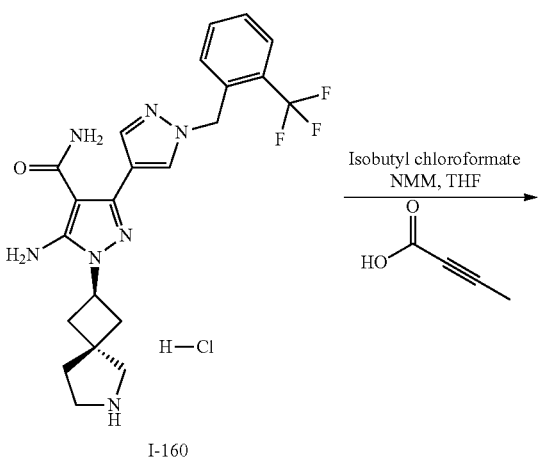

I-160

A solution of 2-butynoic acid (11.6 g, 138 mmol) in IPAc (228 mL) is cooled to 0° C. and isobutyl chloroformate (18 mL, 138 mmol) followed by N-methylmorpholine (50.5 mL, 460 mmol) are added sequentially dropwise. The solution is allowed to stir at 0° C. for 15 min then is transferred to a solution of I-160 (57 g, 115 mmol) in IPAc (200 mL). The reaction mixture is stirred for 1 h then diluted with 300 mL of water and warmed to 50° C. for 3 h, then stirred overnight at rt. The heterogeneous mixture is vacuum filtered and the solid is washed with water, collected and dried to yield 39 g of Example 12. The filtrate is collected and layers are separated. The IPAc layer is concentrated and the residue suspended in EtOAc and heated until a homogeneous solution is observed. The solution is cooled to rt and the resulting precipitate is filtered, collected and dried to yield an additional 8.2 g of Example 12.

Method Z
Synthesis of Example 22

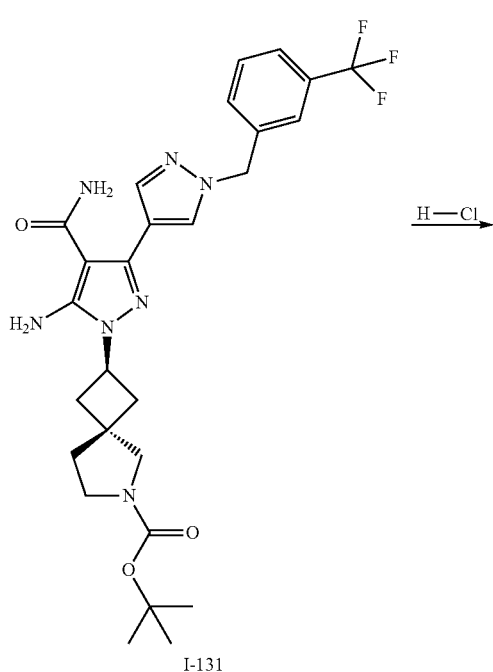

I-131

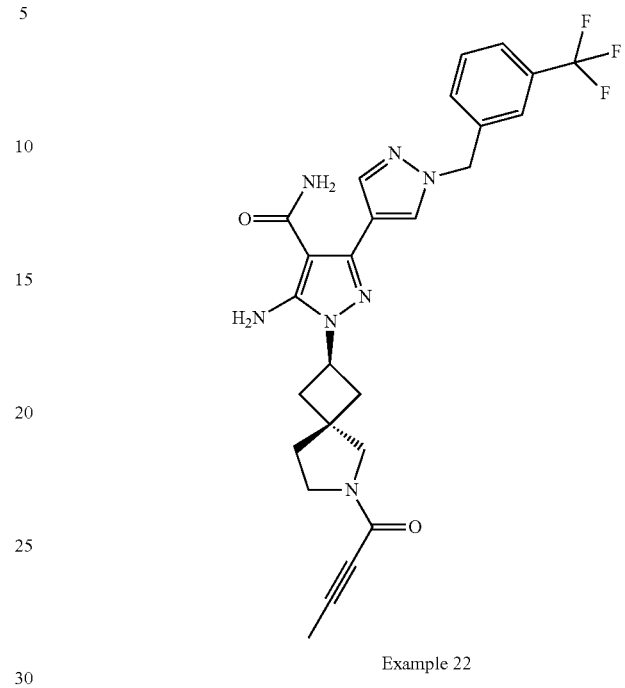

Example 22

To a solution of I-131 (77.4 g, 138.3 mmol) in $CH_2Cl_2$ (250 mL) is added MeOH (50 mL) followed by a 4M HCl solution in dioxane (138.3 mL, 553.3 mmol). This reaction solution is allowed to stir at rt for 4 h and then concentrated in vacuo to yield 69.6 g of I-161 that is used without further purification.

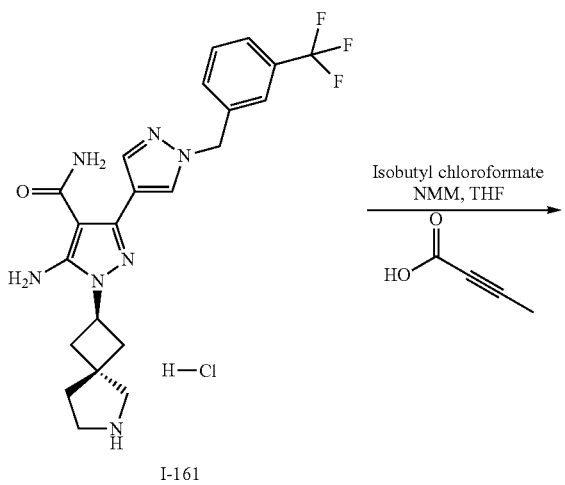

I-161

A solution of 2-butynoic acid (14.3 g, 168.4 mmol) in IPAc (350 mL) is cooled to 0° C. and isobutyl chloroformate (25.4 g, 182.4 mmol) followed by N-methylmorpholine (57.3 g, 561 mmol) are added sequentially dropwise. The solution is allowed to stir at 0° C. for 30 min then is transferred to a solution of I-161 (69.6 g, 140.3 mmol) in IPAc (350 mL). The solution is warmed to rt and stirred for 1 h then diluted with 800 ml of water and warmed to 50° C. for 45 minutes. The mixture is then cooled to rt and stirred for 30 min and then filtered. The solid is collected and dried to yield 55 g of Example 22.

Method AA
Synthesis of Example 25

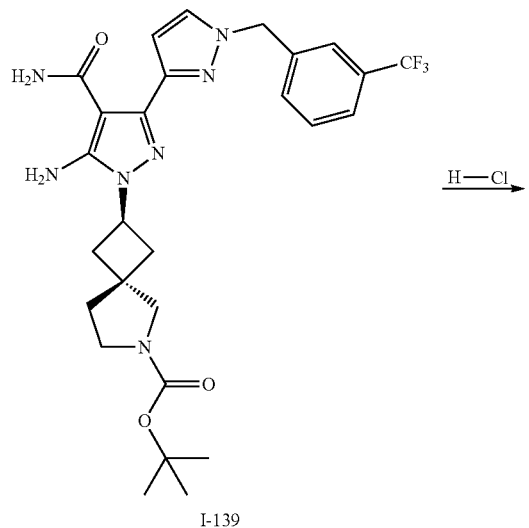

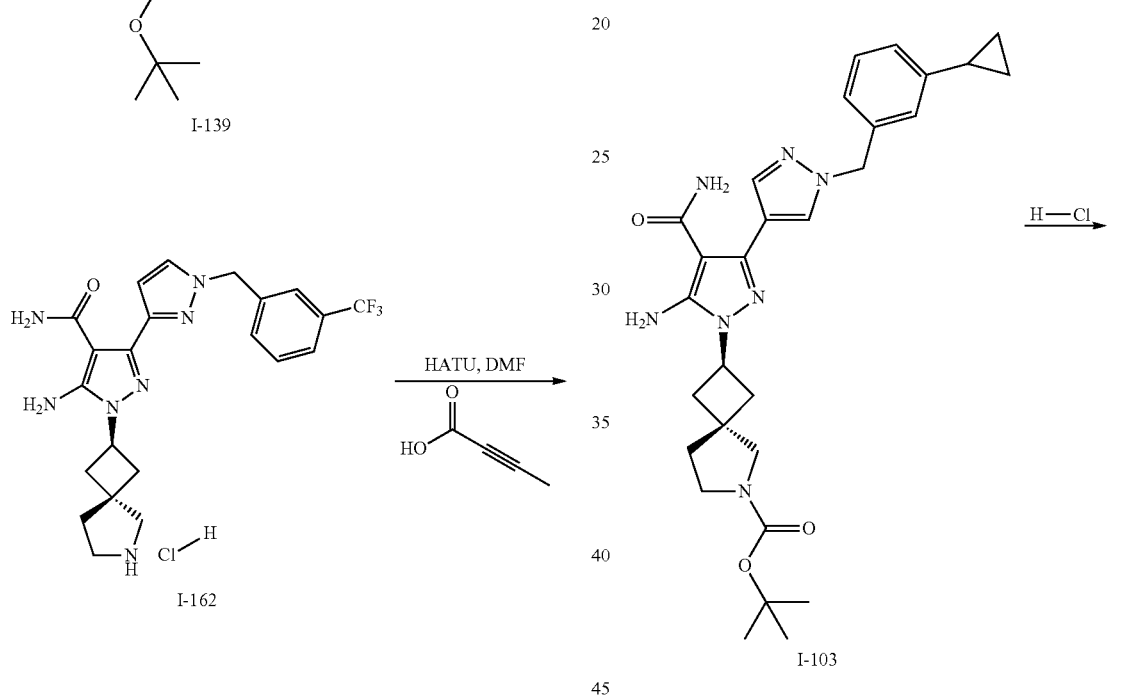

To a solution of I-139 (624 mg, 1.15 mmol) in CH$_2$Cl$_2$ (10 mL) is added a solution of HCl in dioxane (4M, 2.8 mL, 11.5 mmol) dropwise. The solution is decanted and the residue is dried in vacuo to yield 571 mg of I-162. The crude material (I-162) is used without further purification. A solution of I-162 (571 mg, 1.51 mmol) in DMF (10 mL) and DIEA (0.60 mL, 3.4 mmol) is stirred for 15 minutes then 2-butynoic acid (97 mg, 1.51 mmol) and HATU (440 mg, 1.1 mmol) are added. After 30 minutes, saturated aqueous NH$_4$Cl (50 mL) is added, and the mixture is extracted with EtOAc. The organic extract is washed with water and brine, dried over sodium sulfate, filtered and concentrated in vacuo to give a crude residue that is purified by flash chromatography (SiO$_2$, 0-10% MeOH in EtOAc) yielding 55 mg of Example 25.

The following compounds are made in similar fashion: Examples 15-18, 21, 23, 30-33, 38, 39, 40, 41, 51.

Method AB
Synthesis of Example 43

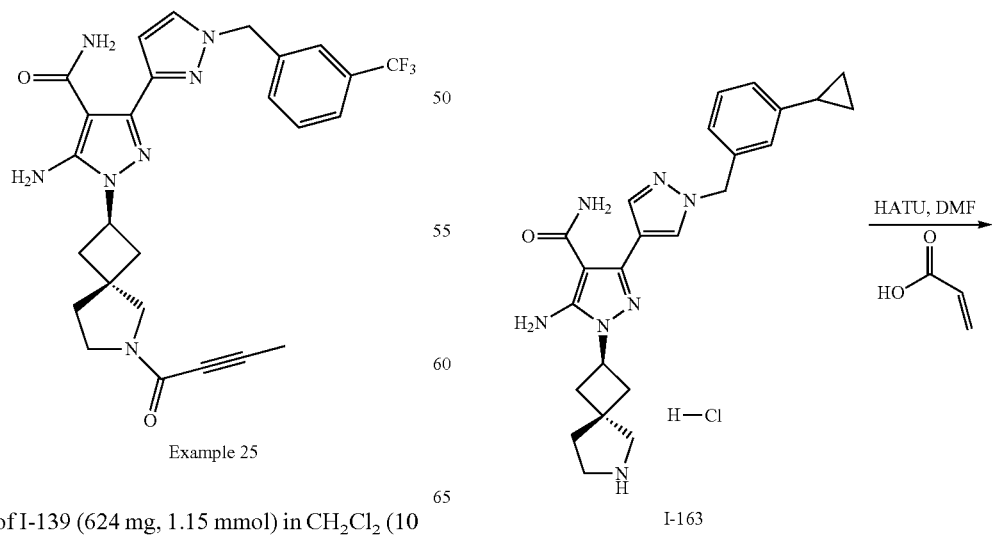

-continued

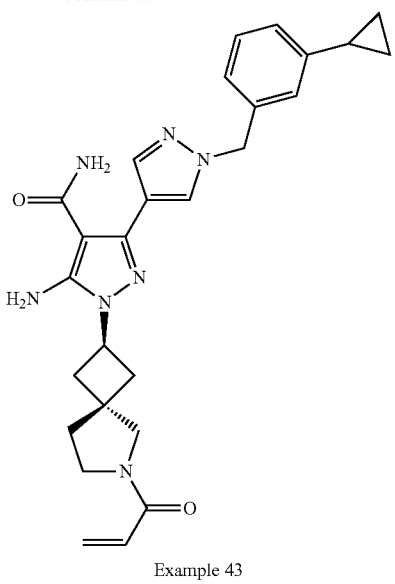

Example 43

To a solution of I-103 (1.2 g, 2.3 mmol) in CH₂Cl₂ (15 mL) is added a HCl solution in dioxane (4M, 5 mL, 20 mmol). The mixture is stirred at rt for 1 h then concentrated in vacuo and the residue is triturated with CH₂Cl₂. The solid is filtered, collected and dried to yield 1.09 g of I-163 that is used without further purification.

To a solution of the acrylic acid (50 mg, 0.69 mmol) and HATU (264 mg, 0.69 mmol) in DMA (2.5 mL) is added I-163 (250 mg, 0.53 mmol) and DIEA (0.47 mL, 2.7 mmol). After stirring at rt overnight, the reaction is concentrated in vacuo to afford a residue that is purified by flash chromatography (SiO₂, 0-10% MeOH in CH₂Cl₂) giving 106 mg of Example 43.

The following compounds are made in similar fashion: Examples 20, 42, 48.

Method AC

Synthesis of Example 45

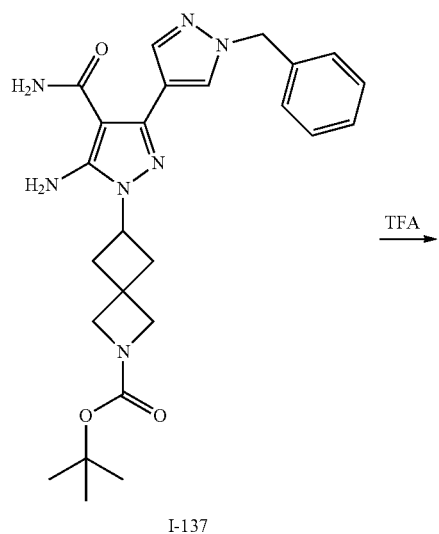

I-137

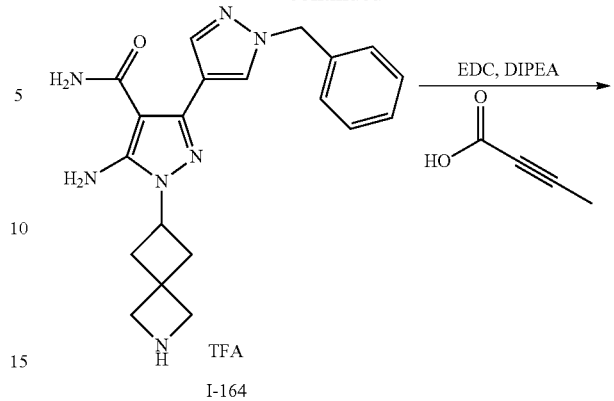

I-164

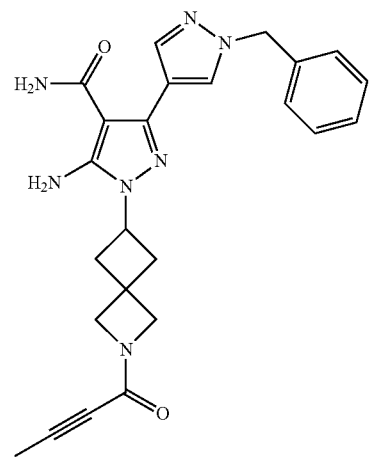

Example 45

To a solution of I-137 (100 mg, 0.21 mmol) in CH₂Cl₂ (5 mL) is added TFA (1.5 mL) and the mixture is stirred at rt overnight. The reaction is concentrated in vacuo to yield I-164 that is used without further purification.

To a solution of the 2-butynoic acid (20 mg, 0.24 mmol) and EDC (78 mg, 0.41 mmol) in DMF (1 mL) is added DIEA (0.12 mL, 0.80 mmol). After 15 min, I-164 (100 mg, 0.27 mmol) is added. After stirring at rt overnight, the reaction is concentrated in vacuo. Purification by RHPLC (10~90%: ACN/H₂O with 0.1% TFA) yielded 9 mg of Example 45.

Method AD
Synthesis of Example 47

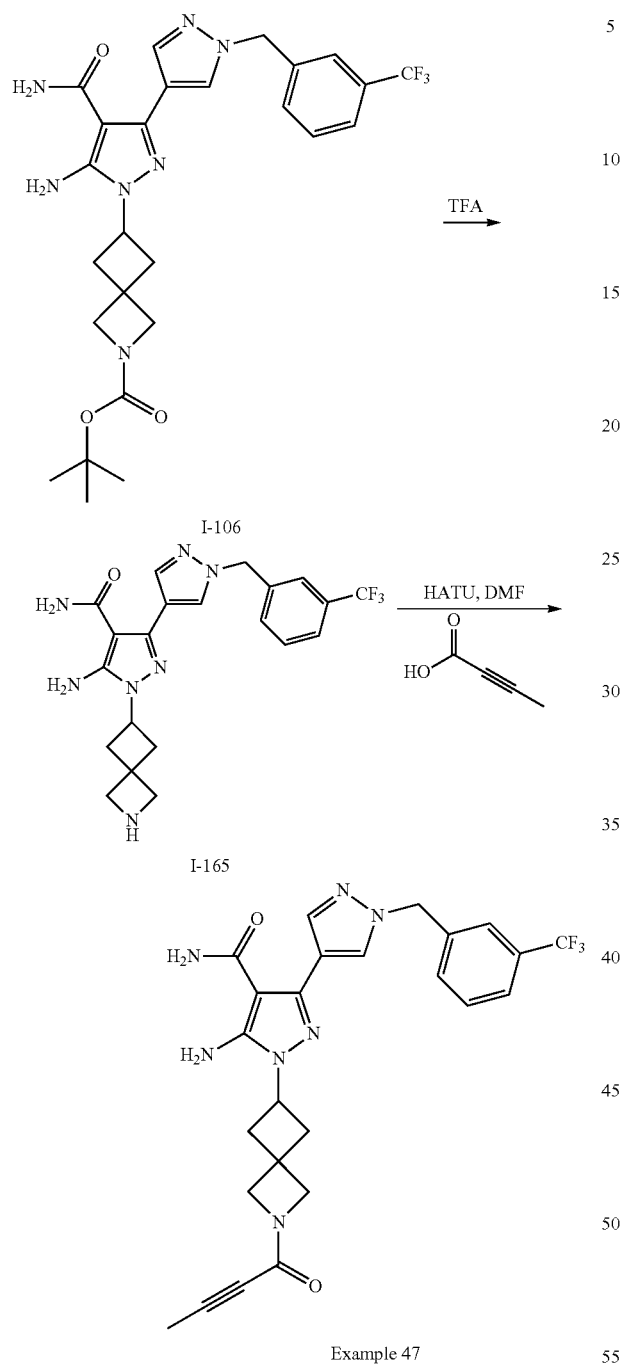

I-106 (87 mg, 0.159 mmol) is dissolved in 5 mL of CH$_2$Cl$_2$. TFA (1 mL) is added and the mixture is stirred at room temperature for 1 hour. The solution is concentrated in vacuo and the residue is dissolved in MeOH and filtered through a 500 mg Agilent StratoSpheres SPE column (MP PL-HCO$_3$). The filtrate is concentrated in vacuo to yield I-165 that is used without further purification.

To a solution of the 2-butynoic acid (17 mg, 0.207 mmol) and HATU (79 mg 0.21 mmol) in DMA (1 mL), is added I-165 (71 mg, 0.159 mmol) and DIEA (0.083 mL, 0.48 mmol). After stirring at rt overnight, saturated aqueous NH$_4$Cl (4 mL) is added and the mixture is extracted with EtOAc (4×20 mL). The combined organic extracts are dried over sodium sulfate, filtered and concentrated in vacuo to afford a residue that is purified by flash chromatography (SiO$_2$, 1-6% MeOH in CH$_2$Cl$_2$) to give 21 mg of Example 47.

The following compounds are made in similar fashion: Examples 46, 49, 50.

Method AE
Synthesis of Example 48

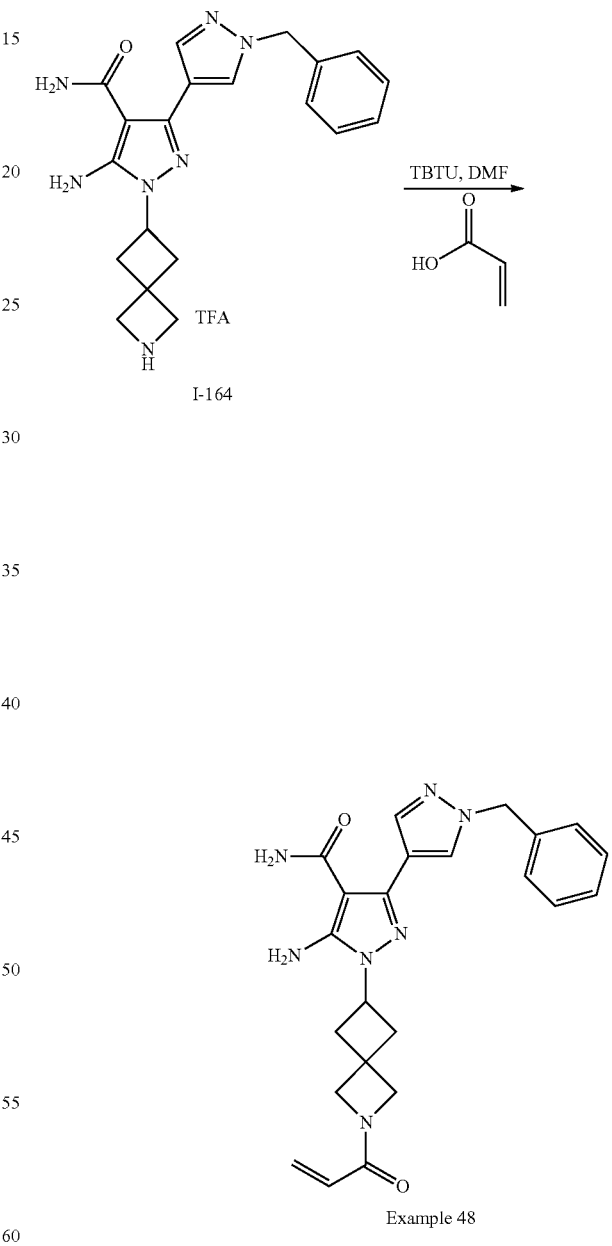

In a vial is placed I-164 (100 mg, 0.27 mmol), acrylic acid (28 mg, 0.4 mmol), TBTU (127 mg, 0.4 mmol) and triethylamine (40 mg, 0.4 mmol) in 1 mL of DMF. After stirring at rt overnight, the solvent is removed in vacuo to provide a residue that is purified by RHPLC (10-80% MeCN/water+ 0.1% TFA) to yield 20 mg of Example 48.

Method AF
Synthesis of Example 11

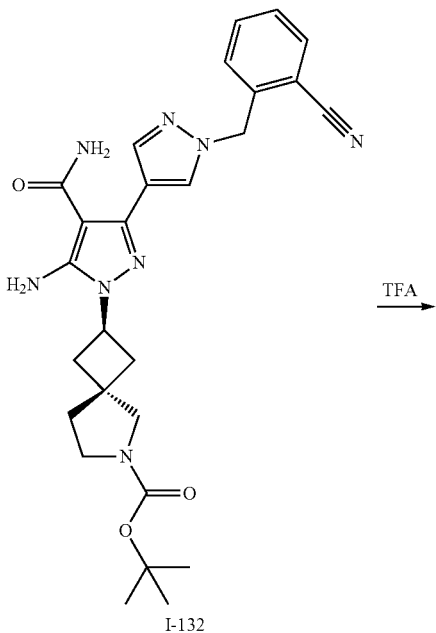

I-132

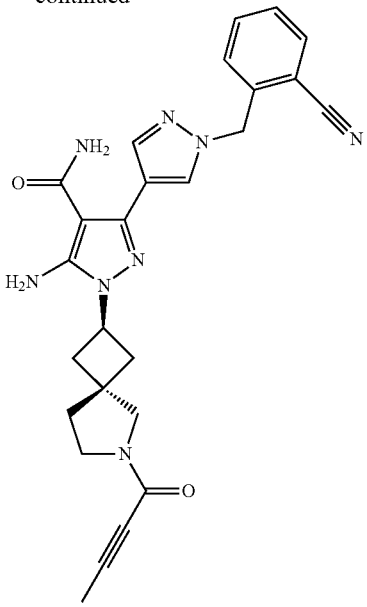

Example 11

To a solution of I-132 (1.0 g, 1.94 mmol) in CH₂Cl₂ (5 mL) is added TFA (3 mL) dropwise. After 3 h at rt, the solvent is removed to provide a residue that is dissolved in MeOH and passed through multiple 500 mg Agilent Strato-Spheres SPE columns (MP PL-HCO₃). The cartridges are washed with MeOH. The filtrate is concentrated in vacuo to provide 806 mg of I-167 that is used without further purification.

To a solution of 2-butynoic acid (197 mg, 2.3 mmol) in EtOAc (10 mL) is added isobutyl chloroformate (350 mg, 2.5 mmol) followed by N-methylmorpholine (0.79 g, 7.7 mmol). The mixture is stirred for 10 min then is added to a solution of I-167 (806 mg, 1.9 mmol) in THF (10 mL) and stirred for 30 min at rt. The reaction is diluted with water and extracted with EtOAc, dried over MgSO₄, filtered, and concentrated. The crude residue is purified by flash chromatography (SiO₂, 0-10% MeOH in CH₂Cl₂) to yield 370 mg of Example 11.

The following compounds are made in similar fashion:
Example 10

Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good inhibitory effect upon BTK.

Such diseases include for example: rheumatoid arthritis, systemic lupus erythromatosis, lupus nephritis, Sjorgen's disease, vasculitis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis and uveitis.

The compounds of formula (I) may be used on their own or in combination with at least one other active substance according to the invention, and/or optionally also in combination with at least one other pharmacologically active substance. The other pharmacologically active substance may be an immunomodulatory agent, anti-inflammatory

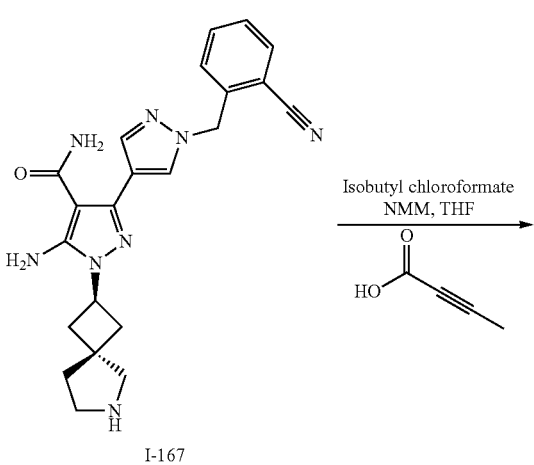

I-167 agent, or a chemotherapeutic agent. Examples of such agents include but are not limited to cyclophosphamide, mycophenolate (MMF), hydroxychloroquine, glucocorticoids, corticosteroids, immunosuppressants, NSAIDs, non-specific and COX-2 specific cyclooxygenase enzyme inhibitors, tumour necrosis factor receptor (TNF) receptors antagonists and methotrexate.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

Description of Biological Properties
BTK v. EGFR Inhibition Assay
BTK Lanthscreen® Eu Kinase Binding Assay:
A Lanthscreen® Eu Kinase Binding assay (Life Technologies) is performed to quantitate the ability of test compounds to bind to BTK. The assay is based on the binding and displacement of Alexa Fluor647-labeled Kinase Tracer #236 to the ATP-binding site of human full length His-tagged BTK (Life Technologies cat #PV3587) with TR-FRET detection using a europium-labeled anti-His antibody. The assay is assembled in 384-well low volume NBS black plates (Corning) where 2 nM BTK and test compound in DMSO at varying concentrations are pre-incubated for 30 min at 28° C. in assay buffer consisting of 50 mM HEPES, pH 7.4, 10 mM MgCl$_2$, 1 mM EGTA. 100 µM Na$_3$VO$_4$ and 0.01% Brij 35. Then, 2 nM of Eu-anti His antibody and 30 nM Kinase Tracer are added and incubated for 60 min at 28° C. Following incubation, TR-FRET signal is read on an Envision plate reader (Excitation: 340 nm; Emissions: 615 and 665 nm). The 665:615 nm emission ratio is calculated and converted to POC compared to control and blank wells.

Inhibition of IL-6 Production in B Cells Co-Stimulated with ODN 2006 and anti-hIgD Primary CD19+ B cells (AllCells #PB010F) are thawed and plated in RPMI containing 10% HI FBS in a 384-well tissue cultured plate at 20,000 cells/well. The cells are treated with test compound (0.5% DMSO final concentration) and incubated for 1 hour at 37° C., 5% CO2. Cells are then stimulated with 5 ug/mL Goat F(ab')2 anti-human IgD (SouthernBiotech #2032) and 2 uM ODN 2006 (InvivoGen #tlrl-2006) and incubated for 18-24 hours at 37° C., 5% CO$_2$. IL-6 in the supernatant is measured using Meso Scale Discovery kit #K211AKB-6.

Inhibition of EGFR Autophosphorylation in A431 Human Epithelial Cells Stimulated with Epithelial Growth Factor A431 cells (ATCC #CRL-1555 FZ) are thawed and plated in DMEM containing 10% FBS in a 384-well tissue culture treated plate at 15,000 cells/well. After incubating for 24 hours at 37° C., 5% $CO_2$, the cells are treated with test compound (1% DMSO final concentration) and incubated for 16 hours at 37° C., 5% $CO_2$. EGF (Millipore, 01-107) is added at a final concentration of 60 ng/mL and incubated for 10 minutes. The medium is removed, the cells are lysed, and phospho EGFR is measured (Meso Scale Diagnostics, N31CB-1).

Representative compounds of the present invention are tested and show BTK inhibition (Table I). Thus, they have the ability to demonstrate clinical benefit for the treatment of autoimmune disorders. Additionally, compounds of the present invention, as represented by examples in Table II, are selective for BTK inhibition over other related kinases. For example, the data presented in Table II demonstrates that the compounds of the present invention possess high degree of BTK selectivity over EGFR. In this table the BTK activity is measured by IL-6 production in primary $CD19^+$ B cells, and the EGFR activity is measured by EGFR phosphorylation in A431 cells.

TABLE II

EGFR selectivity data for representative compounds of the present invention

| Example | B-cell IL-6 $IC_{50}$ (nM) | A431 p-EGFR $IC_{50}$ (nM) |
|---|---|---|
| 2 | 0.3 | >10000 |
| 3 | 1.2 | >10000 |
| 6 | 1.0 | >10000 |
| 7 | 72 | >10000 |
| 8 | 2.5 | >10000 |
| 10 | 1.1 | >10000 |
| 12 | 0.5 | >10000 |
| 14 | 1.1 | >10000 |
| 16 | 2.0 | >10000 |
| 18 | 8.0 | >10000 |
| 19 | 2.3 | >10000 |
| 21 | 9.2 | >10000 |
| 22 | 0.8 | >10000 |
| 23 | 4.5 | >10000 |
| 25 | 6.1 | >10000 |
| 26 | 4.0 | >10000 |
| 27 | 3.4 | >10000 |
| 30 | 2.4 | >10000 |
| 32 | 1.3 | >10000 |
| 33 | 1.2 | >10000 |
| 36 | 0.5 | >10000 |
| 44 | 0.7 | >10000 |
| 47 | 1.1 | >10000 |
| 51 | 1.9 | >10000 |
| 52 | 0.5 | >10000 |
| 53 | 0.4 | >10000 |
| 54 | 0.4 | >10000 |
| 55 | 1.5 | >10000 |
| 56 | 0.7 | >10000 |
| 58 | 3.4 | >10000 |
| 59 | 0.4 | >10000 |
| 60 | 0.6 | >10000 |

Therefore, as can be appreciated by a person skilled in the art, the compounds of the present invention have a lower potential for adverse effects due to off-target activity, as demonstrated by their high selectivity against EGFR in cellular assays.

BTK v. BMX, TEC and TXK Inhibition Assays

Preferred compounds of the present invention display a range of selective inhibition of BTK over other related kinases BMX, TEC, and TXK relative to known BTK inhibitors. The following are used as test compounds: compounds of the present invention and 1-[(3R)-3-[4-amino-3-(4-phenoxyphenyl)pyrazolo[3,4-d]pyrimidin-1-yl]-1-piperidyl]prop-2-en-1-one (comparative compound A, ibrutinib), 5-amino-1-(7-but-2-ynoyl-7-azaspiro[3.4]octan-2-yl)-3-(4-isopropoxyphenyl) pyrazole-4-carboxamide (comparative compound B, Example 168 WO2014/025976), N-(3-(5-fluoro-2-(4-(2-methoxyethoxy)phenylamino)pyrimidin-4-ylamino) phenyl)acrylamide (comparative compound C, *Journal of Pharmacology and Experimental Therapeutics* 2013, 346:219-228) which are known BTK inhibitors.

BTK, BMX, and TXK Assays

Z'-LYTE™ Assay (Life Technologies):

The Z'-Lyte assay employs a FRET-based, coupled-enzyme format and is based on the differential sensitivity of phosphorylated and non-phosphorylated peptides to proteolytic Cleavage. The activity of human recombinant BTK (full length, His-tagged), BMX (full length, His-tagged) or Txk (full length, GST-tagged) is estimated by measuring the phosphorylation of a synthetic FRET peptide substrate labeled with Coumarin and Fluorescein. The 10 µL assay mixtures contain 50 mM HEPES (pH 7.5), 0.01% Brij-35, 10 mM $MgCl_2$, 1 mM EGTA, 2 µM FRET peptide substrate (Z'-LYTE™ Tyr 1 Peptide for BTK and BMX, and Tyr 06 peptide for TXK), and kinase (1.3-9.3 ng BTK; 2.8-45.0 ng BMX; 2.3-93.6 ng TXK). Incubations are carried out at 22° C. in black polypropylene 384-well plates (Corning). Prior to the assay, kinase, FRET peptide substrate and serially diluted test compounds are pre-incubated together in assay buffer (7.5 µL) for 10 min, and the assay is initiated by the addition of 2.5 µL assay buffer containing 4×ATP (25 µM for BTK; 100 µM for both BMX and TXK). Following the 60 min incubation, the assay mixtures are quenched by the addition of 5 µL of Z'-LYTE™ development reagent, and 1 hour later the emissions of Coumarin (445 nm) and Fluorescein (520 nm) are determined after excitation at 400 nm using an Envision plate reader. An emission ratio (445 nm/520 nm) is determined to quantify the degree of substrate phosphorylation.

TEC Assay

Lanthscreen® Eu Kinase Binding Assay (Life Technologies):

Lanthscreen® Eu Kinase Binding assay for BMX is performed as described above for BTK except that 1 nM human recombinant full length TEC (His-tagged) kinase and 1 nM Alexa Fluor647-labeled Kinase Tracer #178 were used instead.

Representative compounds of the present invention are assessed for inhibition of BTK, BMX, and TXK measuring phosphorylation of a substrate (Z'-LYTE™ assay, Life Technologies) and TEC measuring displacement of a "tracer" (Lanthscreen® Eu Kinase Binding assay, Life Technologies).

TABLE III

BMX, TEC and TXK selectivity for compounds of the present invention

| Example | BTK $IC_{50}$ (nM) | BMX $IC_{50}$ (nM) | TEC $IC_{50}$ (nM) | TXK $IC_{50}$ (nM) |
|---|---|---|---|---|
| Compound A | 1.4 | 0.8 | 12 | 2.3 |
| Compound B | 0.9 | 2.2 | 44 | 2.3 |
| Compound C | 6.1 | 3.2 | 6.8 | 22 |
| 2 | 0.8 | 16 | 14 | 25 |
| 3 | 1.2 | 17 | 45 | 27 |
| 6 | 1.5 | 33 | 65 | 43 |
| 7 | 29 | 870 | 1200 | 630 |
| 8 | 4.4 | 85 | 130 | 120 |
| 10 | 1.4 | 50 | 120 | 100 |

TABLE III-continued

BMX, TEC and TXK selectivity for compounds of the present invention

| Example | BTK $IC_{50}$ (nM) | BMX $IC_{50}$ (nM) | TEC $IC_{50}$ (nM) | TXK $IC_{50}$ (nM) |
|---|---|---|---|---|
| 11 | 1.8 | 37 | 73 | 150 |
| 12 | 1.7 | 21 | 92 | 130 |
| 14 | 1.7 | 150 | 92 | 180 |
| 16 | 13 | 160 | 220 | 430 |
| 18 | 3.1 | 120 | 110 | 270 |
| 19 | 5.0 | 290 | 160 | 220 |
| 21 | 40 | 3000 | 1100 | 1900 |
| 22 | 0.7 | 29 | 21 | 46 |
| 23 | 8.3 | 280 | 130 | 600 |
| 25 | 19 | 300 | 160 | 850 |
| 26 | 18 | 1200 | 430 | 3000 |
| 27 | 6.6 | 120 | 66 | 120 |
| 28 | 1.2 | 56 | 39 | 95 |
| 29 | 3.6 | 78 | 79 | 92 |
| 30 | 3.0 | 120 | 64 | 160 |
| 32 | 1.9 | 64 | 49 | 55 |
| 33 | 1.3 | 25 | 48 | 59 |
| 36 | 1.0 | 37 | 22 | 50 |
| 44 | 1.4 | 24 | 20 | 78 |
| 47 | 2.7 | 500 | 34 | 310 |
| 51 | 0.8 | 8.0 | 18 | 12 |
| 52 | 7.0 | 160 | 100 | 260 |
| 53 | 1.3 | 34 | 47 | 84 |
| 54 | 1.5 | 27 | 35 | 110 |
| 55 | 2.5 | 35 | 67 | 79 |
| 56 | 2.2 | 54 | 120 | 150 |
| 58 | 2.6 | 46 | 38 | 67 |
| 59 | 0.8 | 38 | 36 | 68 |
| 60 | 1.7 | 27 | 35 | 100 |

These results show that the compounds of the present invention are selective for BTK inhibition as compared to other kinases by at least about 10 folds. See Table III In-Vivo Assay—Comparison Between the Compounds of the Present Invention and Comparative Compounds A, B and C In a side-by-side in-vivo study, select compounds of the present invention and comparative compounds A-C are evaluated in telemetry-instrumented conscious rats to determine their effects on mean arterial pressure (MAP) at doses at or above therapeutically relevant concentrations. The following compounds are evaluated at 10 mg/kg po qd and 30 mg/kg po qd over the course of five days: Examples 12 and 22 of the present invention and comparative compounds A-C, i.e., 1-[(3R)-3-[4-amino-3-(4-phenoxyphenyl)pyrazolo[3,4-d]pyrimidin-1-yl]-1-piperidyl]prop-2-en-1-one (comparative compound A, ibrutinib), 5-amino-1-(7-but-2-ynoyl-7-azaspiro[3.4]octan-2-yl)-3-(4-isopropoxyphenyl) pyrazole-4-carboxamide (comparative compound B, Example 168 WO2014/025976) and N-(3-(5-fluoro-2-(4-(2-methoxyethoxy)phenylamino)pyrimidin-4-ylamino) phenyl)acrylamide (comparative compound C, *Journal of Pharmacology and Experimental Therapeutics* 2013, 346:219-228).

Experimental Protocol

All animals (telemetry-instrumented) are single housed in metabolic cages. Rats are acclimated to the metabolic cage for at least 3 days and then dosed with vehicle for up to 4 days. Blood pressure, heart rate, and bodyweight are collected during the baseline period and animals are randomized into 3 groups based on these parameters (n=8-9/group). Treatment groups are: vehicle and test compound (10 mg/kg po and 30 mg/kg po qd); animals are treated with compound for 5 days. The following day, rats are dosed again with the test compound and plasma samples are collected via tail bleed for compound exposures at multiple timepoints post-dose to capture the $T_{max}$ (n=3-9/group). Mean arterial pressure (MAP) and heart rate (HR) are collected continuously throughout the study. Statistical analyses is performed using GraphPad Prism based on the average 24-hr mean value during five days of compound administration (one-way ANOVA with Dunnett's post-test vs. Vehicle; $p<0.05$ is considered statistically significant).

TABLE IV

| Example | Dose (mg/kg) | $C_{max}$ (nM) Day 6 | 5-Day 24-h MAP (mmHg) Change versus Control |
|---|---|---|---|
| Example 12 | 10 | 111 ± 37 | No statistically significant effect on MAP |
| Example 12 | 30 | 344 ± 106 | No statistically significant effect on MAP |
| Compound A | 10 | 319 ± 36 | 3 ± 1 mmHg |
| Compound A | 30 | 561 ± 183 | 4 ± 1 mmHg |
| Compound B | 10 | 182 ± 17 | 3 ± 1 mmHg |
| Compound B | 30 | 480 ± 53 | 2 ± 1 mmHg |
| Compound C | 10 | 644 ± 96 | 4 ± 1 mmHg |
| Compound C | 30 | 1731 ± 434 | 5 ± 1 mmHg |
| Example 22 | 10 | 170 ± 29 | No statistically significant effect on MAP |
| Example 22 | 30 | 720 ± 262 | No statistically significant effect on MAP |

The results show that the compounds of the present invention, e.g., Examples 12 and 22, elicit no effect on MAP in rats as compared to the comparative compounds A, B and C. As can be appreciated by a person skilled in the art, significant changes in the mean arterial pressure in rats could be indicative of higher risk of adverse cardiovascular events in a clinical setting. Therefore, the fact that the compounds of the present invention do not display statistically significant effects on MAP is surprising and unexpected. See Table IV and FIG. 1.

All patent and non-patent documents or literature cited in this application are herein incorporated by reference in their entirety.

The invention claimed is:
1. A compound of the formula (I)

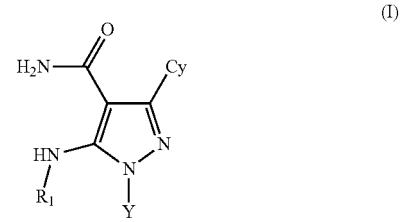

wherein:
Cy is chosen from

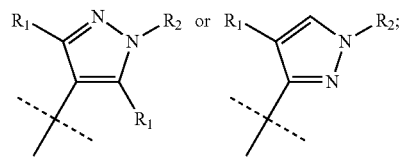

each $R_1$ is independently chosen from hydrogen or methyl;

R₂ is L-Ar, wherein Ar is phenyl or pyridinyl and each is optionally substituted by one or more of halogen, halo C₁₋₄ alkyl, C₁₋₄ alkyl, C₁₋₄ alkoxy, —CN, halo C₁₋₄ alkoxy, or cycloalkyl;

L is —(CH₂)— or —(CHCH₃)—;

Y is C₆-C₈ spirocycle containing 1 ring nitrogen atom, and is substituted by one R₃;

R₃ is chosen from

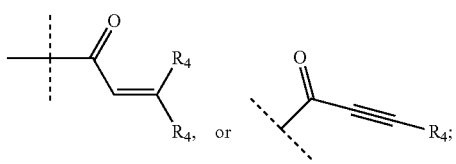

and
each R₄ is independently chosen from hydrogen, C₁₋₄ alkyl, or C₃₋₄ cycloalkyl;
each group defined above for R₁-R₄ and Y can be where possible partially or fully halogenated;
or a pharmaceutically acceptable salt or hydrate thereof.

2. The compound according to claim 1, wherein
Y is chosen from

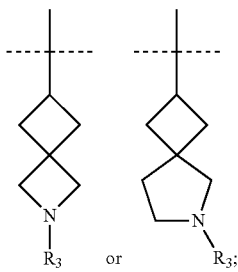

or a pharmaceutically acceptable salt or hydrate thereof.

3. The compound according to claim 1, wherein
Cy is

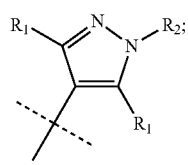

Y is chosen from

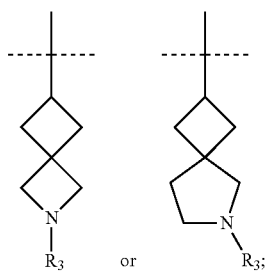

wherein R₃ is

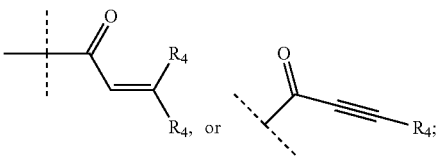

and
each R₄ is independently chosen from hydrogen, C₁₋₄ alkyl, or C₃₋₄ cycloalkyl;
or a pharmaceutically acceptable salt or hydrate thereof.

4. The compound according to claim 1, wherein
Cy is

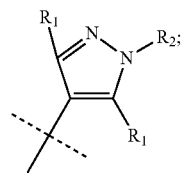

Y is chosen from

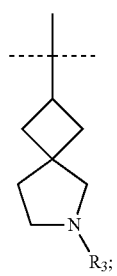

wherein R₃ is

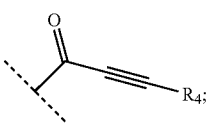

and
R₄ is chosen from hydrogen, C₁₋₄ alkyl, or C₃₋₄ cycloalkyl;
or a pharmaceutically acceptable salt or hydrate thereof.

5. The compound according to claim 1, wherein
Cy is

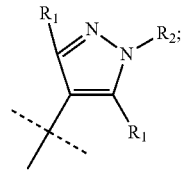

Y is chosen from

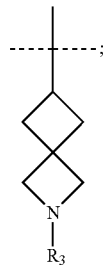

R₃ is

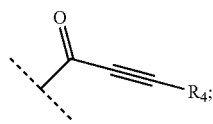

and
R₄ is chosen from hydrogen, C₁₋₄ alkyl, or C₃₋₄ cycloalkyl;
or a pharmaceutically acceptable salt or hydrate thereof.

6. The compound according to claim 1 and wherein Cy is

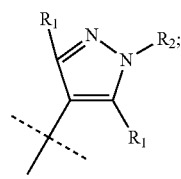

Y is chosen from

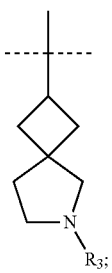

wherein R₃ is

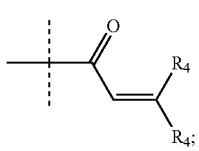

and
each R₄ is independently chosen from hydrogen, C₁₋₄ alkyl, or C₃₋₄ cycloalkyl;
or a pharmaceutically acceptable salt or hydrate thereof.

7. The compound according to claim 1, wherein Cy is

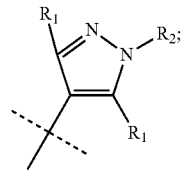

Y is chosen from

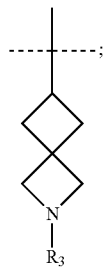

wherein R₃ is

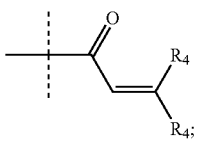

and
each R₄ is independently chosen from hydrogen, C₁₋₄ alkyl, or C₃₋₄ cycloakyl;
or a pharmaceutically acceptable salt or hydrate thereof.

8. The compound according to claim 1, wherein each R₄ is independently chosen from hydrogen, methyl, or cyclopropyl;
or a pharmaceutically acceptable salt or hydrate thereof.

9. The compound according to claim 1, wherein R₂ is L-Ar, wherein Ar is phenyl or pyridinyl and each is optionally substituted by one or more of halogen, halomethyl, methyl, methoxy, —CN, halomethoxy, or cyclopropyl;
L is —(CH₂)— or —(CHCH₃)—
or a pharmaceutically acceptable salt or hydrate thereof.

10. A compound chosen from:
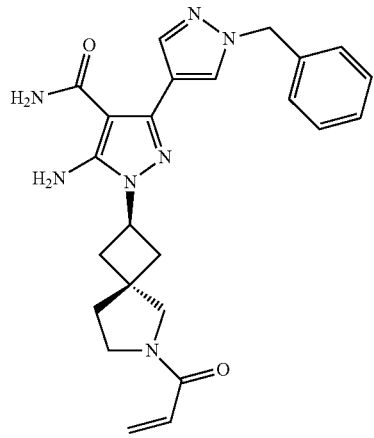
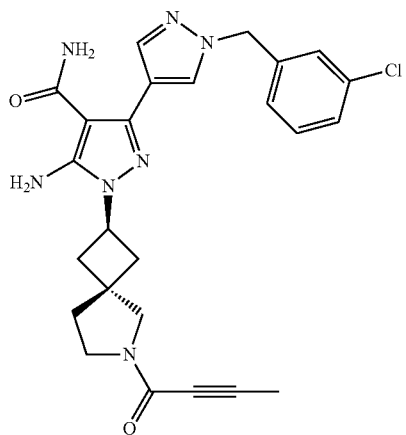
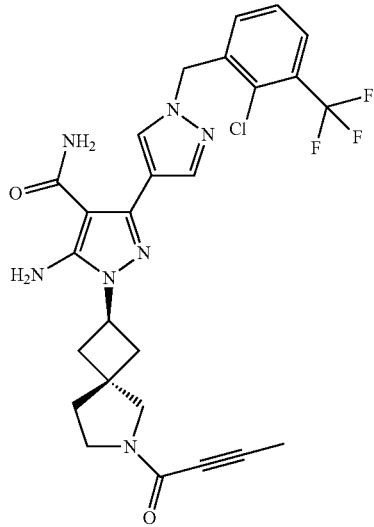
-continued
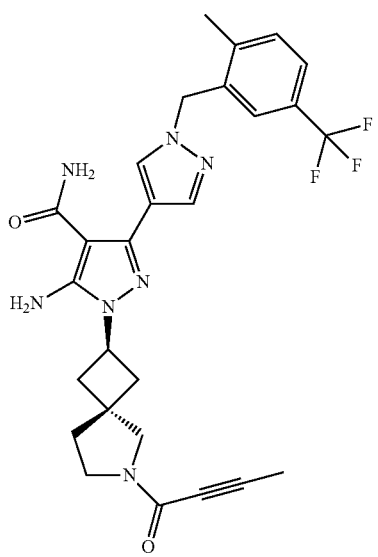
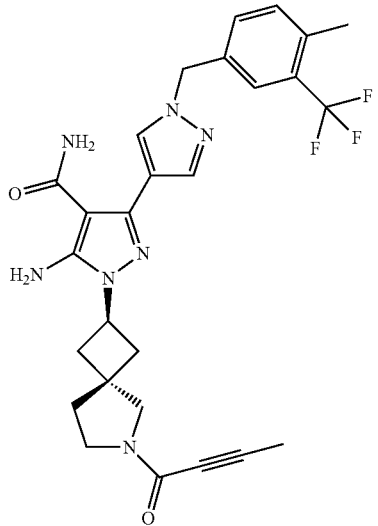
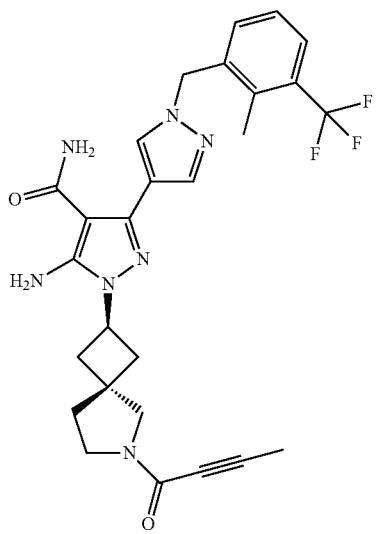

195
-continued
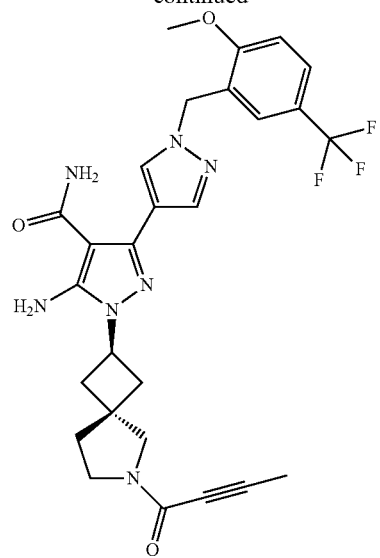
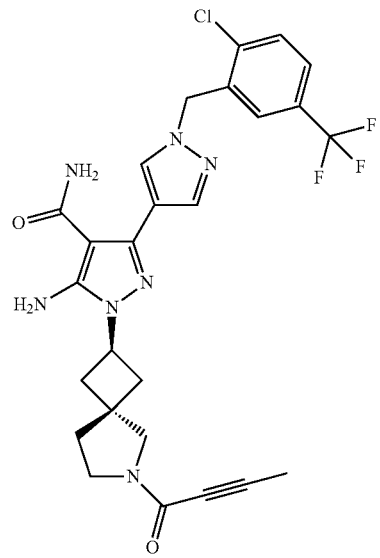
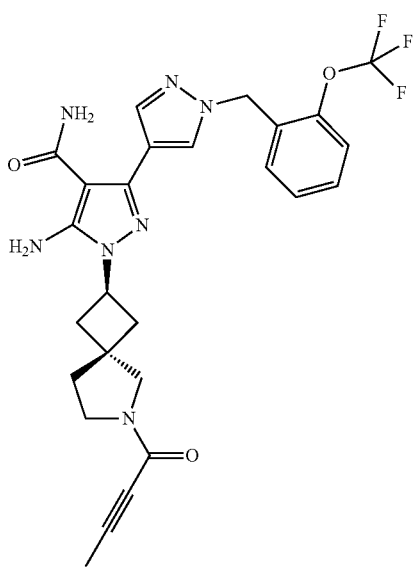
196
-continued
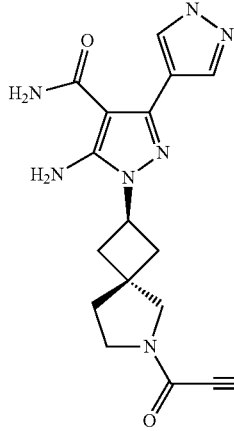
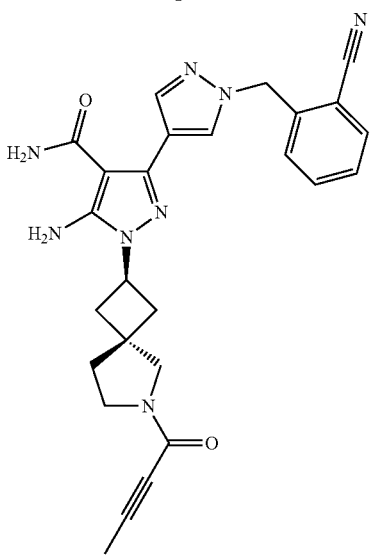
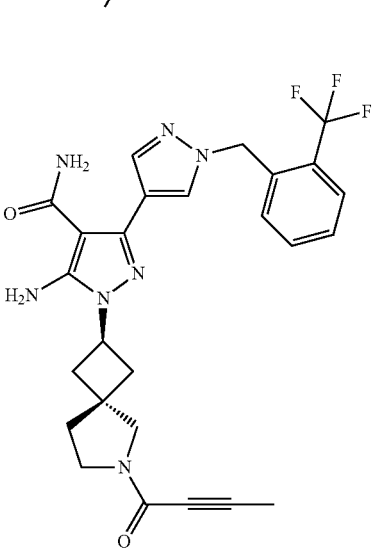

197
-continued
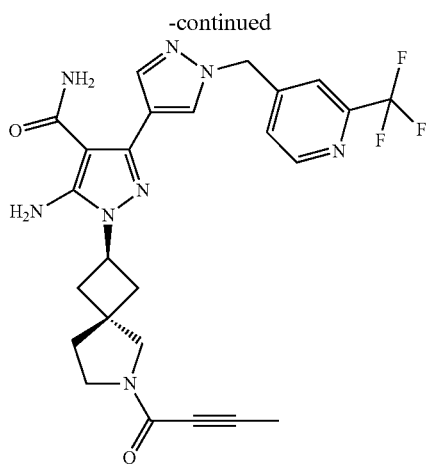
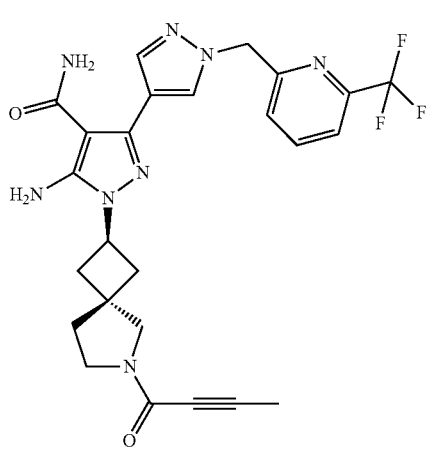
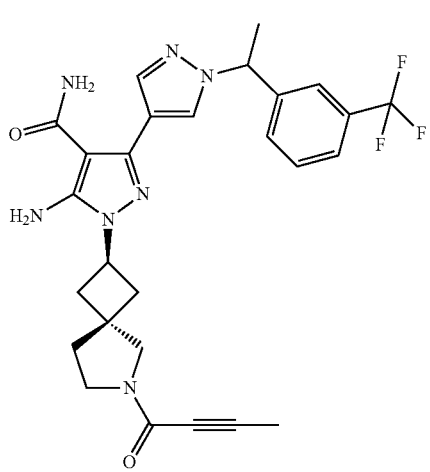
198
-continued
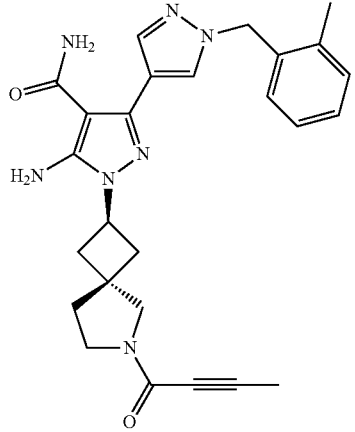
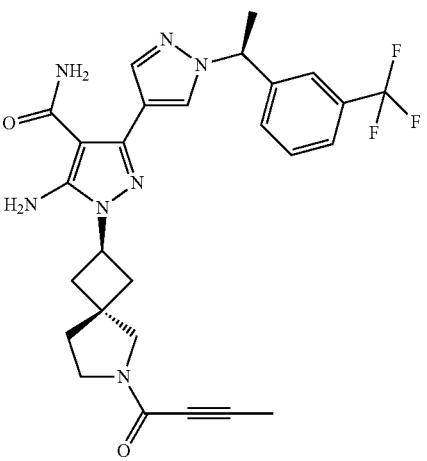
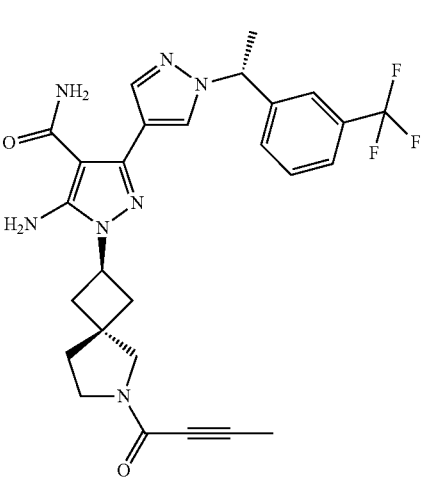

199
-continued
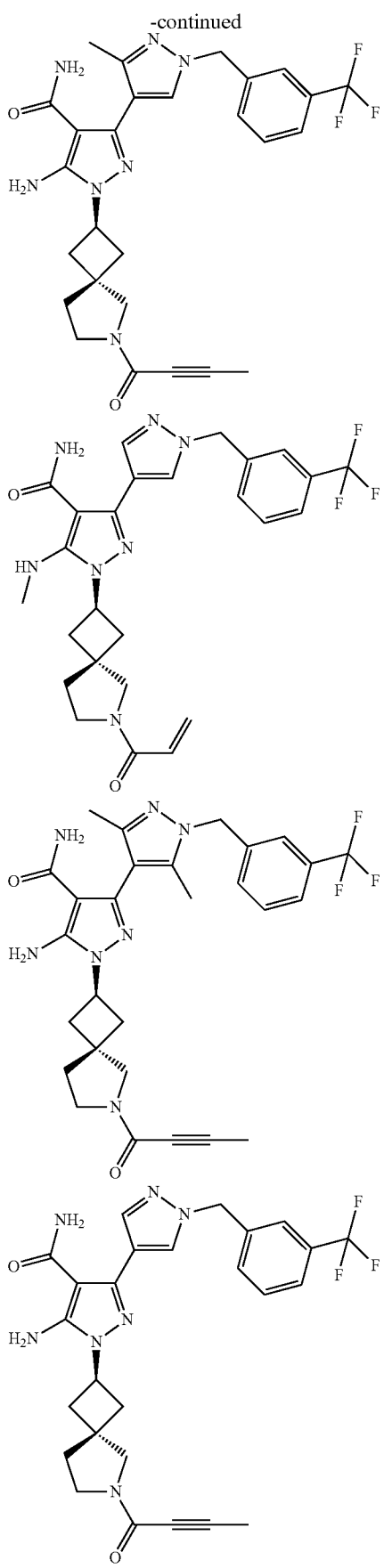
200
-continued
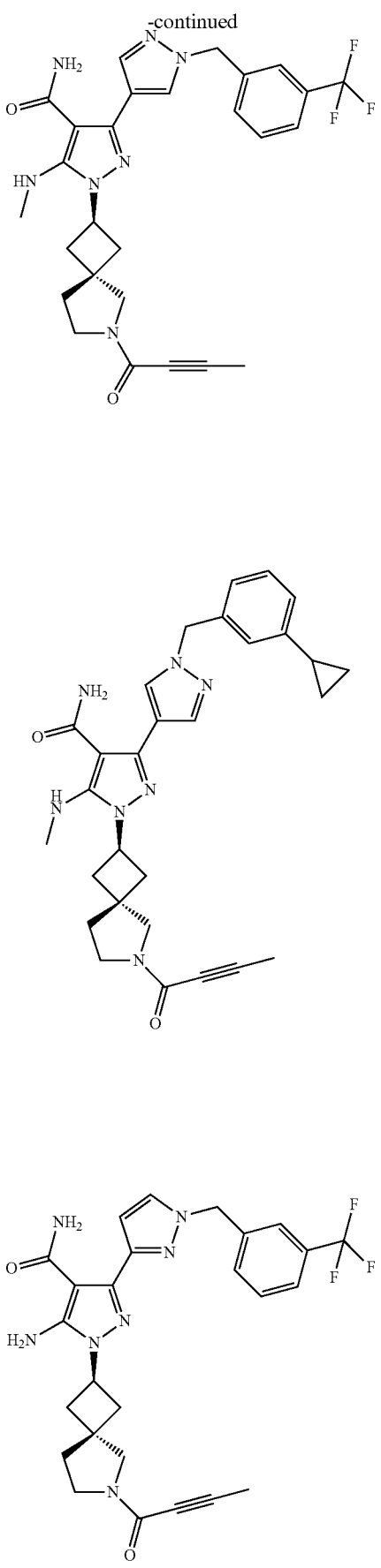

-continued
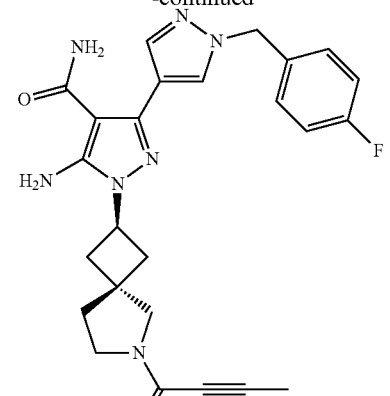
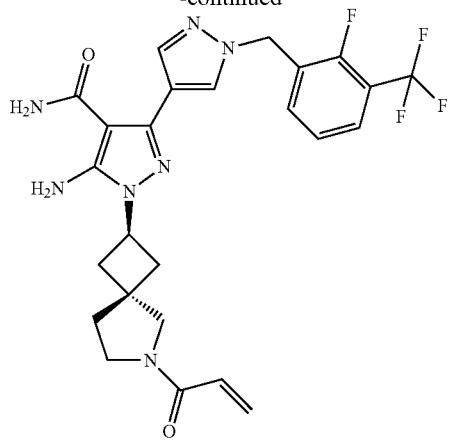
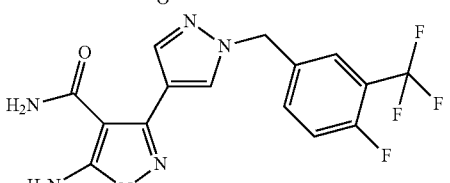
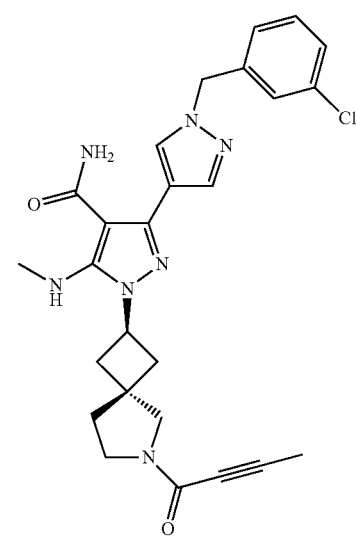
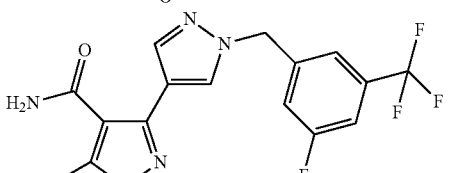
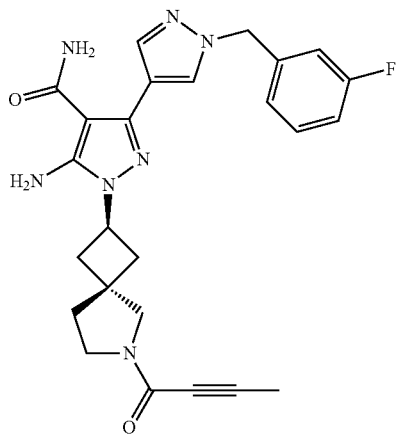
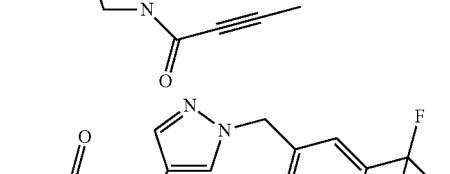
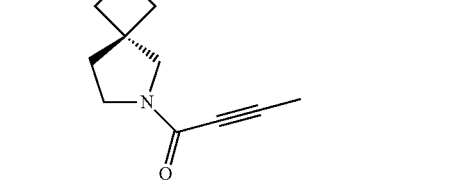

203
-continued
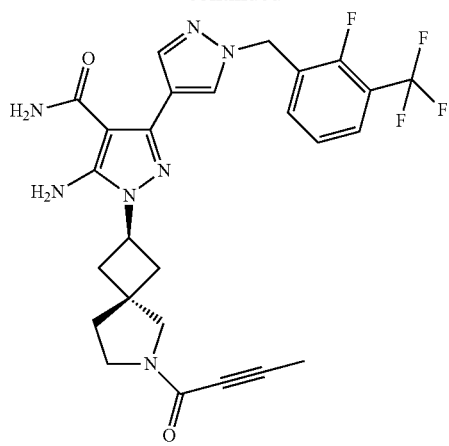
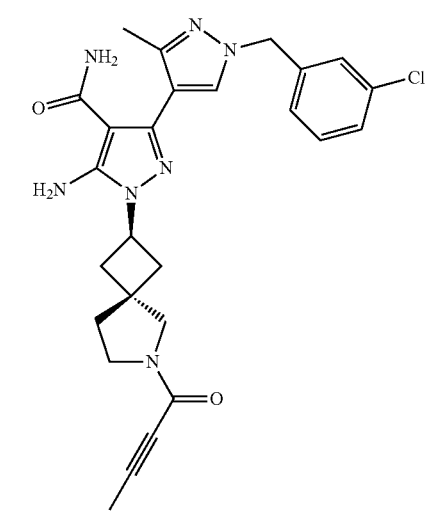
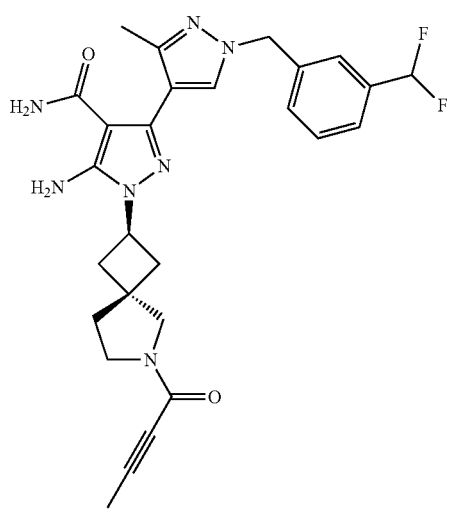
204
-continued
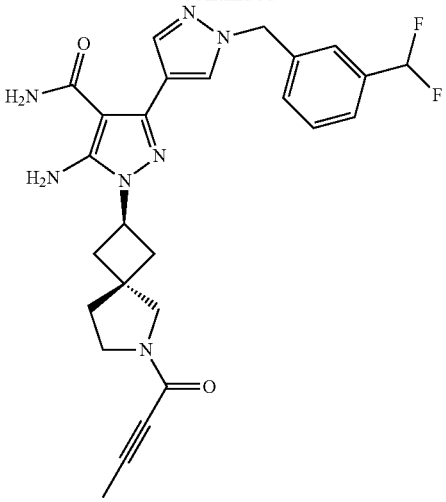
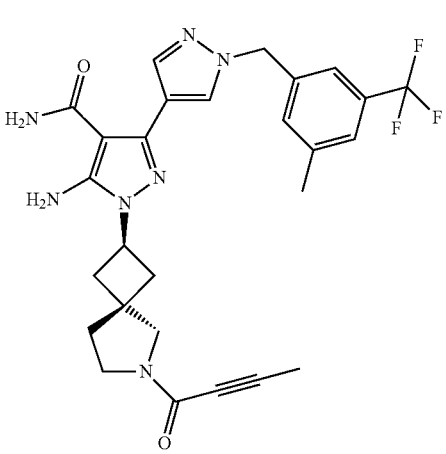

205
-continued
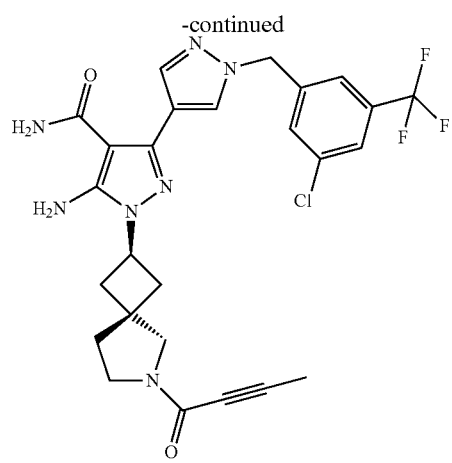
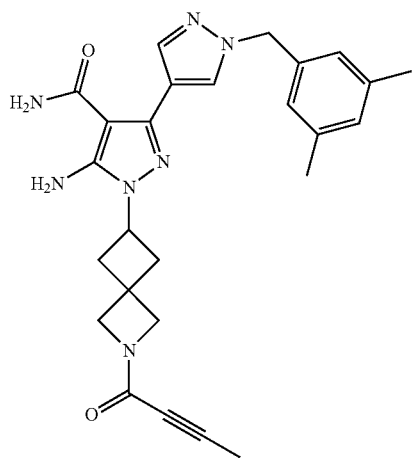
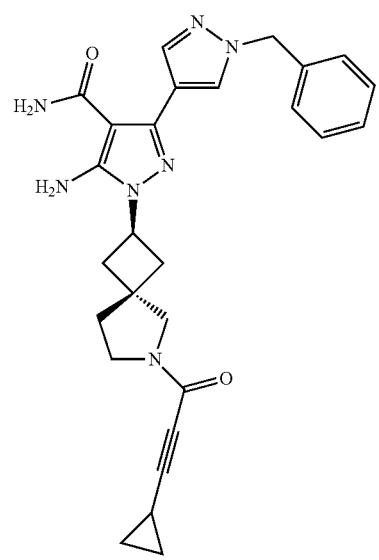
206
-continued
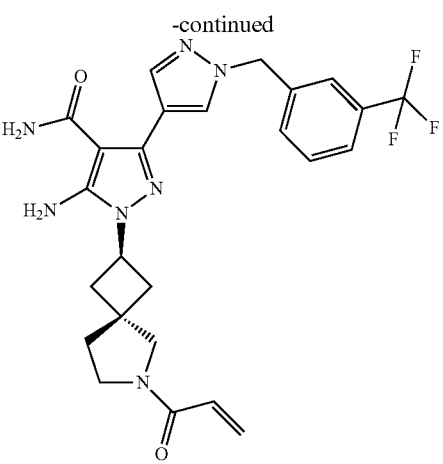
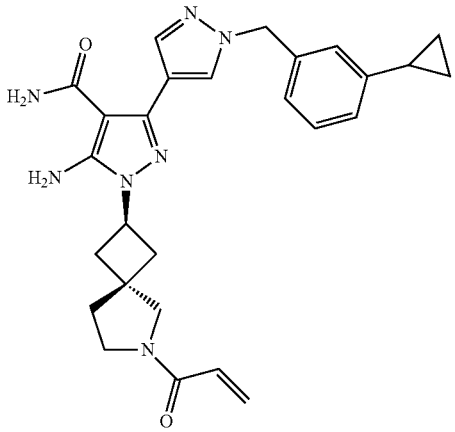
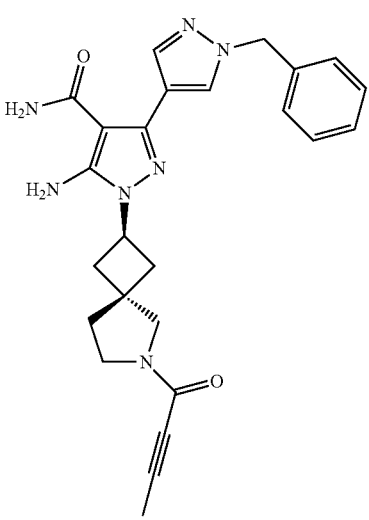

207
-continued
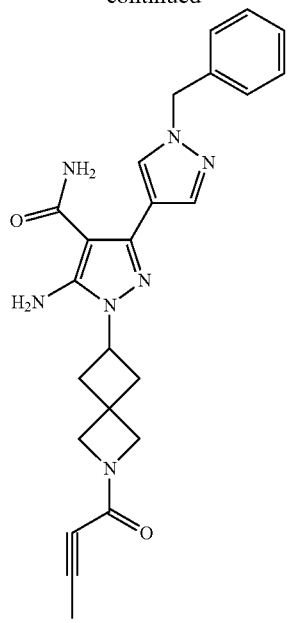
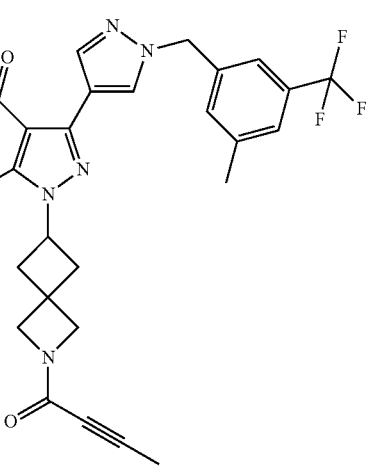
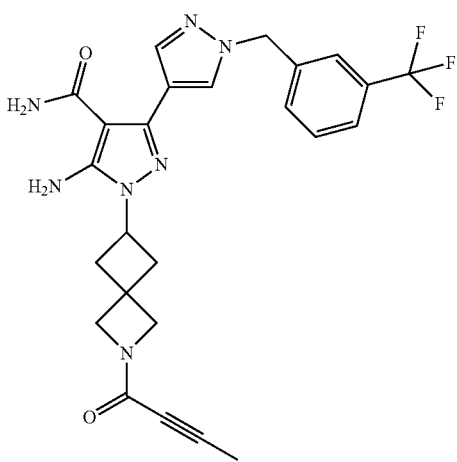
208
-continued
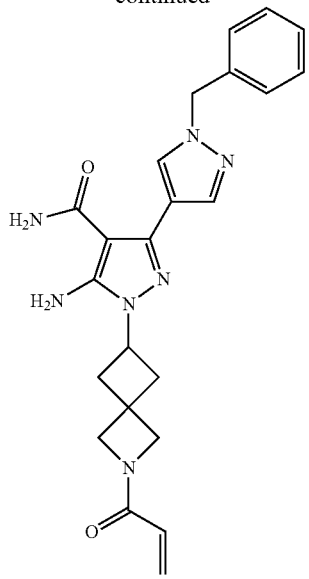
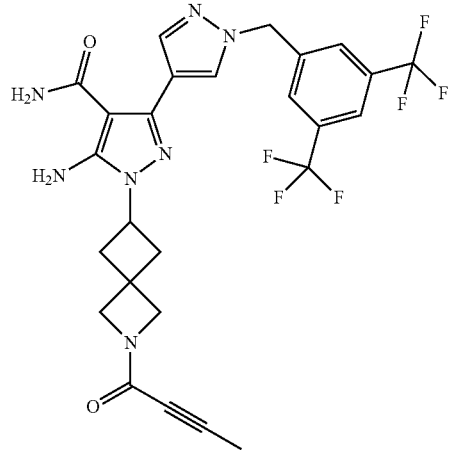
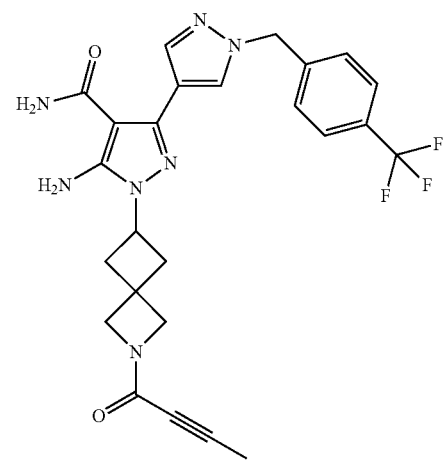

209
-continued
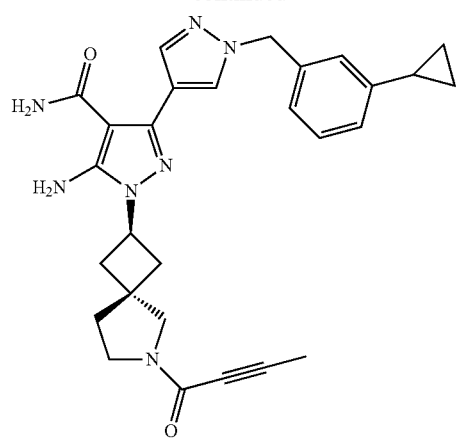
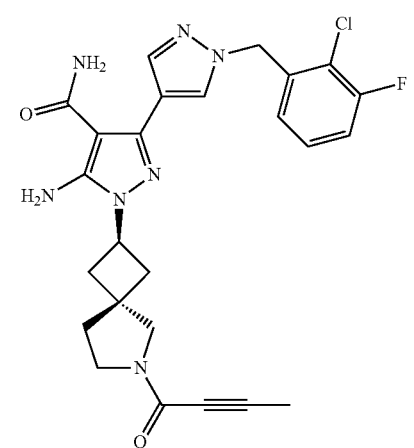
210
-continued
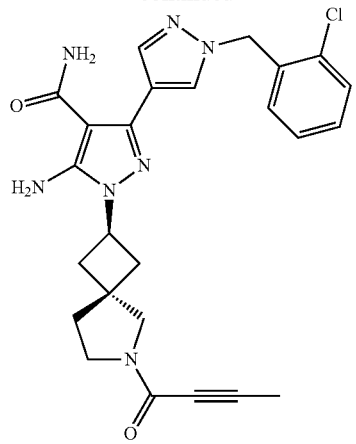
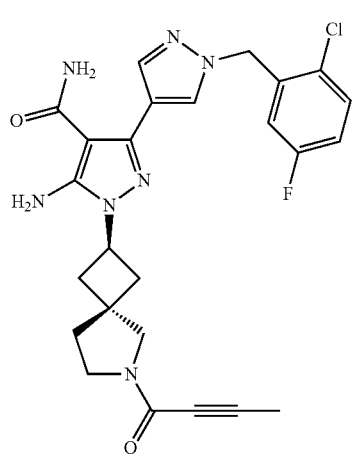
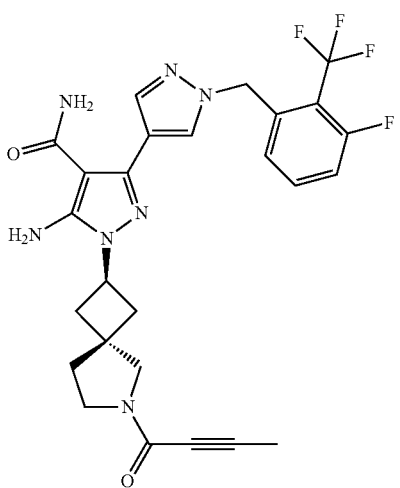

211
-continued
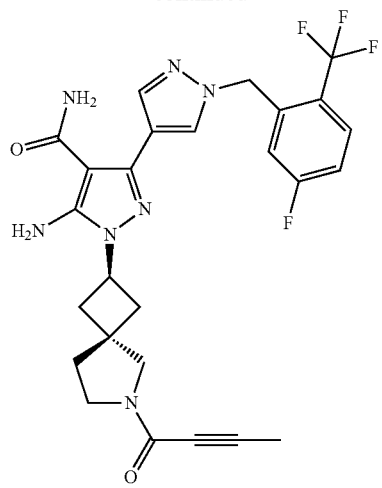
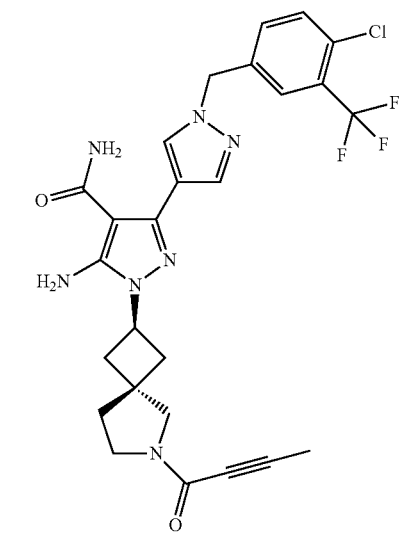
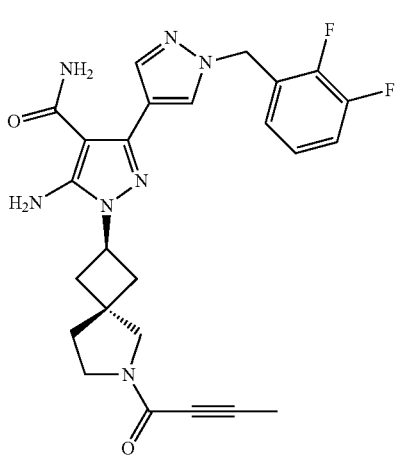
or
212
-continued
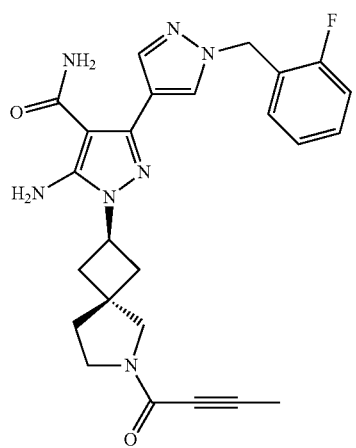 [SMILES: CC#CC(=O)N1CC[C@]2(C1)C[C@H](n1nc(-c3cnn(Cc4ccccc4F)c3)c(C(N)=O)c1N)C2]
or a pharmaceutically acceptable salts or hydrates thereof.
11. The compound according to claim 10 of the formula:
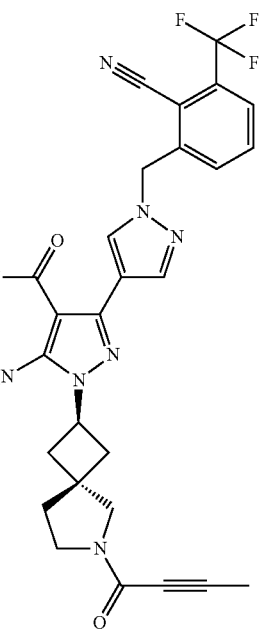
or a pharmaceutically acceptable salt thereof.

12. The compound according to claim 10 of the formula:

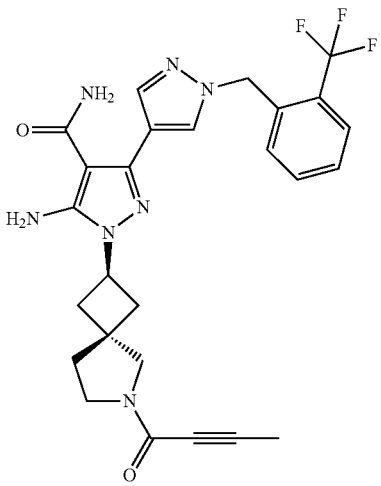 [SMILES: CC#CC(=O)N1CC[C@]2(C1)C[C@H](n1nc(-c3cnn(Cc4ccccc4C(F)(F)F)c3)c(C(N)=O)c1N)C2]

or a pharmaceutically acceptable salt thereof.

13. The compound according to claim 10 of the formula:

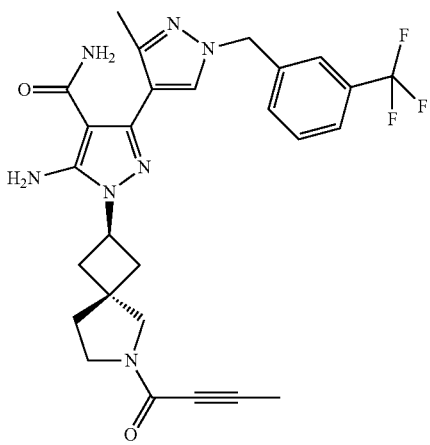 [SMILES: CC#CC(=O)N1CC[C@]2(C1)C[C@H](n1nc(-c3cn(Cc4cccc(C(F)(F)F)c4)nc3C)c(C(N)=O)c1N)C2]

or a pharmaceutically acceptable salt thereof.

14. The compound according to claim 10 of the formula:

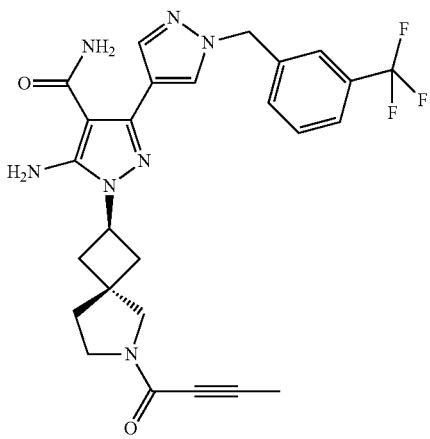 [SMILES: CC#CC(=O)N1CC[C@]2(C1)C[C@H](n1nc(-c3cnn(Cc4cccc(C(F)(F)F)c4)c3)c(C(N)=O)c1N)C2]

or a pharmaceutically acceptable salt thereof.

15. The compound according to claim 10 of the formula:

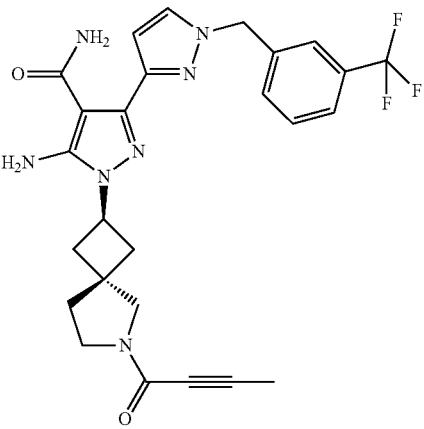 [SMILES: CC#CC(=O)N1CC[C@]2(C1)C[C@H](n1nc(-c3ccn(Cc4cccc(C(F)(F)F)c4)n3)c(C(N)=O)c1N)C2]

or a pharmaceutically acceptable salt thereof.

16. The compound according to claim 10 of the formula:

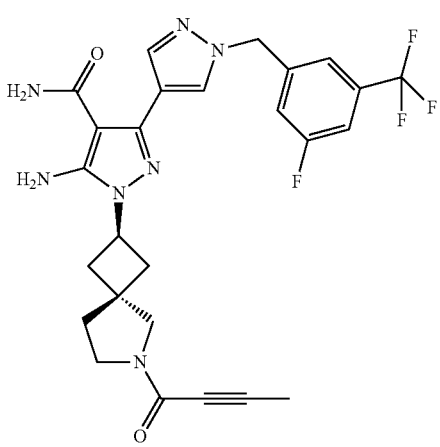 [SMILES: CC#CC(=O)N1CC[C@]2(C1)C[C@H](n1nc(-c3cnn(Cc4cc(F)cc(C(F)(F)F)c4)c3)c(C(N)=O)c1N)C2]

or a pharmaceutically acceptable salt thereof.

17. The compound according to claim 10 of the formula:

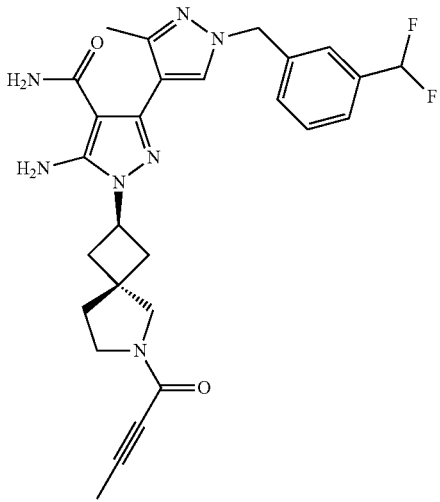 [SMILES: CC#CC(=O)N1CC[C@]2(C1)C[C@H](n1nc(-c3cn(Cc4cccc(C(F)F)c4)nc3C)c(C(N)=O)c1N)C2]

or a pharmaceutically acceptable salt thereof.

18. A pharmaceutical composition comprising a therapeutically effective amount of a compound according to claim 1 or a pharmaceutically acceptable salt thereof.

19. A method of treating a disease chosen from rheumatoid arthritis, systemic lupus erythromatosis, lupus nephritis, Sjogren's disease, vasculitis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis and uveitis, comprising administering to a patient a therapeutically effective amount of a compound according to claim 1 or a pharmaceutically acceptable salt or hydrate thereof.

20. A process for preparation of a compound of claim 1, which comprises:

(i) coupling a compound of formula A

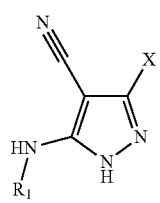
A with a compound of formula E

E to form a compound of formula G

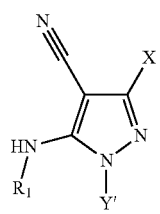
G wherein each $R_1$ is independently chosen from hydrogen or methyl; X is a halogen; LG is a leaving group; and Y' is $C_6$-$C_8$ spirocycle containing 1 ring nitrogen capped by a protecting group;

(ii) coupling the compound of formula G with a compound of formula B or a heterocyclic boronic ester or acid of formula C

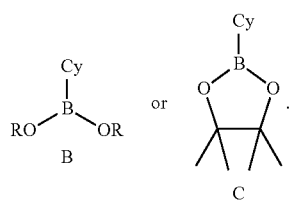
B    C wherein each R group of the compound of formula C is H, alkyl, or both R groups are connected to form a ring;

in presence of a suitable base and palladium catalyst followed by hydrolysis of the nitrile to carboxamide to form a compound of formula (II-1)

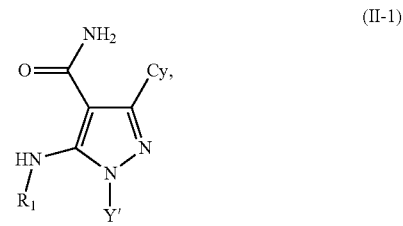
(II-1)

wherein Cy in the compound of formula (II-1) is chosen from

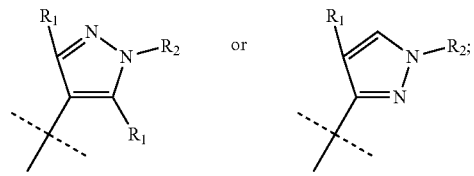

$R_2$ is L-Ar, wherein Ar is phenyl or pyridinyl and each is optionally substituted by one or more of halogen, halo $C_{1-4}$ alkyl, $C_{1-4}$ alkyl, $C_{1-4}$ alkoxy, —CN, halo $C_{1-4}$ alkoxy, or cycloalkyl;

and L is —(CH$_2$)— or —(CHCH$_3$)—; and (iii) deprotecting the capped nitrogen of the compound of formula (II-1) under an acidic condition and coupling the deprotected compound of formula (II-1) with a compound chosen from

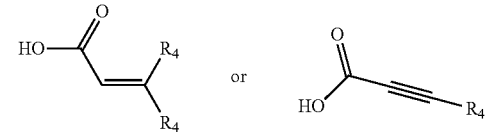

to form a compound of formula (I)

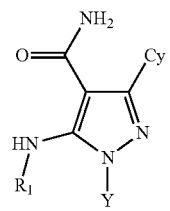
(I)

wherein Y is $C_6$-$C_8$ spirocycle containing 1 ring nitrogen linked to $R_3$, wherein R₃ is
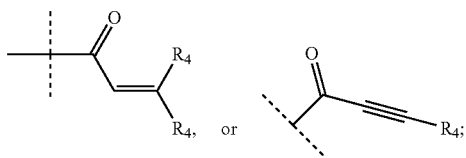
and
each R₄ is independently chosen from hydrogen, C₁₋₄ alkyl, or C₃₋₄ cycloakyl;
or a pharmaceutically acceptable salt thereof.
21. A compound of formula:
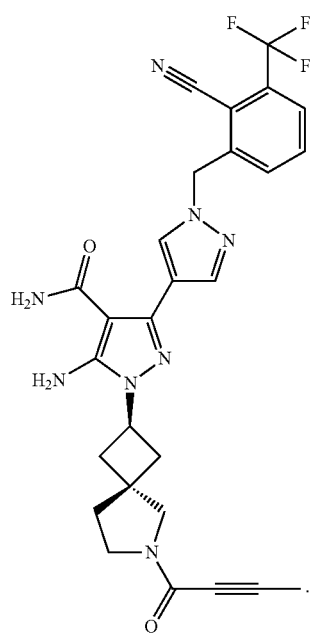 [SMILES: CC#CC(=O)N1CC[C@]2(C1)C[C@H](n1nc(-c3cnn(Cc4cccc(C(F)(F)F)c4C#N)c3)c(C(N)=O)c1N)C2]
22. A compound of formula:
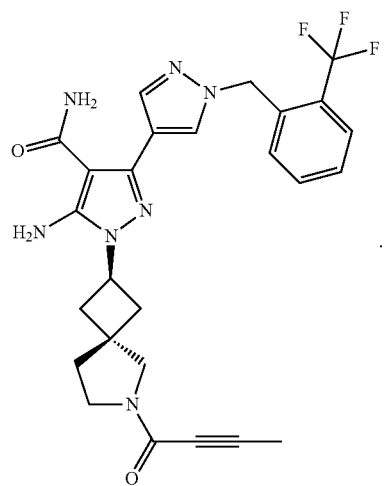 [SMILES: CC#CC(=O)N1CC[C@]2(C1)C[C@H](n1nc(-c3cnn(Cc4ccccc4C(F)(F)F)c3)c(C(N)=O)c1N)C2]
23. A compound of forumla:
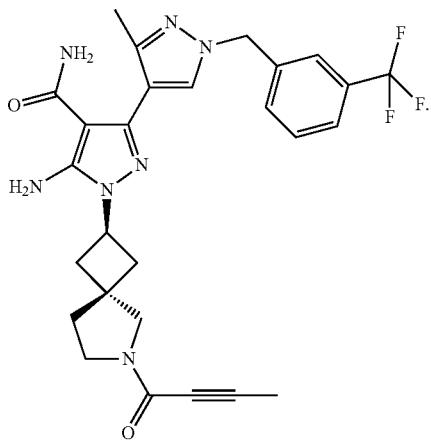 [SMILES: CC#CC(=O)N1CC[C@]2(C1)C[C@H](n1nc(-c3cn(Cc4cccc(C(F)(F)F)c4)nc3C)c(C(N)=O)c1N)C2]
24. A compound of formula:
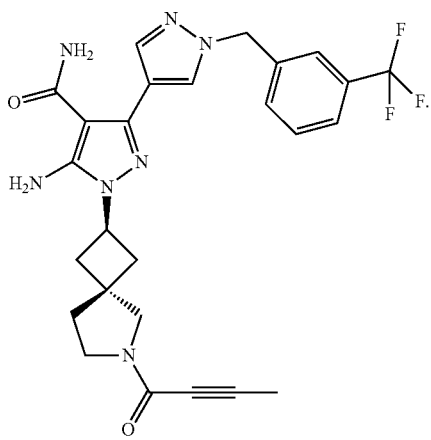 [SMILES: CC#CC(=O)N1CC[C@]2(C1)C[C@H](n1nc(-c3cnn(Cc4cccc(C(F)(F)F)c4)c3)c(C(N)=O)c1N)C2]
25. A compound of formula:
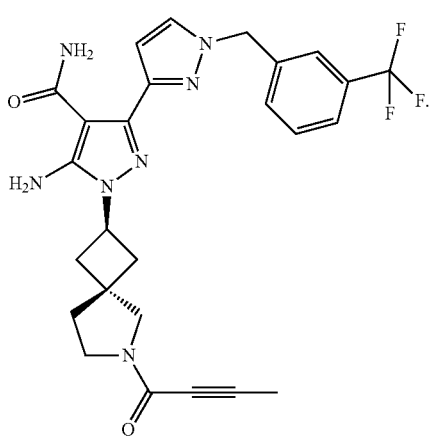 [SMILES: CC#CC(=O)N1CC[C@]2(C1)C[C@H](n1nc(-c3ccn(Cc4cccc(C(F)(F)F)c4)n3)c(C(N)=O)c1N)C2]

26. A compound of formula:
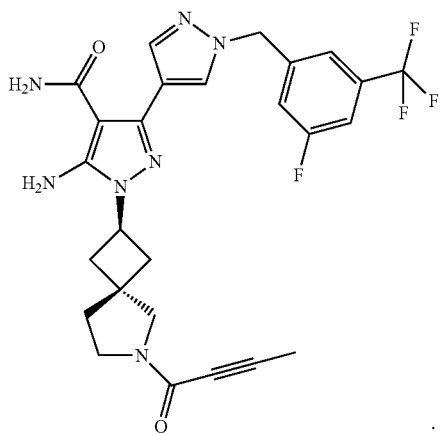 [SMILES: CC#CC(=O)N1CC[C@]2(C1)C[C@H](n1nc(-c3cnn(Cc4cc(F)cc(C(F)(F)F)c4)c3)c(C(N)=O)c1N)C2]
27. A compound of formula:
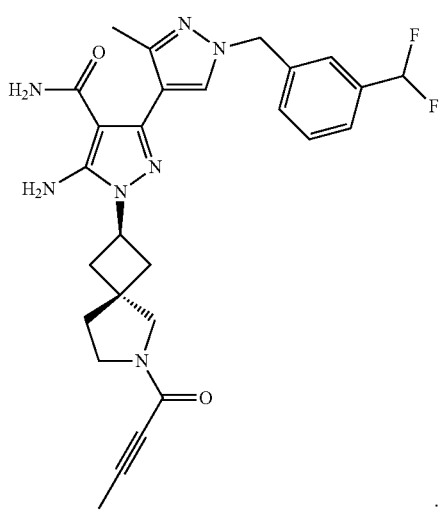 [SMILES: CC#CC(=O)N1CC[C@]2(C1)C[C@H](n1nc(-c3cn(Cc4cccc(C(F)F)c4)nc3C)c(C(N)=O)c1N)C2]
28. The compound according to claim 10 of the formula:
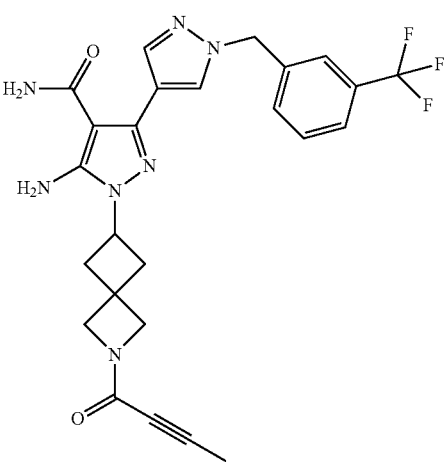 [SMILES: CC#CC(=O)N1CC2(CC(n3nc(-c4cnn(Cc5cccc(C(F)(F)F)c5)c4)c(C(N)=O)c3N)C2)C1]
29. The compound according to claim 10 of the formula:
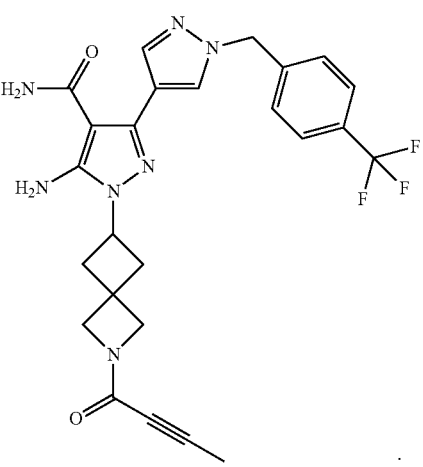 [SMILES: CC#CC(=O)N1CC2(CC(n3nc(-c4cnn(Cc5ccc(C(F)(F)F)cc5)c4)c(C(N)=O)c3N)C2)C1]
30. The compound according to claim 10 of the formula:
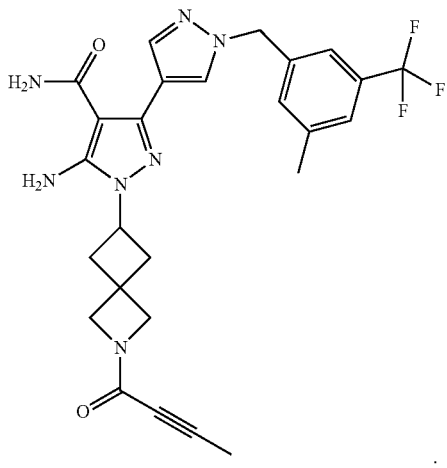 [SMILES: CC#CC(=O)N1CC2(CC(n3nc(-c4cnn(Cc5cc(C)cc(C(F)(F)F)c5)c4)c(C(N)=O)c3N)C2)C1]

31. A compound of formula:
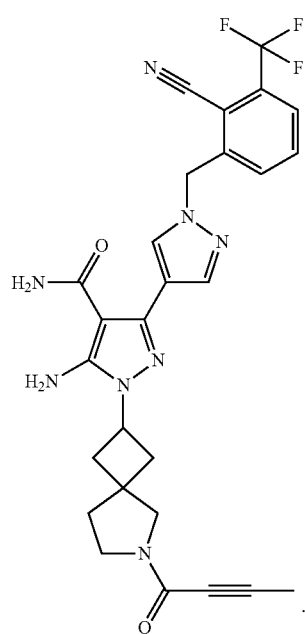 [SMILES: CC#CC(=O)N1CCC2(CC(n3nc(-c4cnn(Cc5cccc(C(F)(F)F)c5C#N)c4)c(C(N)=O)c3N)C2)C1]
32. A compound of formula:
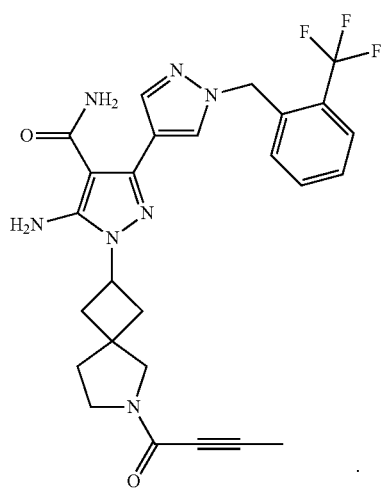 [SMILES: CC#CC(=O)N1CCC2(CC(n3nc(-c4cnn(Cc5ccccc5C(F)(F)F)c4)c(C(N)=O)c3N)C2)C1]
33. A compound of formula:
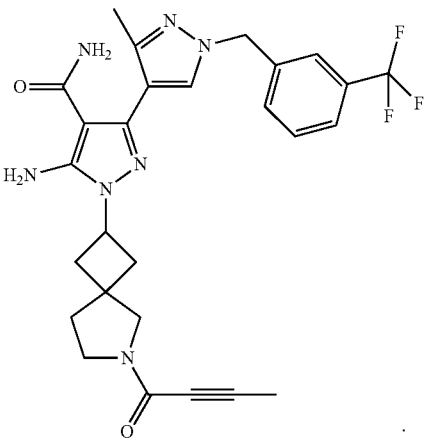 [SMILES: CC#CC(=O)N1CCC2(CC(n3nc(-c4cn(Cc5cccc(C(F)(F)F)c5)nc4C)c(C(N)=O)c3N)C2)C1]
34.
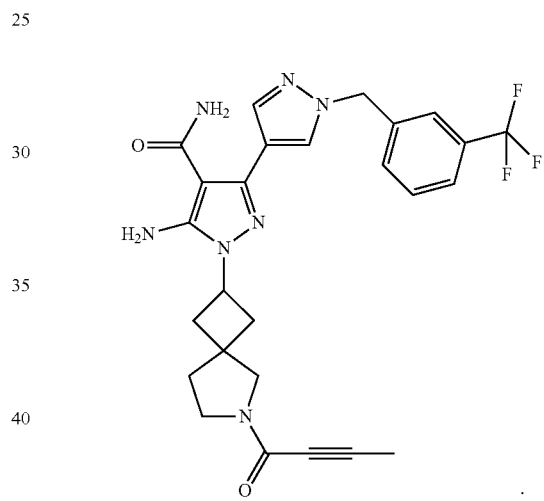
35. A compound of formula:
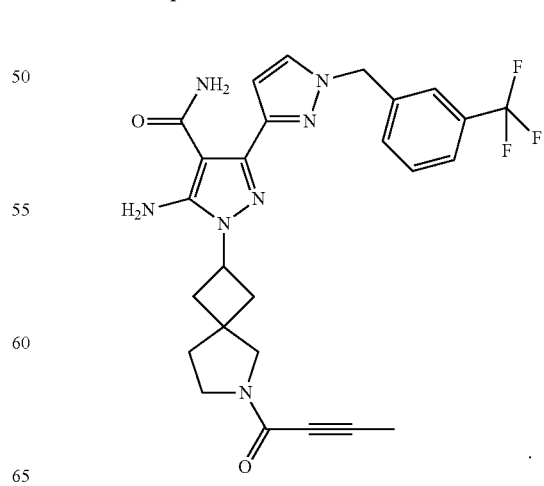

36. A compound of formula:
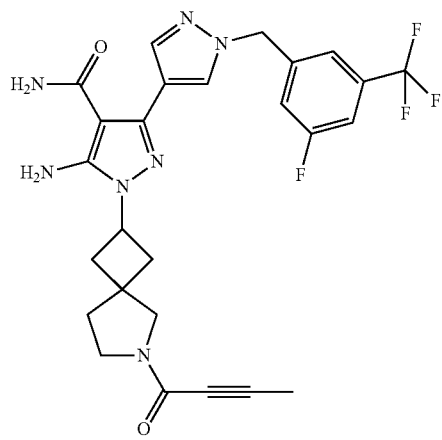 [SMILES: CC#CC(=O)N1CCC2(CC(n3nc(-c4cnn(Cc5cc(F)cc(C(F)(F)F)c5)c4)c(C(N)=O)c3N)C2)C1]
37. A compound of formula:
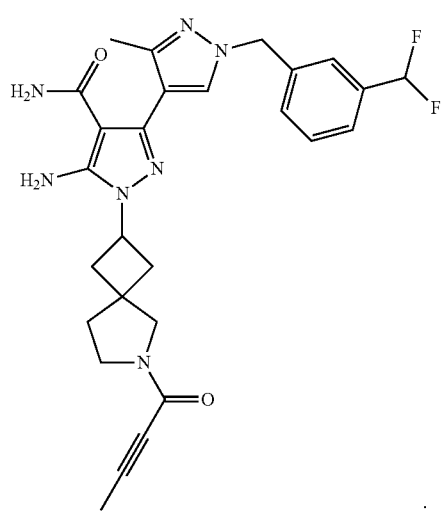 [SMILES: CC#CC(=O)N1CCC2(CC(n3nc(-c4cn(Cc5cccc(C(F)F)c5)nc4C)c(C(N)=O)c3N)C2)C1]
38. The compound according to claim 10 of the formula:
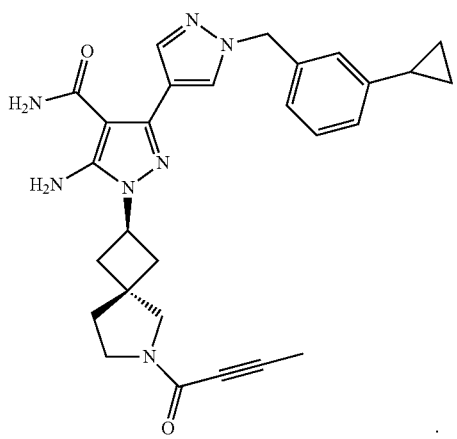 [SMILES: CC#CC(=O)N1CC[C@]2(C1)C[C@H](n1nc(-c3cnn(Cc4cccc(C5CC5)c4)c3)c(C(N)=O)c1N)C2]
39. The compound according to claim 10 of the formula:
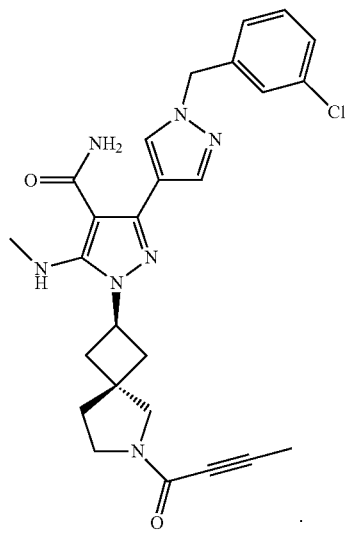 [SMILES: CC#CC(=O)N1CC[C@]2(C1)C[C@H](n1nc(-c3cnn(Cc4cccc(Cl)c4)c3)c(C(N)=O)c1NC)C2]
40. The compound according to claim 10 of the formula:
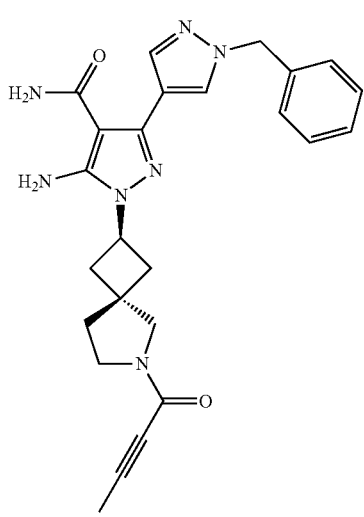
* * * * *